US010117930B2

(12) United States Patent
Ilan et al.

(10) Patent No.: US 10,117,930 B2
(45) Date of Patent: *Nov. 6, 2018

(54) ANTI-LPS ENRICHED IMMUNOGLOBULIN PREPARATIONS FOR THE TREATMENT AND/OR PROPHYLAXIS OF A PATHOLOGIC DISORDER

(75) Inventors: Yaron Ilan, Jerusalem (IL); Gadi Lalazar, Zion (IL); Tomer Adar, Modi'in (IL); Meir Mizrahi, Modi'in (IL); Ami Ben-Ya'acov, Jerusalem (IL)

(73) Assignee: Immuron Limited, Blackburn North (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/265,252

(22) PCT Filed: Apr. 27, 2010

(86) PCT No.: PCT/IL2010/000339
§ 371 (c)(1),
(2), (4) Date: Feb. 7, 2012

(87) PCT Pub. No.: WO2010/125565
PCT Pub. Date: Nov. 4, 2010

(65) Prior Publication Data
US 2012/0135007 A1 May 31, 2012

Related U.S. Application Data

(60) Provisional application No. 61/172,922, filed on Apr. 27, 2009.

(51) Int. Cl.
*A61K 39/40* (2006.01)
*A61K 39/395* (2006.01)
*C07K 16/04* (2006.01)
*C07K 16/12* (2006.01)
*C07K 16/26* (2006.01)
*A61K 39/00* (2006.01)

(52) U.S. Cl.
CPC ........ *A61K 39/39508* (2013.01); *C07K 16/04* (2013.01); *C07K 16/1232* (2013.01); *C07K 16/26* (2013.01); *A61K 2039/505* (2013.01); *A61K 2039/507* (2013.01); *C07K 2317/12* (2013.01)

(58) Field of Classification Search
None
See application file for complete search history.

(56) References Cited

U.S. PATENT DOCUMENTS

| | | | |
|---|---|---|---|
| 4,550,019 A | 10/1985 | Polson | |
| 4,748,018 A | 5/1988 | Stolle et al. | |
| 6,537,500 B1 | 3/2003 | Brenner et al. | |
| 2004/0161427 A1 | 8/2004 | Nash et al. | |

FOREIGN PATENT DOCUMENTS

| | | |
|---|---|---|
| CA | 1101333 A | 5/1981 |
| EP | 1795204 A4 | 10/2009 |
| JP | 53130411 A | 11/1978 |
| JP | 58154513 A | 9/1983 |
| JP | 7206402 A | 8/1995 |
| WO | WO1992016624 A1 | 10/1992 |
| WO | WO199508562 A1 | 3/1995 |
| WO | WO1999061468 A1 | 2/1999 |
| WO | WO2003080082 A1 | 10/2003 |
| WO | WO2003097094 A1 | 11/2003 |
| WO | WO2004078209 A1 | 9/2004 |
| WO | WO2006035979 A1 | 4/2006 |
| WO | WO2006053383 A1 | 5/2006 |
| WO | WO2008025099 A1 | 3/2008 |
| WO | WO2009113065 A1 | 9/2009 |
| WO | WO2012023051 A9 | 6/2012 |

OTHER PUBLICATIONS

Ramos-Casals et al., "Systemic autoimmune diseases co-existing with chronic hepatitis C virus infection (the HISPAMEC Registry): patterns of clinical and immunological expression in 180 cases", Journal of Internal Medicine 2005; 257: 549-557.*
Anderson et al., "An assessment of the clinical utility of serum ALT and AST in chronic hepatitis C", Hepatology Research 18:63-71, 2000.*
Ruiz et al., "Lipopolysaccharide-Binding Protein Plasma Levels and Liver TNF-Alpha Gene Expression in Obese Patients: Evidence for the Potential Role of Endotoxin in the Pathogenesis of Non-Alcoholic Steatohepatitis", Obesity Surgery, 17, 1374-1380, 2007.*
Gao et al., "Effects of Traditional Chinese Medicine on Endotoxin and Its Receptors in Rats with Non-Alcoholic Steatohepatitis", Inflammation, vol. 31, No. 2, Apr. 2008.*
Admyre et al; Exosomes with Immune Modulatory Features are Present in Human Breast Milk; J. Immunol.; 2007; 179:1969-1978.
Amaral et al; In vitro reactivity and growth inhibition of EPEC serotype O111 and STEC serotypes O111 and O157 by homologous and heterologous chicken egg yolk antibody; Vet Res Commun; 2008; 32:281-290.

(Continued)

*Primary Examiner* — Gary B Nickol
*Assistant Examiner* — Khatol S Shahnan Shah
(74) *Attorney, Agent, or Firm* — Fish & Richardson P.C.

(57) ABSTRACT

The invention relates to the use of preparations enriched with anti LPS antibodies, such as those derived from mammalian colostrum or avian eggs, and optionally further antibodies against disease-associated antigens, colostrums, milk or milk product component/s and any adjuvants for treating, delaying or preventing the progression of a pathologic disorder such as chronic liver disease, cirrhosis and any complication or disorder associated therewith. The invention further relates to combined compositions comprising a combination of anti-LPS enriched antibody preparations and antibodies recognizing at least one antigen specific for a pathologic disorder and uses thereof in the treatment of immune-related disorders.

6 Claims, 22 Drawing Sheets

(56) References Cited

OTHER PUBLICATIONS

Bedogni et al; Natural Course of Chronic HCV and HBV Infection and Role of Alcohol in the General Population: The Dionysos Study; American Journal of Gastroenterology; 2008; 103:2248-2253.
Bluestone et al; Therapeutic vaccination using CD4+CD25+ antigen-specific regulatory T cells; PNAS; 2004; 101 (2):14622-14626.
Brandon et al; The Mechanism of Transfer of Immunoglobulin Into Mammary Secretion of Cows; Aust. J. Exp. Biol. Med. Sci.; 1971; 49:613-623.
Cohen et al; Antibiotic prophylaxis for spontaneous bacterial peritonitis in cirrhotic patients with ascites, without gastro-intestinal bleeding (Review); Cochrane Database of Systematic Reviews; 2009; Issue 2, Art. No. CD004791; John Wiley & Sons, Ltd.
Czaja et al; Lipopolysaccharide-neutralizing Antibody Reduces Hepatocyte Injury from Acute Hepatotoxin Administration; Hepatology; 1994; 19:1282-1289.
El-Naggar et al; Bacterial DNA and its consequences in patients with cirrhosis and culture-negative, non-neutrocytic ascites; Journal of Medical Microbiology; 2008; 57:1533-1538.
Faria et al; Oral tolerance: Therapeutic implications for autoimmune diseases; Clinical & Developmental Immunology; Jun.-Dec. 2006; 13(2-4):143-157.
Feingold et al; Endotoxin rapidly induces changes in lipid metabolism that produce hypertriglyceridemia: low doses stimulate hepatic triglyceride production while high doses inhibit clearance; J. Lipid Res.; 1992; 33:1765-1776.
Freedman et al; Milk Immunoglobulin with Specific Activity against Purified Colonization Factor Antigens Can Protect against Oral Challenge with Enterotoxigenic *Escherichia coli*; The Journal of Infectious Diseases; 1998; 177:662-667.
Godfrey et al; Control points in NKT-cell development; Immunology; 2007; 7:505-518; Nature Publishing Group.
Homann et al; Autoreactive CD4+ T Cells Protect from Autoimmune Diabetes via Bystander Suppression Using the IL-4/Stat6 Pathway; Immunity; 1999; 11:463-472.
Homann et al; Insulin in Oral Immune 'Tolerance': A One-Amino Acid Change in the B Chain Makes the Difference; J. Immunol.; 1999; 163:1833-1838.
Jones et al; Enhanced pepsin digestion: a novel process for purifying antibody F(ab')2 fragments in high yield from serum; Journal of Immunological Methods; 2002; 263:57-74.
Kahn et al; Mechanisms linking obesity to insulin resistance and type 2 diabetes; Nature; 2006; 444:840-846.
Larche et al; Peptide-based therapeutic vaccines for allergic and autoimmune diseases; Nature Medicine Supplement; 2005; 11(4):S69-S76.
Machida et al; Toll-like receptor 4 mediates synergism between alcohol and HCV in hepatic oncogenesis involving stem cell marker Nanog; PNAS; 2009; 106(5):1548-1553.
Margalit et al; Glucocerebroside Ameliorates the Metabolic Syndrome in OB/OB Mice; The Journal of Pharmacology and Experimental Therapeutics; 2006; 319(1):105-110.
Margalit et al; Induction of immune tolerance: a role for Natural killer T lymphocytes?; Liver International; 2005; 25:501-504.
Martin et al; Bovine Milk Gangliosides: Changes in Ceramide Moiety with Stage of Lactation; Lipids; 2001; 36:291-298.
Martin-Blondel et al; Low interleukin-10 production by monocytes of patients with a self-limiting hepatitis C virus infection; Journal of Viral Hepatitis; 2009; 16:485-491.
Nagao et al; Elevated Levels and Different Repertoire Profile of Colostral Anti-LPS Antibodies May Have a Significant Role in Compensating Newborn Immunity; Scand. J. Immunol.; 2001; 53:602-609.
Nagatomo et al; Microarray analysis of human milk cells: persistent high expression of osteopontin during the lactation period; Clin. Exp. Immunol.; 2004; 138:47-53.
Nikoopour et al; Therapeutic Benefits of Regulating Inflammation in Autoimmunity; Inflammation & Allergy—Drug Targets; 2008; 7:203-210.
Novak et al; Regulation of Type 1 Diabetes by NKT Cells; International Reviews of Immunology; 2007; 26:49-72.
Nowak, Michael ; Invariant NKT Cells and Tolerance; International Reviews of Immunology; 2007; 26:95-119.
Oppenheim et al; Alarmins Initiate Host Defense; Immune-Mediated Diseases: From Theory to Therapy; 2007; pp. 185-194; Springer.
Oppenheim et al; Alarmins: chemotactic activators of immune responses; Current Opinion in Immunology; 2005; 17:359-365.
Palmeira et al; Passive immunity acquisition of maternal anti-enterohemorrhagic *Escherichia coli* (EHEC) O157:H7 IgG antibodies by the newborn; Eur. J. Pediatr.; 2007; 166:413-419.
Poggi et al; The inflammatory receptor CD40 is expressed on human adipocytes: contribution to crosstalk between lymphocytes and adipocytes; Diabetologia; 2009; 52:1152-1163.
Putnam et al; CD4+CD25high regulatory T cells in human autoimmune diabetes; Journal of Autoimmunity; 2005; 24:55-62.
Safadi et al; Treatment of Chronic Hepatitis B Virus Infection via Oral Immune Regulation Toward Hepatitis B Virus Proteins; The American Journal of Gastroenterology; 2003; 98(11):2505-2515.
Sala-Vila et al; Lipid composition in human breast milk from Granada (Spain): Changes during lactation; Nutrition; 2005; 21:467-473.
Song et al; Clinical outcomes of spontaneous bacterial peritonitis due to extended-spectrum beta-lactamase-producing *Escherichia coli* and *Klebsiella* species: A retrospective matched case-control study; BMC Infectious Diseases; 2009; 9:41-46.
Tacket et al; Protection by Milk Immunoglobulin Concentrate Against Oral Challenge with Enterotoxigenic *Escherichia Coli*; The New England Journal of Medicine; 1988; 318:1240-1243.
Tarbell et al; CD25+CD4+ T Cells, Expanded with Dendritic Cells Presenting a Single Autoantigenic Peptide, Suppress Autoimmune Diabetes; J. Exp. Med.; 2004; 199(11):1467-1477.
The Diabetes Prevention Trial-Type 1 Study Group (Jay S. Skyler, Study Chairman); Effects of Oral Insulin in Relatives of Patients with Type 1 Diabetes; Diabetes Care; 2005; 1068-1076.
Turkenkopf et al; Regional and Genotypic Differences in Stromal-Vascular Cells from Obese and Lean Zucker Rats; International Journal of Obesity; 1988; 12:515-524.
Van et al; All-trans Retinoic Acid Inhibits Type 1 Diabetes by T Regulatory (Treg)-Dependent Suppression of Interferon-gamma-Producing T-cells Without Affecting Th17 Cells; Diabetes; 2009; 58:146-155.
Van Dissel et al; Bovine antibody-enriched whey to aid in the prevention of a relapse of Clostridium difficile-associated diarrhoea: preclinical and preliminary clinical data; Journal of Medical Microbiology; 2005; 54:197-205.
Vignali et al; How regulatory T cells work; Nat. Rev. Immunol.; 2008; 8(7):523-532.
Wershil et al; Gastrointestinal mucosal immunity; J. Allergy Clinical Immunol.; 2008; 121:S380-383.
Yang et al; Human Ribonuclease A Superfamily Members, Eosinophil-Derived Neurotoxin and Pancreatic Ribonuclease, Induce Dendritic Cell Maturation and Activation; J. Immunol.; 2004; 173(10):6134-6142.
Yokoyama et al; Oral passive immunization against experimental salmonellosis in mice using chicken egg yolk antibodies specific for *Salmonella enteritidis* and *S. typhimurium*; Vaccine; 1998; 16(4):388-393.
Adams et al., "Nonalcoholic fatty liver disease," Can. Med. Assoc. J. 172:899-905 (2005).
Akita and Nakai, "Comparison of four purification methods for the production of immunoglobulins from eggs laid by hens immunized with an enterotoxigenic *E. coli* strain," J. Immunol. Methods, 160(2):207-214 (1993).
Akita and Nakai, "Production and purification of Fab' fragments from chicken egg yolk immunoglobulin Y (IgY)," J. Immunol Methods, 162(2):155-164 (1993).

(56) References Cited

OTHER PUBLICATIONS

Clark et al., "Nonalcoholic Fatty Liver Disease: an Under-recognized Cause of Cryptogenic Cirrhosis," J. Am. Med. Assoc. 289:3000-3004 (2003).
Dos Santos et al., "Serum laminin, type IV collagen and hyaluronan as fibrosis markers in non-alcoholic fatty liver disease," Braz. J. Med. Biol. Res. 38:747-753 (2005).
DuPont et al., "Pathogenesis of *Escherichia coli* diarrhea," New England J. of Medicine, 285: 1-9 (1971).
Evans et al., "Three characteristics associated with enterotoxigenic *Escherichia coli* isolated from man," Infect. Immunity, 8: 322-328 (1973).
Ilan et al., "Induction of regulatory T cells decreases adipose inflammation and alleviates insulin resistance in ob/ob mice," Proc Natl Acad Sci USA 107:9765-9770 (2010).
Maghraby et al., "Anti-schistosomal activity of colostral and mature camel milk on Schistosoma mansoni infected mice," Asia Pacific Journal of Clinical Nutrition, 14(4):432-438 (2005).
McConnell et al., "Characterization of a new putative colonization factor (CS17) from a human enterotoxigenic *Escherichia coli* of serotype 0114:H21 which produces only heat-labile enterotoxin," J. Infect. Dis., 161(2): 343-347 (1990).
Neuschwander-Tetri et al., "Nonalcoholic Steatohepatitis: Summary of an AASLD Single Topic Conference," Hepatology37:1202-1219 (2003).
Ramos-Casals et al., "Systemic autoimmune diseases co-existing with chronic hepatitis C virus infection (the HISPAMEC Registry): patterns of clinical and immunological expression in 180 cases," Journal of Internal Medicine, 257:549-557 (2005).
Ryan et al., "Associations between liver histology and severity of the metabolic syndrome in subjects with nonalcoholic fatty liver disease," Diabetes Care, 28:1222-1224 (2005).
Golay et al., "Cholesterol-Lowering Effect of Skim Milk from Immunized Cows in Hypercholesterolemic Patients," The American Journal of Clinical Nutrition, 52(6):1014-1019 (Jan. 1, 1990).
Office Action dated Dec. 2, 2014 in Mexican Patent Application MS/a/2011/011376 (Ilan et al., "anti-LPS enriched immunoglobulin preparation for use in the treatment and/or prophylaxis of a pathologic disorder" filed on Oct. 5, 2011) with English translation (7 pages).
Office Action dated Jun. 27, 2014 in Eurasian Application No. 201171304/28 (Ilan et al., "anti-LPS enriched immunoglobulin preparation for use in the treatment and/or prophylaxis of a pathologic disorder" filed on Oct. 5, 2011) with English Translation (3 pages).
Office Action dated Oct. 7, 2014 in European Patent Application 11793860.5 (Ilan et al., "anti-LPS enriched limmunoglobulin for Use in Treatment and /or Prophylaxis of a Pathologic Disorder" filed on Jan. 31, 2013) (6 pages).
International Search Report dated Mar. 7, 2012 in PCT/IB2011/002596 (Ilan et al., "anti-LPs enriched limmunoglobulin for Use in Treatment and /or Prophylaxis of a Pathologic Disorder" filed on Jan. 31, 2013).
Office Action dated Feb. 6, 2013 in Australian Application No. 2010243205 (Ilan et al., "anti-LPS enriched immunoglobulin preparation for use in the treatment and/or prophylaxis of a pathologic disorder" filed on Oct. 5, 2011) (3 pages).
Office Action dated Oct. 14, 2013 in Australian Application No. 2011290478 (Ilan et al., "anti-LPS enriched limmunoglobulin for Use in Treatment and /or Prophylaxis of a Pathologic Disorder" filed on Jan. 31, 2013) (3 pages).
Office Action dated Oct. 16, 2013 in Eurasian Application No. 201171304/28 (Ilan et al., "anti-LPS enriched immunoglobulin preparation for use in the treatment and/or prophylaxis of a pathologic disorder" filed on Oct. 5, 2011) (3 pages).
Office Action dated Jul. 28, 2014 in European Patent Application 10721856.2 (Ilan et al., "anti-LPS enriched immunoglobulin preparation for use in the treatment and/or prophylaxis of a pathologic disorder" filed on Oct. 5, 2011).
Office Action dated May 27, 2014 in Japanese Patent Application 2012-507877 (Ilan et al., "anti-LPS enriched immunoglobulin preparation for use in the treatment and/or prophylaxis of a pathologic disorder" filed on Oct. 5, 2011).
Office Action dated Apr. 1, 2014 in Mexican Patent Application MS/a/2011/011376 (Ilan et al., "anti-LPS enriched immunoglobulin preparation for use in the treatment and/or prophylaxis of a pathologic disorder" filed on Oct. 5, 2011).
Office Action dated May 22, 2015 in Mexican Patent Application MS/a/2011/011376 (Ilan et al., "anti-LPS enriched immunoglobulin preparation for use in the treatment and/or prophylaxis of a pathologic disorder" filed on Oct. 5, 2011) with English translation (6 pages).
Office Action dated Oct. 15, 2015 in European Patent Application 10721856.2 (Ilan et al., "anti-LPS enriched immunoglobulin preparation for use in the treatment and/or prophylaxis of a pathologic disorder" filed on Oct. 5, 2011) (7 pages).
Yang et al., "Obesity increases sensitivity to endotoxin liver injury: Implications for the pathogenesis of steatohepatitis," Proc. Natl. Acad. Sol. USA 94:2557-2562, 1997.
'Medscape.com' [online]. "Drug-Induced Hepatotoxicity," Oct. 9, 2014, [retrieved on Apr. 17, 2015]. Retrieved from the Internet: URL<http://emedicine.medscape.com/article/169814-overview>. 11 pages.
'Medscape.com' [online]. "Pathology of Nonalcoholic Steatohepatitis," Jun. 20, 2013, [retrieved on Apr. 17, 2015]. Retrieved from the Internet: URL<http://emedicine.medscape.com/article/2038493-overview>. 5 pages.
'Nih.gov' [online]. "Nonalcoholic Steatohepatitis," Nov. 2006, [retrieved on Mar. 1, 2016]. Retrieved from the Internet: URL<http://www.niddk.nih.gov/health-information/health-topics/liver-disease/nonalcoholic-steatohepatitis/Documents/NASH_508.pdf>. 6 pages.
'Worldgastroenterology.org' [online] "Nonalcoholic Fatty Liver Disease—A Growing Public Health Problem," publication date not available, [retrieved on Jul. 15, 2016]. Retrieved from the Internet: URL<http://www.world gastroenterology.org/publications/e-wgn/e-wgn-expert-point-of-view-articles-collection/nonalcoholic-fatty-liver-disease-a-growing-public-health-problem>. 4 pages.
'Worldgastroenterology.org' [online]. "Nonalcoholic Fatty Liver Disease and Nonalcoholic Steatohepatitis," Jun. 2012, [retrieved on Mar. 1, 2016]. Retrieved from the Internet: URL<http://www.worldgastroenterology.org/guidelines/global-guidelines/nafld-nash>. 29 pages.
Maier, "Medikamentose Therapie in der Hepatologie", Praxis : schweizer. Rundschau tor Medizin,, Noc. 2005, 94: 1907-1912 (with English summary).
Office Action issued in Mexican Patent Application MS/a/2011/011376 dated Dec. 2, 2014 with English translation (7 pages).
Office Action issued in Eurasian Application No. 201171304/28 dated Jun. 27, 2014 with English Translation (3 pages).
U.S. Appl. No. 13/817,414, filed Jan. 15, 2013, Yaron Ilan.

\* cited by examiner

ANTI-LPS ENRICHED IMMUNOGLOBULIN PREPARATIONS FOR THE TREATMENT AND/OR PROPHYLAXIS OF A PATHOLOGIC DISORDER

This application is a US National Stage under 35 USC § 371 of International Application Number PCT/IL2010/000339, filed on 27 Apr. 2010, which claims priority to U.S. Provisional Application No. 61/172,922, filed on 27 Apr. 2009, the entire contents of which are hereby incorporated by reference.

FIELD OF THE INVENTION

The invention relates to the use of preparations enriched with anti LPS antibodies, such as those derived from mammalian colostrum or avian eggs, and optionally further antibodies against disease-associated antigens, colostrums, milk or milk product component/s and any adjuvants for treating, delaying or preventing the progression of a pathologic disorder such as chronic liver disease, cirrhosis and any complication or disorder associated therewith. The invention further relates to combined compositions comprising a combination of anti-LPS enriched antibody preparations and antibodies recognizing at least one antigen specific for a pathologic disorder and uses thereof in the treatment of immune-related disorders.

BACKGROUND OF THE INVENTION

All publications mentioned throughout this application are fully incorporated herein by reference, including all references cited therein.

Chronic hepatitis is inflammation of the liver that lasts at least six months. Chronic hepatitis, although much less common than acute hepatitis, can persist for years, even decades. In most people, it is quite mild and does not cause significant liver damage. However, in some people, continued inflammation slowly damages the liver, eventually resulting in cirrhosis (severe scarring of the liver), liver failure, and sometimes liver cancer. Chronic hepatitis is usually caused by Hepatitis B virus (HBV) Hepatitis C virus (HCV) and drugs.

Chronic Hepatitis C virus (HCV) infection is characterized by the inability of the host to establish an effective immune response. At the same time chronic HCV infection is associated with persistent, abnormally high levels of immune activation. This activation contributes to liver damage and disease progression. Patients with chronic HCV infection have widely varying clinical courses, while some develop cirrhosis, others do not show progression of liver disease.

Several risk factors including concomitant ethanol consumption have been associated with accelerated liver damage and progression to cirrhosis. Patients with both chronic HCV and ethanol consumption have been found to have accelerated progression of liver disease. This has been associated with increased levels of LPS [Bedogni, G. Am. J. Gastroenterol. 103(9): 2248-53 (2008)]. Interestingly, a recent study has shown that the HCV nonstructural protein NS5A activates Toll-like receptor (TLR) 4 which is also activated by LPS [Machida, K. et al. Proc. Natl. Acad. Sci. USA, 106(5):1548-53 (2009].

LPS may not only be connected with progression of liver disease, but also with the perpetuation of chronic infection. When compared with patients with self limiting infection, monocytes from patients with chronic HCV produce significantly more IL-10 and TNF alpha in response to the HCV core protein or LPS [Martin-Blondel, G. et al. J. Viral. Hepatitis (Mar. 11, 2009)]. Thus, although translocation of gut microbial products, immune activation and progression of liver disease appear to be closely linked, proof of causality is lacking. Additionally, there appears to be a connection between LPS levels and viral clearance, though this needs to be elucidated. Thus, studies designed at clarifying these relationships are needed. If microbial translocation is driving immune activation and progression of liver disease, strategies that reduce or prevent microbial translocation may therefore have a significant impact on immune activation, and thus on the natural history of chronic HCV infection.

Spontaneous bacterial peritonitis (SBP) is a common and severe complication of chronic liver diseases, such as liver cirrhosis, portal hypertension and ascites. SBP occurs in up to 30% of patients, and is associated with an in-hospital mortality rate of up to 25%. Bacterial translocation into the stagnant and immune depleted peritoneal fluid is considered to be the main pathogenic mechanism of SBP. While paracentesis and broad spectrum antibiotic therapy constitute an effective treatment for acute infection, many patients suffer from recurrent episodes of SBP with pathogens which become increasingly resistant to antibiotic therapy [Song, K. H. et al. BMC Infect Dis. 9(1): 41 (2009)]. Methods for SBP prophylaxis using chronic antibiotics are controversial and associated with immergence of antibiotic resistant species [Cohen, M. J. et al. Cochrane Database Syst Rev. 2: CD004791 (2009)].

Recently, an increasing association has been found between bacterial translocation and the incidence of complications of cirrhosis. The levels of either bacterial products (ribosomal 16s RNA) in the serum or endotoxemia (LPS or LBP) have been correlated with variceal bleeding, hepatorenal syndrome and the hyperdynamic circulatory state found in cirrhotic patients [El-Naggar, M. M. et al. J. Med. Microbiol. 57(Pt 12):1533-8 (2008)].

For decades, various attempts have been made to obtain increased secretion of immunogen-specific antibodies via the mammary gland of farm animals. Such attempts are aimed at production of large quantities of immunogen-specific antibodies via milk. The antibody levels in mature milk, however, still remain low (approximately an order of magnitude) when compared to those that can be achieved in colostrum.

Colostrum (also known as first milk) is a form of milk produced by the mammary glands in late pregnancy and the few days after birth. In humans it has high concentrations of nutrients and antibodies, but it is small in quantity. Colostrum is high in carbohydrates, protein, mineral salts, vitamins and immunoglobulin. It also contains various floating cells such as granular and stromal cells, neutrophils, monocyte/macrophages and lymphocytes and includes growth factors, hormones and cytokines.

Leukocytes are also present in colostrum in large numbers which enable protection against viruses and bacteria. Colostral leukocytes enhance passive immunity of neonatal calf, especially in regard to antibodies and immunoglobulin classes which are essential for intestinal immunity.

The large numbers of secretory antibodies found in the colostrum help protect the mucous membranes in the throat, lungs, and intestines of the newborn. Bovine colostrum (BC) contains three major classes of immunoglobulins: IgG, IgM and IgA.

As indicated above, colostrum is quite a unique product that arises from a distinct physiological and functional state of the mammary gland. In ruminants, the principal compositional difference between colostrum and mature milk is the very high content of bioactive components such as lactoferrin and immunoglobulins [Tarbell, K. V. et al. J. Exp. Med. 199:1467-77 (2004); Bluestone, J. A. and Tang, Q. J. Autoimmun 24:55-62 (2005); Putnam, A. I. et al J. Autoimmun. 24:55-62 (2005)], of which IgG class makes up 80-90%.

The immunization of an animal such as a cow with specific antigens enables the production and harvest of specific antibodies that may be used for modulation of an immune response and thereby in the treatment of immune-related disorders. Accordingly, this method serves as an easy and safe means for generating antigen-specific antibodies and immune adjuvants.

Several previous patents and patent applications by some of the present inventors, described the use of specific bacterial pathogens antibodies, obtained from bovine colostrum for the passive treatment of infectious diseases. For example, WO 04/078209 by some of the present inventors describes compounds and compositions for the treatment or prophylaxis of gastrointestinal disorders prepared by immunizing a host animal with a vaccine comprising one or more cell wall antigens of enteric bacteria, specifically, gram negative bacteria. The hyper immune material produced is in the form of tablets for oral administration. WO 03/097094 describes the use of a hyper immune colostrum in the production of antibodies (whole IgG), or F(ab')2 antibodies fragments, conjugated with mammalian colostrum and colostrum extracts, for intranasal administration aimed at the prevention of symptoms arising from the presence of airborne pathogenic bacteria.

Mucosal tolerance is considered as an attractive approach for the treatment of autoimmune and inflammatory diseases due to the lack of toxicity, ease of administration, and antigen-specific mechanism of action [Wershil, B. K. and Furuta, G. T. J. Allergy Clin. Immunol. 121:S380-3; quiz S415 (2008); Faria, A. M. and Weiner, H. L. Clin. Dev. Immunol. 13:143-57 (2006)]. Hence, major attempts were made to generate stable colostrum-derived products suitable for oral and nasal administration. For Example, WO 95/08562 by some of the inventors, describes the method of obtaining high purity immunoglobulins from antibody rich colostrum and the possibility of compressing these colostral-antibodies into a tablet form without substantial loss of activity. Specific antibodies may be obtained by immunization of a mammal with specific antigens against enterotoxic bacteria such as E. coli, Salmonela and Shigella. WO 06/053383 by some of the inventors, describes a carboxylic acid and alkalizing moieties which confer upon a bioactive agent composition of a hyper immune colostrum, lactoferrin or lactoferracin, stability under a wide variety of gastric pH values. Finally, WO 03/080082 by some of the inventors describes a method of improving the viability of a labile bioactive substance, preferably immunoglobulins or fragments thereof or enzymes, in a gastric environment, comprising forming a mixture of the bioactive substance and mammalian colostrum and colostrums extracts. This conjugation protects the antibodies or antibodies fragments from the proteolysis occasioned by enzyme or low pH conditions and preserves their function in the stomach or rumen or other hostile environment.

The bowel mucosa is the largest lymphoid organ of the body. It deals with the dual role of nutrient absorption, while maintaining a physical and immunological barrier to the gut content. Despite constant antigenic stimulation, suppression of inflammation is the rule. Two key concepts pertain to the treatment of viral disease and its complications with colostrums: mucosal microbial translocation and enhanced immune regulation by oral feeding of disease antigens, termed "oral tolerance".

Increased mucosal microbial translocation: this is an immerging concept in disease pathogenesis. The higher levels of microbial translocation, quantified by the presence of LPS and bacterial DNA are central to a state of chronic immune activation accounting for immune exhaustion and autoimmune damage.

Stimulation through the bowel mucosa tends to elicit a tolerogenic immune response. This feature may be used advantageously to induce tolerance towards auto-antigens and in this way to suppress autoimmunity. Indeed, "oral tolerance" has been shown to effectively diminish the immune response towards orally fed antigens in different disease models [Safadi, R. et al. Am. J. Gastroenterol. 98(11): 2505-15 (2003)].

It has been previously shown that bovine-derived colostrum preparations can be used in treating toxin-mediated intestinal conditions. In a study of 10 volunteers challenged orally with a concentrate of enterotoxigenic E. coli, administration of a bovine antibody concentrate obtained by immunizing cows with the corresponding E. coli strains prevented the development of diarrhea in all 10 participants who received the product; by contrast, 9/10 controls developed diarrhea [Tacket, C. O. et al. N. Engl. J. Med. 318(19): 1240-3 (1988)]. In another study, the administration of milk-derived antibodies against the enterotoxigenic E. coli colonization factor protected 14/15 subjects from diarrhea, compared to 7/10 subjects given placebo [Freedman, D. J. et al. J. Infect. Dis. 177(3): 662-7 (1998)].

Another disease with a similar pathogenesis is pseudomembranous colitis. A study evaluated to effect of immune whey protein, obtained by immunizing cows with C. difficile inactivated toxins and whole-cell killed C. difficile shown as preventing relapse of C. difficile disease. Sixteen patients received the product after standard treatment for a confirmed episode of C. difficile colitis for two weeks. In all but one case, C. difficile toxin disappeared from the stool, and there were no recurrences after a median follow-up of 333 days [van Dissel, J. T. et al. J. Med. Microbiol. 54(2): 197-205 (2005)].

Collectively, these observations suggest that bovine-derived colostrum preparations deliver biologically active concentrations of specific antibodies to the intestinal lumen when taken orally, and might be capable of blocking various forms of bacterial toxins in the gut by that mechanism.

Since microbial translocation is driving immune activation and progression of liver disease, strategies that reduce or prevent microbial translocation may have a significant impact on immune activation, and thus on the natural history of chronic HCV infection. The present invention now demonstrates the use of bovine colostrum powder (BPC) preparations from immunized cows, containing high levels of antibodies, as immuno-modulators capable of reducing immune activation in response to microbial products such as LPS. Without being bound to any theory, the inventors hypothesize that the attachment of the BPC antibodies to the microbial antigens may prevent their translocation onto the blood stream, thereby restricting the immune response. These effects upon the immune system enable the use of such colostrum preparations for the treatment of infectious disease, which involve the immune system. More specifically, the present invention provides the use of a colostrum-derived preparation, comprising high concentrations of anti-LPS antibodies, in the treatment and amelioration of chronic liver diseases.

Microbial translocation is also associated with alteration of the liver inflammation in different liver disorders, including viral mediated, drug mediated, non alcoholic steatohepatitis and any other hepatic disorder. Microbial translocation may also be associated with insulin resistance, diabetes type 2, obesity and overweight. As shown by the invention, prevention of such translocation may be achieved using the anti-LPS enriched colostrum of the invention, optionally along with regulation of regulatory T cells, or any other component of the immune system, using a combination of the anti-LPS enriched colostrum with colostrum preparations enriched with antibodies recognizing disease-specific antigens, for example, anti-insulin enriched colostrum. Thus, the invention further provides compositions, combined compositions and methods for the treatment of any acute or chronic liver disease, diabetes and any complication associated therewith, fatty liver, non alcoholic steatohepatitis, and obesity.

It is therefore an object of the invention to provide the use of colostrum- or avian egg derived anti-LPS enriched immunoglobulin preparations in compositions and methods of treating, delaying or preventing the progression of chronic liver disease, cirrhosis and any complication or disorder associated therewith.

Another object of the invention is to provide combined compositions comprising a combination of anti-LPS antibodies enriched colostrum and antibodies recognizing at least one antigen specific for a pathologic disorder and uses thereof in the treatment of immune-related disorders.

These and other objects of the invention will become clearer as the description proceeds.

SUMMARY OF THE INVENTION

In one aspect, the present invention provides a composition comprising an anti-LPS enriched immunoglobulin preparation for use in treatment and/or prophylaxis of a pathologic disorder. The anti-LPS enriched immunoglobulin preparation may be derived from colostrum or from avian eggs.

In one embodiment, the pathologic disorder is acute or chronic liver disease, cirrhosis or any disease or complication associated therewith. In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness. In another embodiment, the pathologic disorder is liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder.

Alternatively, the pathologic disorder may be selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum or from avian eggs.

In one embodiment, the composition modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the composition modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment, the composition is for the treatment and/or prophylaxis of metabolic syndrome or non alcoholic steatohepatitis or both. In another embodiment, the composition is for the treatment, and/or prophylaxis of diabetes, the treatment of impaired glucose tolerance, such as decreasing glucose tolerance. decreasing serum insulin levels, decreasing hepatic triglyceride levels, or decreasing cholesterol levels.

In one embodiment, the composition modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders.

The composition may further comprise a therapeutic agent, carrier or adjuvant and/or non-hyperimmune colostrum.

The composition may be formulated for administration orally, by inhalation as an aerosol, or by parenteral, intravaginal, intranasal, mucosal, sublingual, topical, or rectal administration, or any combination thereof.

In one embodiment, the immunoglobulin preparation or any fractions thereof recognizes and binds LPS or any fragments thereof.

In another embodiment, the composition inhibits microbial translocation. In another embodiment the composition inhibits microbial translocation and thereby modulates immune activation.

In another aspect, the present invention provides a composition comprising a mammalian anti-LPS enriched colostrum-derived immunoglobulin preparation for modulating immune tolerance in a subject, or in another aspect, for modulating oral tolerance in a subject In another aspect, the present invention provides a composition comprising a mammalian anti-LPS enriched colostrum-derived immunoglobulin preparation for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ LAP+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP− T cells in the spleen, inducing CD4+ CD25+ LAP− T cells in adipose tissue.

The anti-LPS enriched immunoglobulin preparation may be derived from colostrum or from avian eggs.

In another aspect, the present invention provides a use of an anti-LPS enriched immunoglobulin preparation in the manufacture of a medicament for the treatment and/or prophylaxis of a pathologic disorder.

The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the medicament is for the treatment and/or prophylaxis of liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

The medicament may further comprise an immunoglobulin preparation comprising immunoglobulins that recognize and bind at least one antigen specific for said pathologic disorder. The further immunoglobulin preparation may be derived from colostrum or from avian eggs.

In one embodiment, the medicament modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the medicament modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment, the medicament is for the treatment and/or prophylaxis of metabolic syndrome or non alcoholic steatohepatitis or both, the treatment and/or prophylaxis of diabetes, the treatment impaired glucose tolerance, such as decreasing glucose tolerance, decreasing serum insulin levels, decreasing hepatic triglyceride levels, or decreasing cholesterol levels.

In one embodiment, the medicament modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders, The medicament may further comprise a therapeutic agent, carrier or adjuvant and/or non-hyperimmune colostrum.

In one embodiment, the medicament is formulated for administration orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment the composition reduces or inhibits mucosal microbial translocation and thereby modulates immune activation.

In another aspect, the present invention provided a use of a mammalian anti-LPS enriched colostrum-derived immunoglobulin preparation in the manufacture of a medicament for modulating immune tolerance in a subject, or in another embodiment, a medicament for modulating oral tolerance in a subject.

In another aspect, the present invention provides the use of a mammalian anti-LPS enriched colostrum-derived immunoglobulin preparation in the manufacture of a medicament for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP-T cells in the spleen, or inducing CD4+ CD25+ LAP− T cells in adipose tissue.

The anti-LPS enriched immunoglobulin preparation may be derived from colostrum or from avian eggs.

In one aspect, the present invention provides a method for the treatment and/or prophylaxis of a pathologic disorder comprising the step of administering to a subject in need thereof a therapeutically effective amount of a composition comprising an anti-LPS enriched immunoglobulin preparation. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the pathologic disorder is liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum or from avian eggs.

In another embodiment, the composition modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the composition modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment the pathologic disorder is metabolic syndrome or non alcoholic steatohepatitis or both.

In another embodiment, the pathologic disorder is diabetes. In another embodiment, the pathologic disorder is impaired glucose tolerance.

In another embodiment, the method decreases glucose tolerance, decreases serum insulin levels, decreases hepatic triglyceride levels, or decreases cholesterol levels.

In another embodiment, the method modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders, In another embodiment, the composition further comprises non-hyperimmune colostrum and/or a therapeutic agent, carrier or adjuvant.

The composition may be administered orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment, the method reduces or inhibits mucosal microbial translocation. In another embodiment, the method reduces or inhibits mucosa; microbial translocation and thereby modulates immune activation.

In another aspect, the present invention provides a method for modulating immune tolerance in a subject comprising the step of administering to a subject in need thereof a therapeutically effective amount of a composition comprising a mammalian anti-LPS enriched colostrum-derived immunoglobulin preparation. Alternatively, the method may be for modulating oral tolerance.

A method for inducing CD4+ CD25+ T cells in the liver of a subject comprising the step of administering to a subject in need thereof a therapeutically effective amount of a composition comprising a mammalian anti-LPS enriched colostrum-derived immunoglobulin preparation. In another embodiment, the method may be for inducing CD4+ CD25+ LAP− T cells in the liver, CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+NK1.1+ cells in the liver, decreasing CD25+ LAP− T cells in the liver, decreasing CD25+ LAP+ T cells in the liver, inducing CD4+ CD25+ LAP− T cells in the spleen, or inducing CD4+ CD25+ LAP− T cells in adipose tissue.

In another aspect, the present invention provides a composition for the treatment and prophylaxis of a pathologic disorder. The composition of the invention comprises as active ingredient a mammalian anti-lipopolysaccharide (anti-LPS) enriched colostrum-derived immunoglobulin preparation and optionally further colostrum, milk or milk product component's, and any adjuvant/s. The immunoglobulin preparation or any fractions thereof, recognizes and binds LPS and any fragments thereof. According to an optional embodiment, the composition of the invention may further comprises colostrum-derived immunoglobulin preparation recognizing at least one antigen specific for said disorder, thereby activating or inhibiting an immune response specifically directed toward said disorder. Such combined composition may optionally further comprises an additional therapeutic agent or any carrier and adjuvant.

Thus, according to one specific embodiment, the invention provides a composition comprising as an active ingredient a mammalian anti-lipopolysaccharide (LPS) enriched colostrum-derived immunoglobulin preparation. Such composition wherein said composition is particularly applicable for the treatment, prevention and prophylaxis of acute or chronic liver disease, cirrhosis and any disease or complication associated therewith, optionally said composition further comprises an additional therapeutic agent or any carrier and adjuvant.

According to another optional embodiment, the invention provides combined compositions comprising a combination of anti-LPS enriched immunoglobulin preparation with at least one colostrum- or avian-derived immunoglobulin preparation comprising immunoglobulins that recognize and bind at least one antigen specific for said pathologic disorder. Such combined composition may optionally further comprises an additional therapeutic agent or any carrier and adjuvant. These combined compositions may be used for treating any one of an autoimmune disease, non alcoholic steatohepatitis, fatty liver, atherosclerosis, metabolic syndrome and any disorder associated therewith such as diabetes type 2, insulin resistance, obesity and overweight.

In another aspect, the present invention provides the use of a mammalian anti-LPS enriched colostrum-derived immunoglobulin preparation and optionally of a colostrum-derived immunoglobulin preparation recognizing at least one antigen specific for a pathologic disorder in the manufacture of a composition for the treatment and prophylaxis of a pathologic disorder, It should be noted that the immunoglobulin preparation or any fractions thereof recognizes and binds LPS and any fragments thereof. According to an optional embodiment, the invention provides the use of the anti-LPS enriched immunoglobulin preparation of the invention furthering combination with at least one immunoglobulin preparation comprising immunoglobulins recognizing at least one antigen specific for said disorder. Such combined composition may be used as an immuno-modulatory composition that activates or inhibits an immune response specifically directed toward said disorder.

In a further aspect, the present invention provides a method for the treatment and/or prophylaxis of a pathologic disorder. The method of the invention comprises the step of administering to a subject in need thereof a therapeutically effective amount of a mammalian colostrum-derived anti-LPS enriched immunoglobulin preparation or of a composition comprising the same. It should be noted that the immunoglobulin preparation or any fractions thereof recognizes and binds LPS and any fragments thereof. Such method may be used for the treatment, prevention and prophylaxis of acute or chronic liver disease, cirrhosis and any disease or complication associated therewith. According to an optional embodiment, the anti-LPS enriched immunoglobulin preparation of the invention may be further combined with at least one immunoglobulins recognizing at least one antigen specific for said disorder, thereby activating or inhibiting an immune response specifically directed toward said disorder. This method may be specifically applicable for treating immune-related disorders. It should be particularly appreciated that the compositions and combined compositions used by the methods of the invention may be also applicable for treating any one of non alcoholic steatohepatitis, fatty liver, atherosclerosis, metabolic syndrome and any disorder associated therewith such as diabetes type 2, insulin resistance, obesity and overweight.

Values are mean±SD. AST; aspartic transaminase, and ALT; alanine aminotransferase.

FIG. 2: Oral anti-LPS enriched colostrum-derived immunoglobulin preparation increases the expression of CD4+CD25+ regulatory T cells in the liver.

A; average surface expression of markers on lymphocytes. Values are mean±SD. B; A representative dot blot derived from PACS analysis.

Figure 3A:
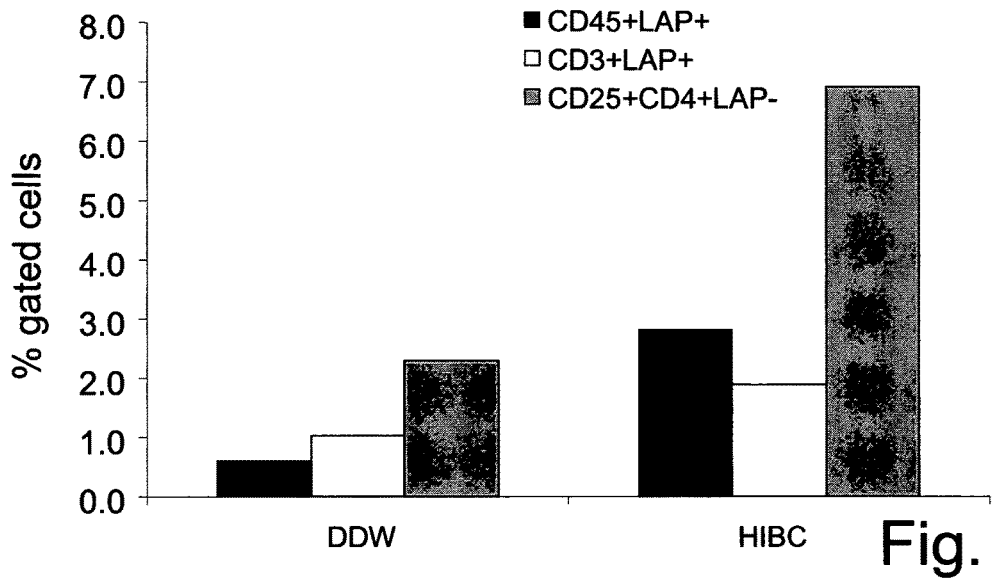
Figure 3B:
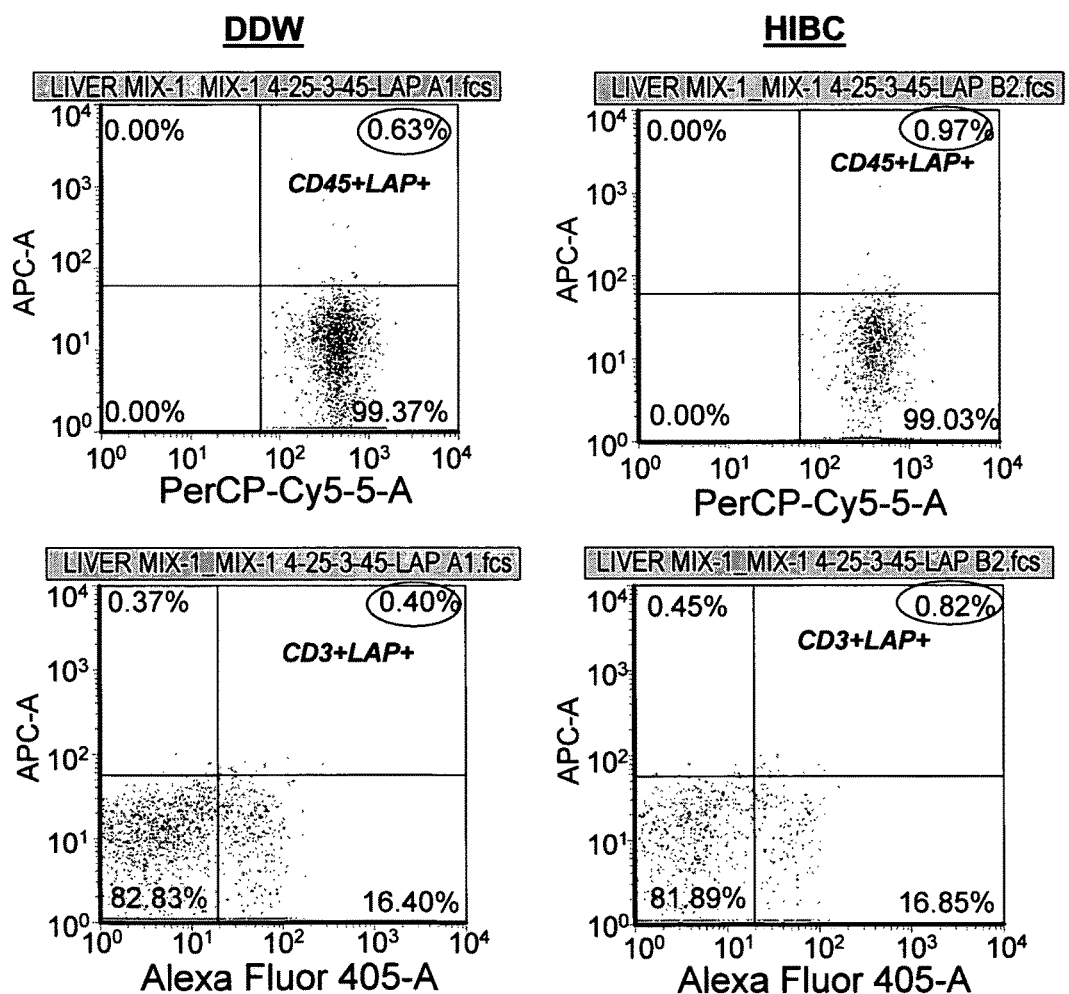

FIG. 3: Oral anti-LPS enriched colostrum-derived immunoglobulin preparation increases the expression of CD25+CD4+LAP−, CD45+LAP+ and CD3+LAP+ regulatory T cells in the liver. Values are means.

A; average surface expression of markers on lymphocytes. B; A representative dot blot derived from FACS analysis.

Figure 4A:
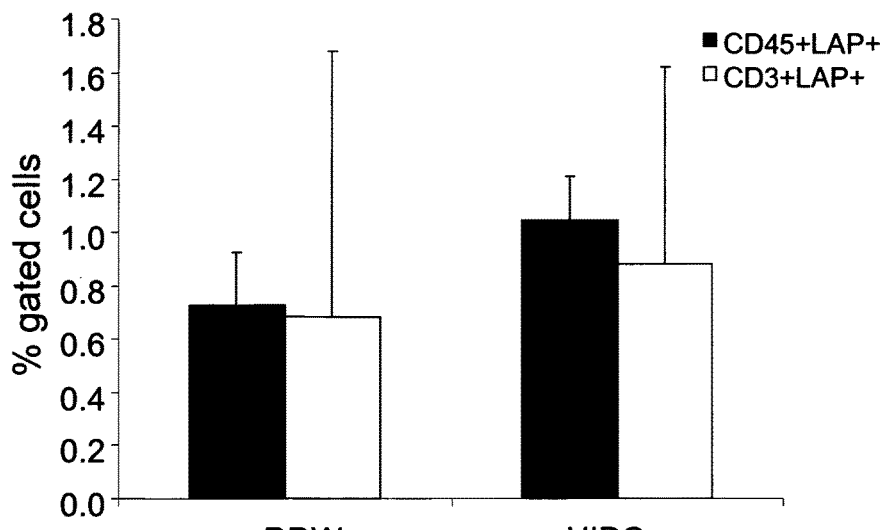
Figure 4B:
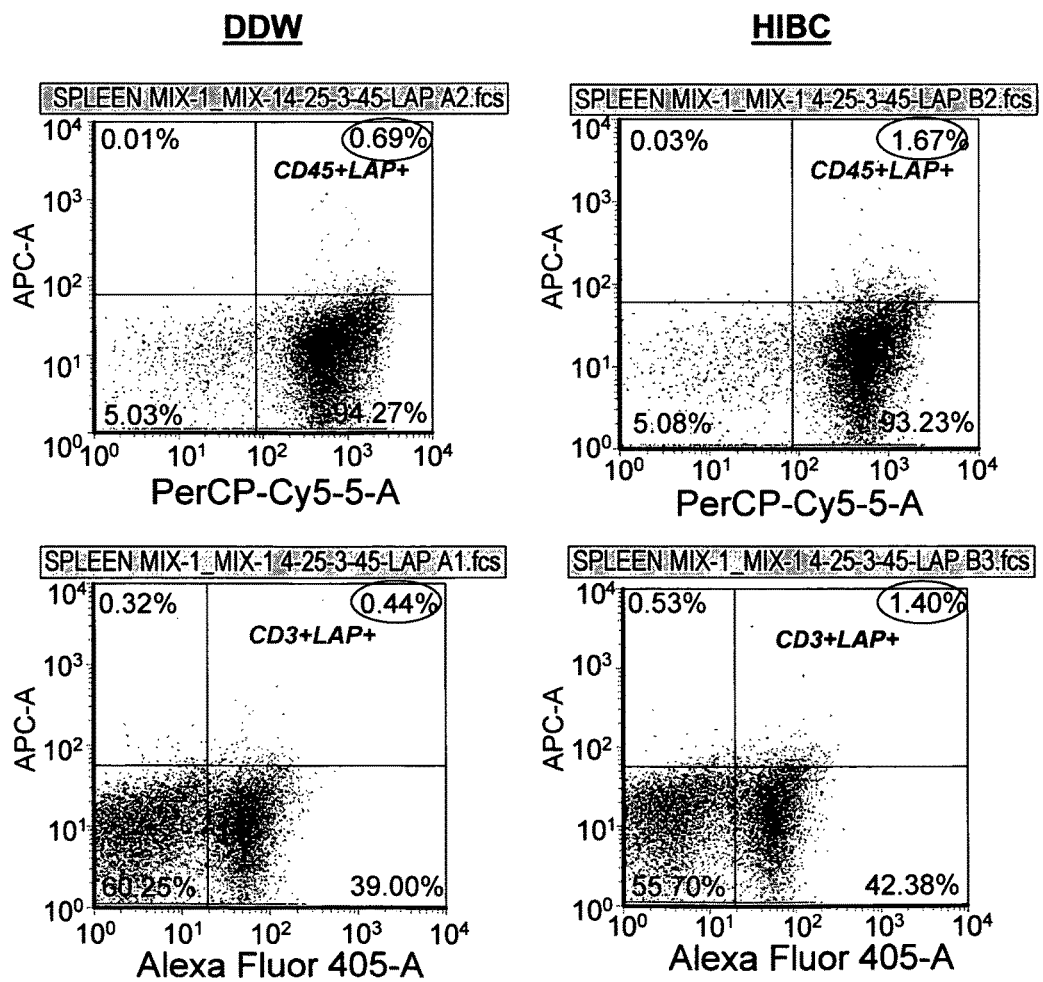

FIG. 4: Oral anti-LPS enriched colostrum-derived immunoglobulin preparation increases the expression of CD45+LAP+ and CD8+LAP+ regulatory T cells in the spleen.

A; average surface expression of markers on lymphocytes. Values are mean±SD. B; A representative dot blot derived from FACS analysis.

Figure 5:
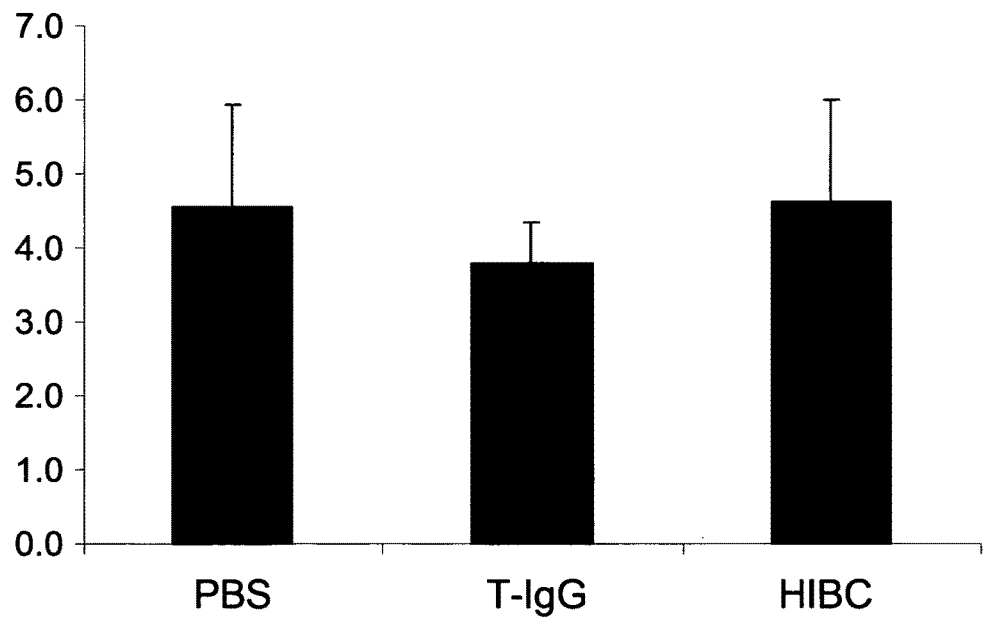

FIG. 5: Oral T-IgG-Colostrum decreases serum insulin in Ob/Ob mice

Values are mean±SD

Figure 6:
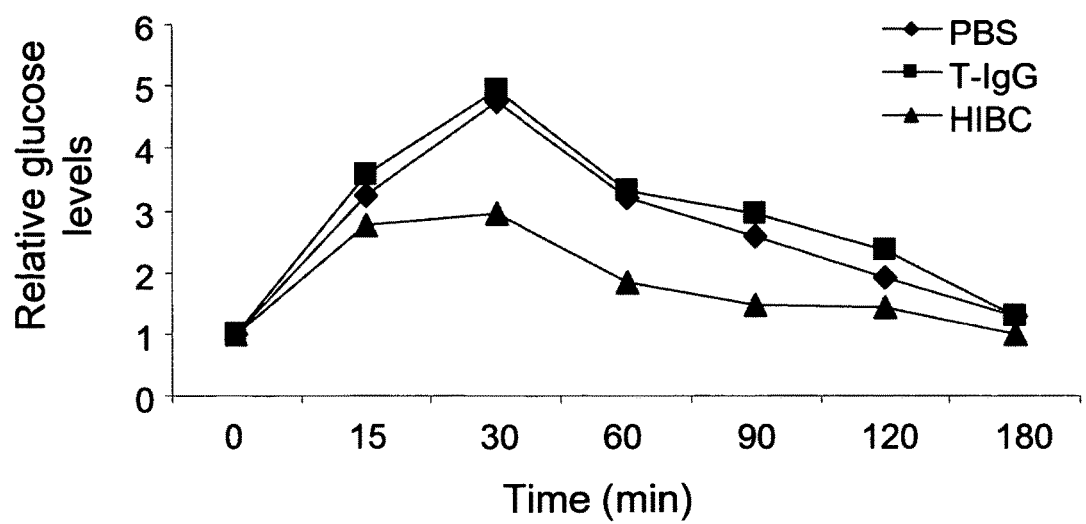

FIG. 6: Oral anti-LPS enriched colostrum-derived immunoglobulin preparation decreases glucose tolerance in Ob/Ob mice.

Figure 7:
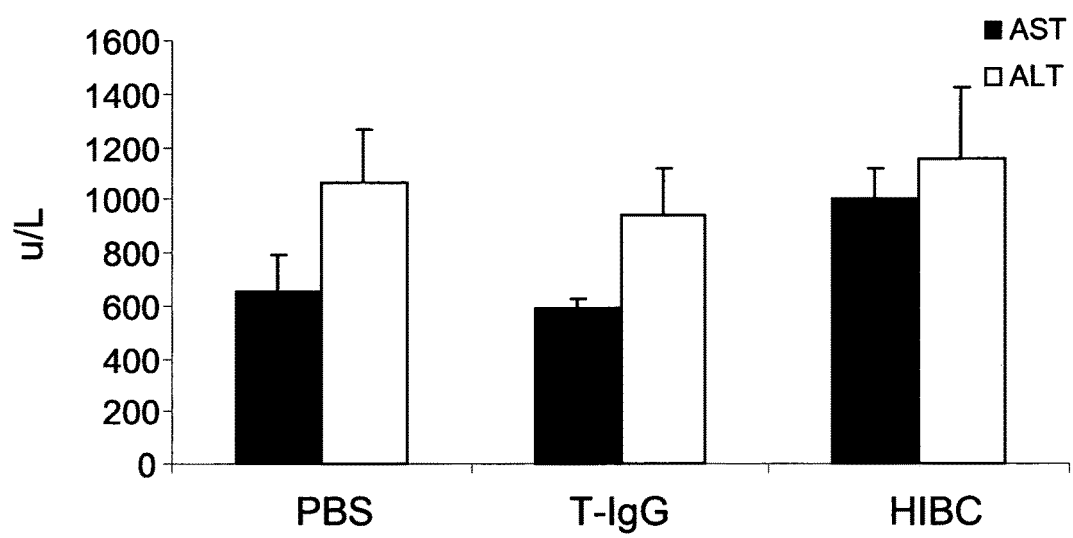

FIG. 7: Oral administration of anti-LPS enriched colostrum-derived immunoglobulin preparation decreases liver injury in Ob/Ob mice.

Values are mean±SD. AST; aspartic transaminase, and ALT; alanine aminotransferase.

Figure 8:
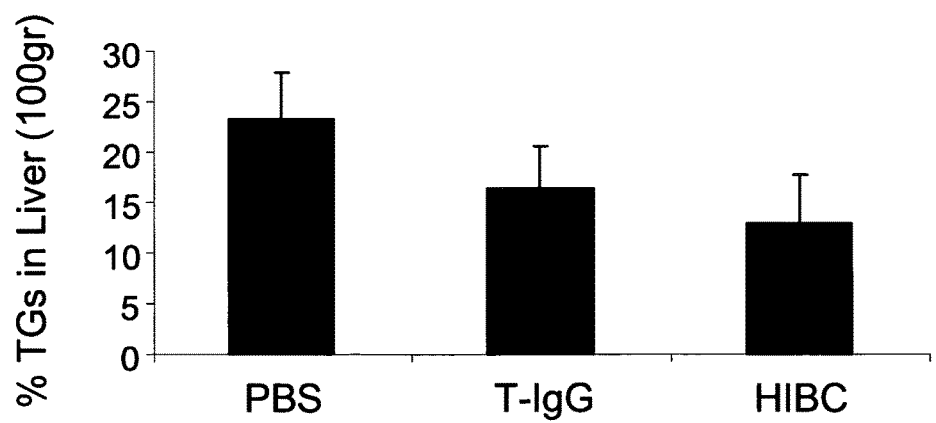

FIG. 8: Oral administration of anti-LPS enriched colostrum-derived immunoglobulin preparation decreases hepatic triglycerides (TGs) in Ob/Ob mice.

Values are mean±SD

Figure 9A:
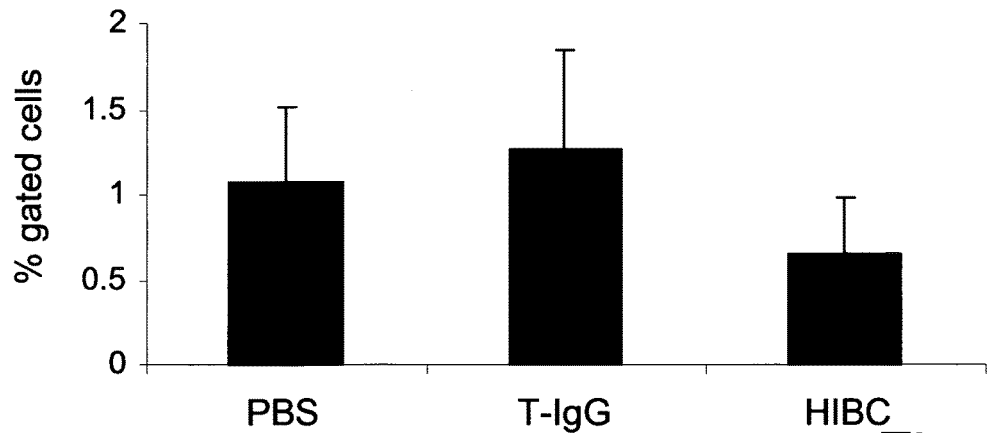
Figure 9B:
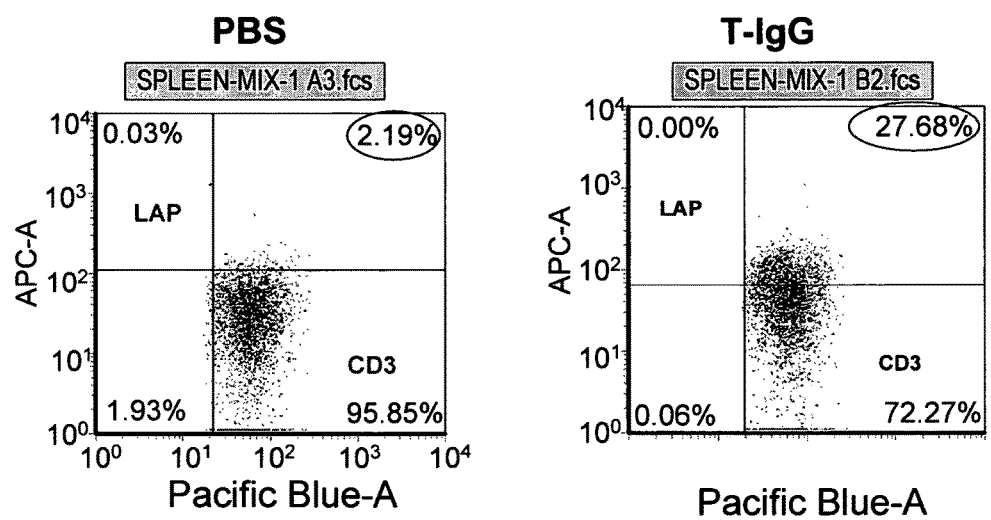
Figure 9B:
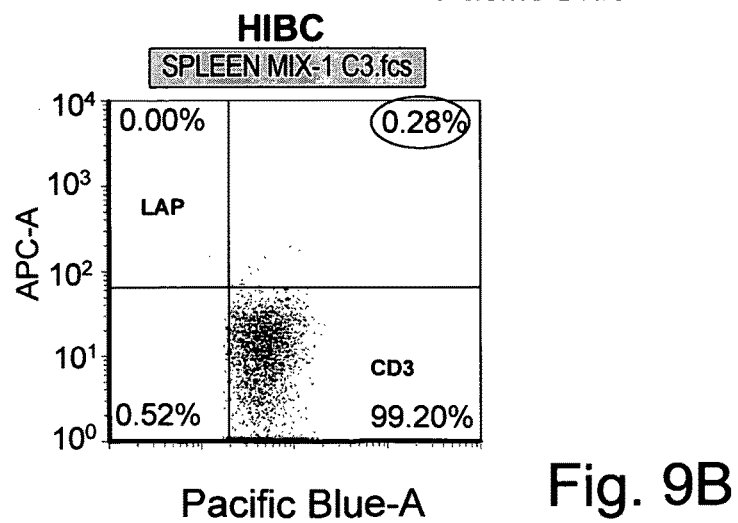

FIG. 9: Oral administration of anti-LPS enriched colostrum-derived immunoglobulin preparation increases the expression of CD3+LAP+ regulatory T cells in the spleen A; average surface expression of markers on lymphocytes. Values are mean±SD. B; A representative dot blot derived from FACS analysis.

Figure 10:
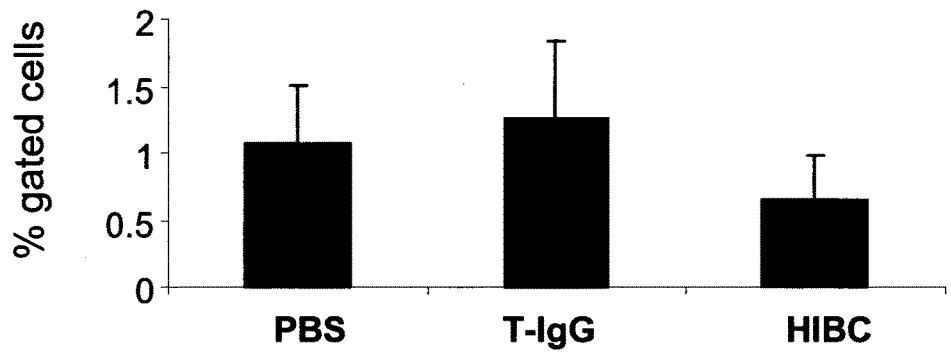

FIG. 10: Oral administration of anti-LPS enriched colostrum-derived immunoglobulin preparation increases the expression of CD8+CD25+ regulatory T cells in the spleen.

Values are mean±SD

Figure 11:
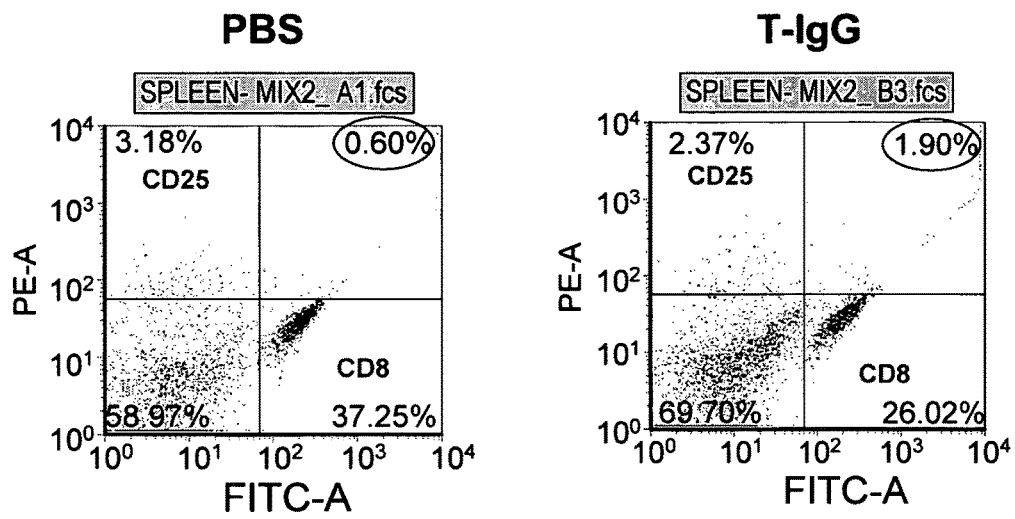
Figure 11:
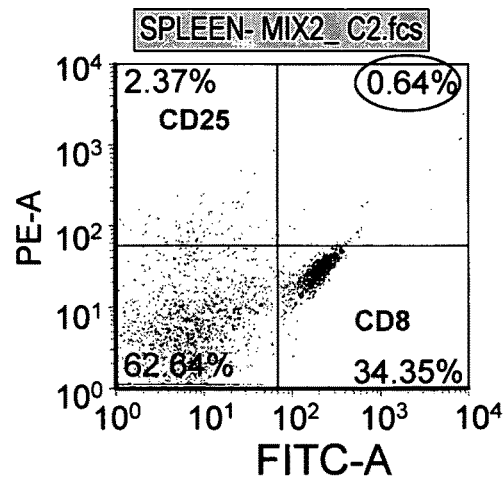

FIG. 11: Oral administration of anti-LPS enriched colostrum-derived immunoglobulin preparation increases the expression of CD8+CD25+ regulatory T cells in the spleen.

A representative dot blot derived from FACS analysis.

FIG. 12: Oral anti-LPS enriched colostrum-derived immunoglobulin preparation increases the expression of CD4+CD25+ regulatory T cells in adipose tissue.

A; average surface expression of markers on lymphocytes. Values are mean±SD. B; A representative dot blot derived from FACS analysis.

Figure 13A:
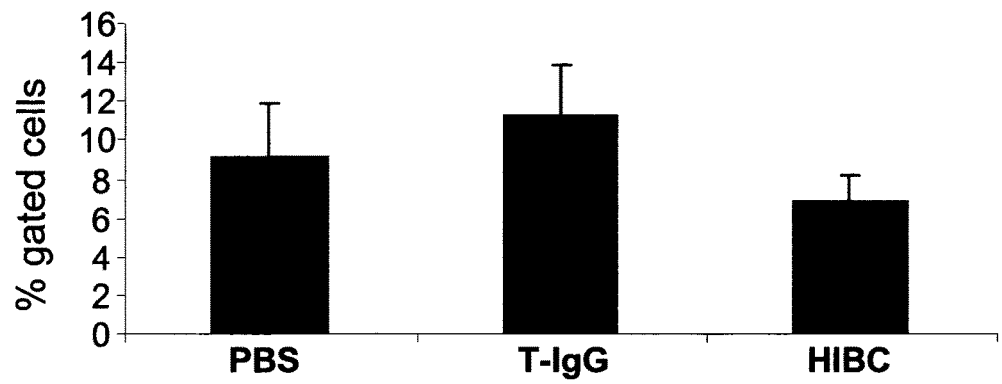
Figure 13B:
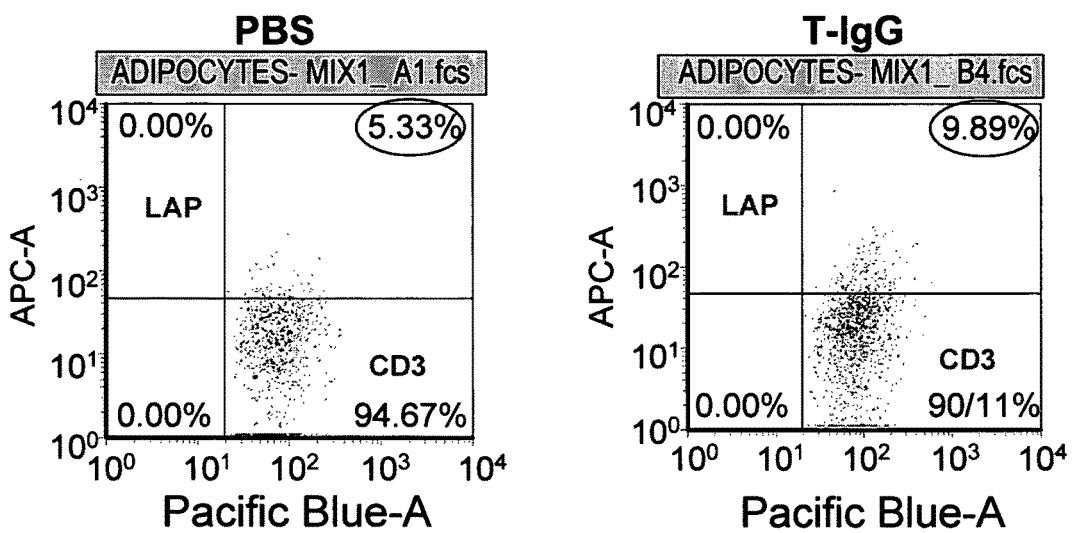
Figure 13B:
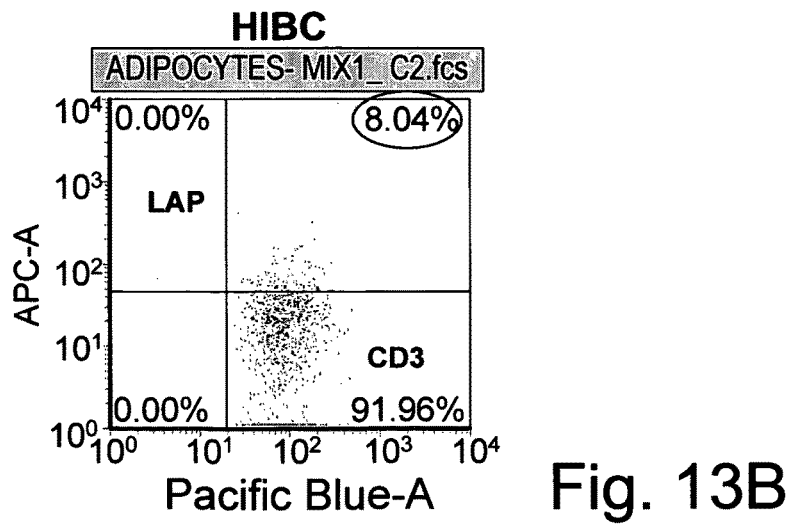

FIG. 13. Oral anti-LPS enriched colostrum-derived immunoglobulin preparation increases the expression of CD3+LAP+ regulatory T cells in adipose tissue A; average surface expression of markers on lymphocytes. Values are mean±SD. B; A representative dot blot derived from FACS analysis.

Figure 14A:
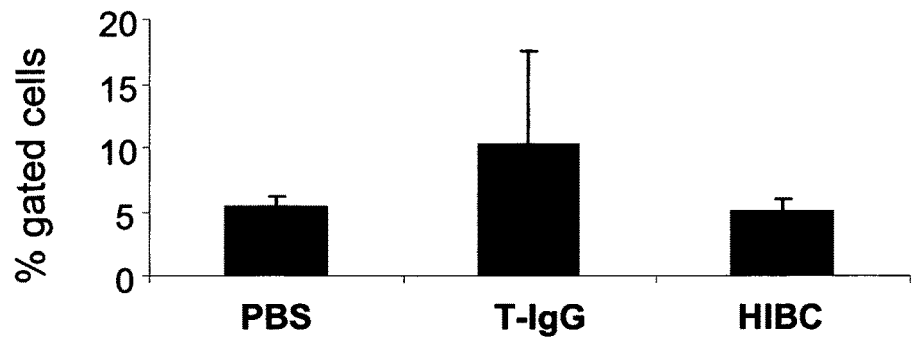
Figure 14B:
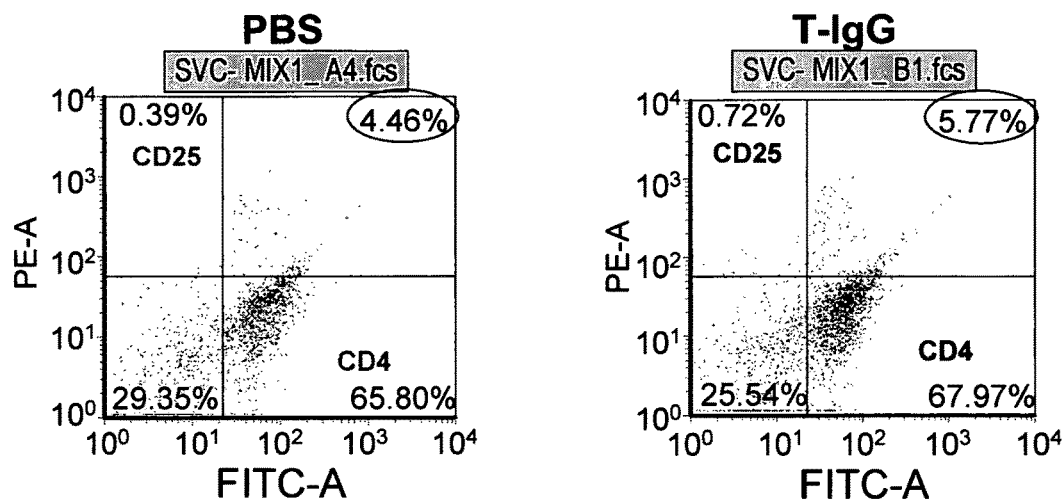
Figure 14B:
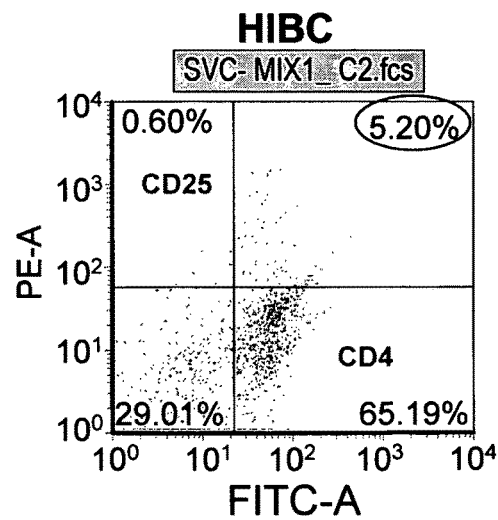

FIG. 14: Oral anti-LPS enriched colostrum-derived immunoglobulin preparation increases the expression of CD4+CD25+ regulatory T cells in Stromal Vascular Cells (containing preadipocytes)

A; average surface expression of markers on lymphocytes. Values are mean±SD. B; A representative dot blot derived from FACS analysis.

FIG. 15: Oral anti-LPS enriched colostrum-derived immunoglobulin preparation increases the expression of CD4+CD25+LAP+ lymphocytes in Stromal Vascular Cells (containing preadipocytes).

A; average surface expression of markers on lymphocytes. Values are mean±SD. B; A representative dot blot derived from FACS analysis.

Figure 16:
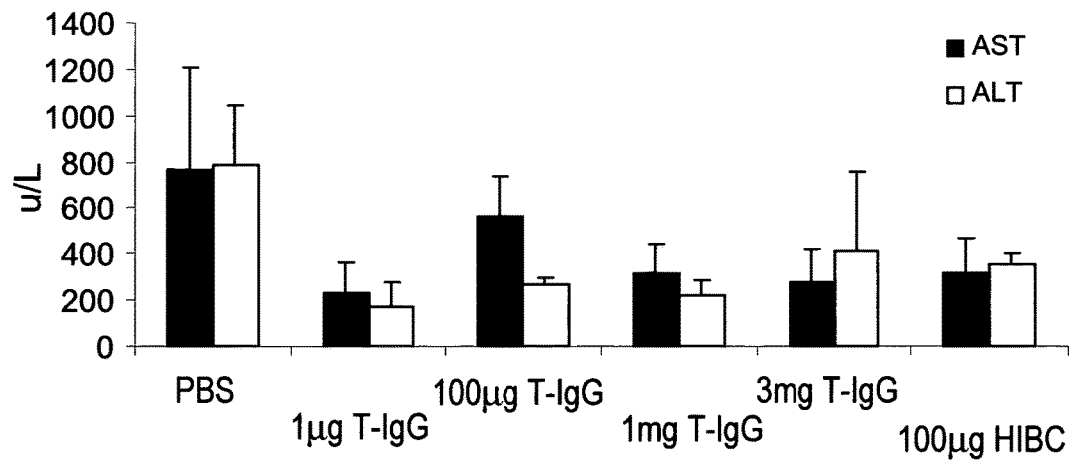

FIG. 16: Oral anti-LPS enriched colostrum-derived immunoglobulin preparation decreases liver enzymes in Ob/Ob mice.

Values are mean±SD. AST; aspartic transaminase, and ALT; alanine aminotransferase.

Figure 17:
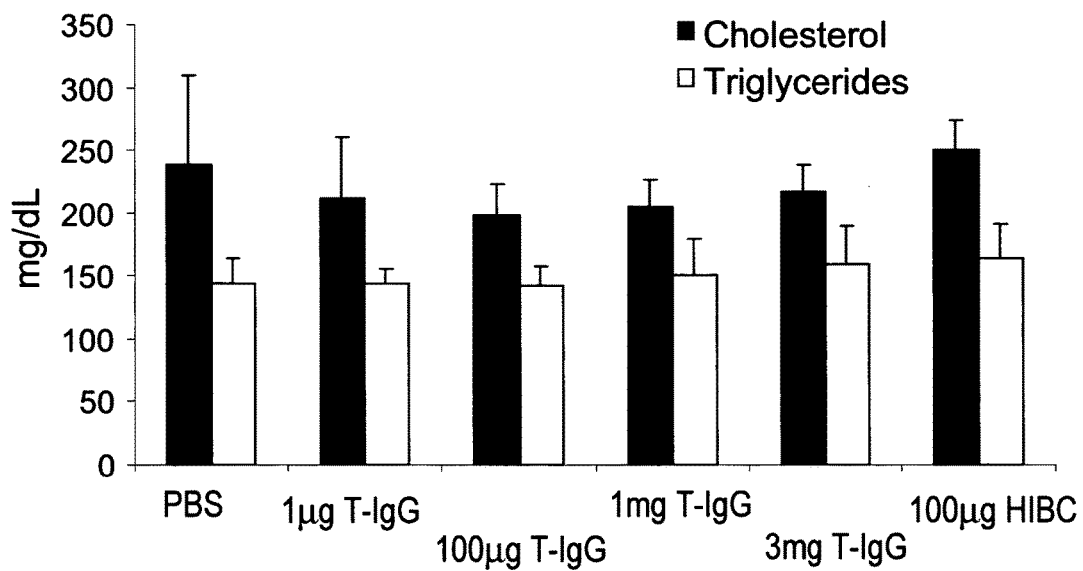

FIG. 17: Oral anti-LPS enriched colostrum-derived immunoglobulin preparation decreases total cholesterol in Ob/Ob mice.

Values are mean±SD.

Figure 18:
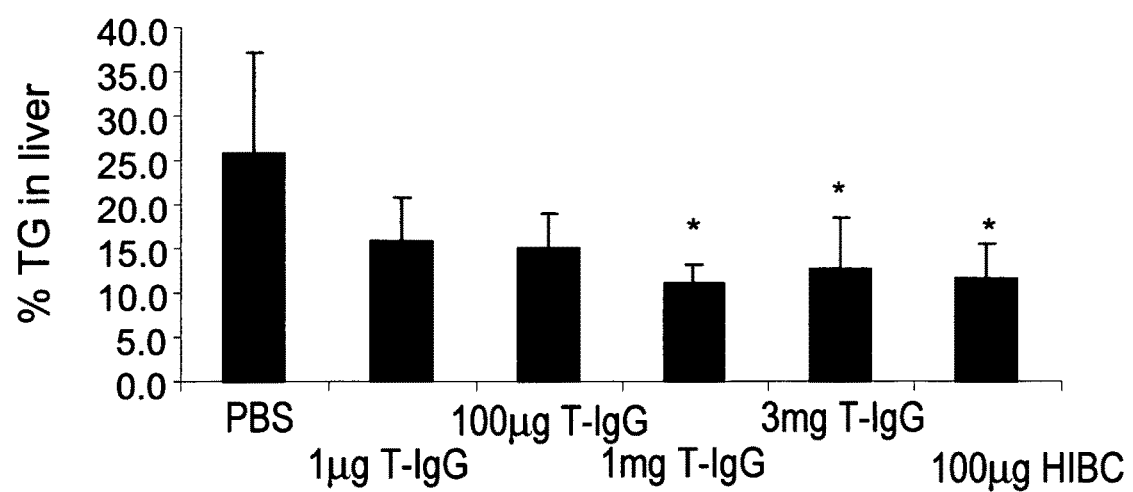

FIG. 18: Oral anti-LPS enriched colostrum-derived immunoglobulin preparation decreases hepatic TGs in Ob/Ob mice.

Oral administration of T-IgG and HIBC colostrums decreases hepatic TGs in Ob/Ob mice. Values are mean±SD. The decrease was significant for group A versus D, E, F (* $p<0.05$).

Figure 19A:
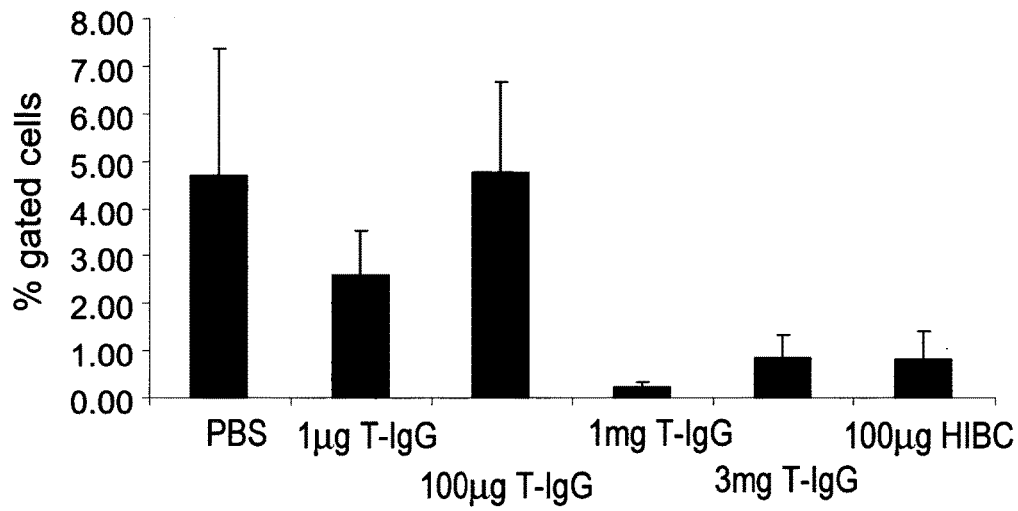
Figure 19B:
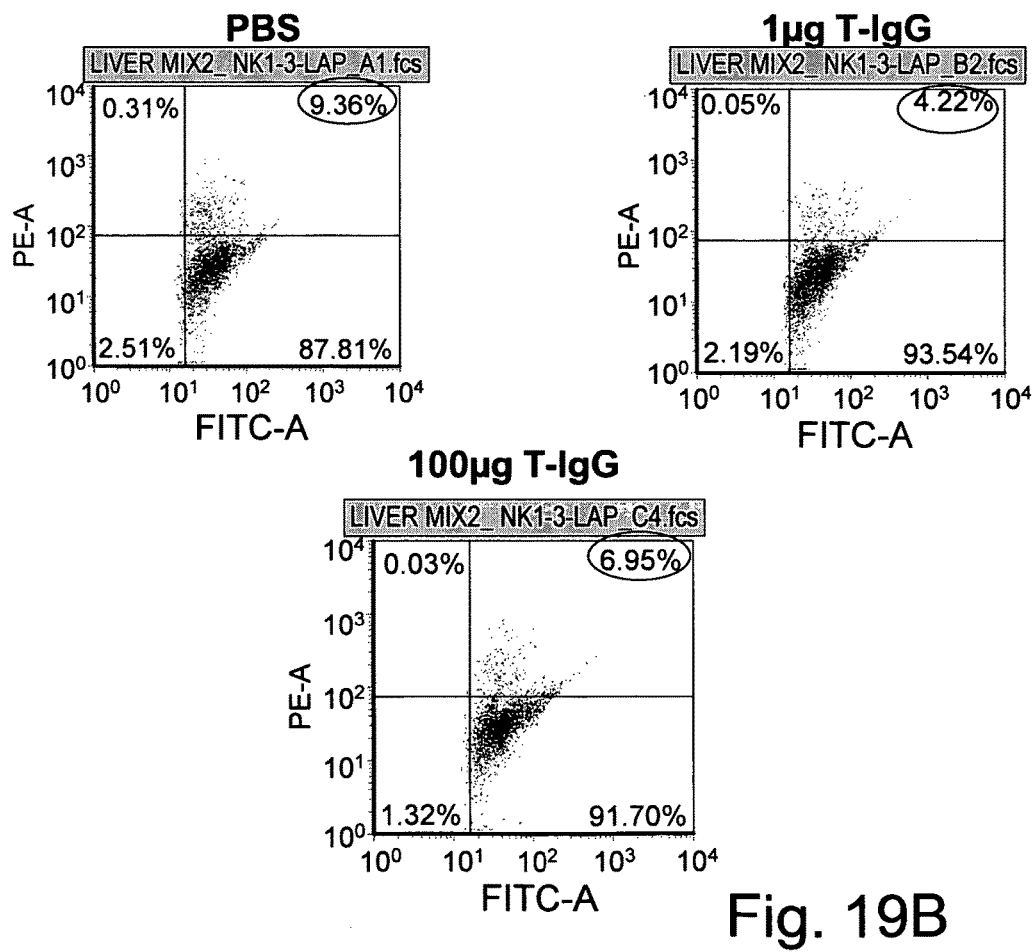

FIG. 19: Oral anti-LPS enriched colostrum-derived immunoglobulin preparation decreased CD3+NK1.1+ cells in the livers of Ob/Ob mice A. Oral administration of 1 ug, 1 mg, 3 mg of T-IgG, along with 100 ug HIBC, decreased CD3+NK1.1+ cells in the livers of Ob/Ob mice. Average surface expression of markers on lymphocytes. Values are mean±SD. B: Oral administration of 1 ug and 100 ug of T-IgG, decreased CD3+NK1.1+ cells in the livers of Ob/Ob mice. A representative dot blot derived from FACS analysis.

Figure 20A:
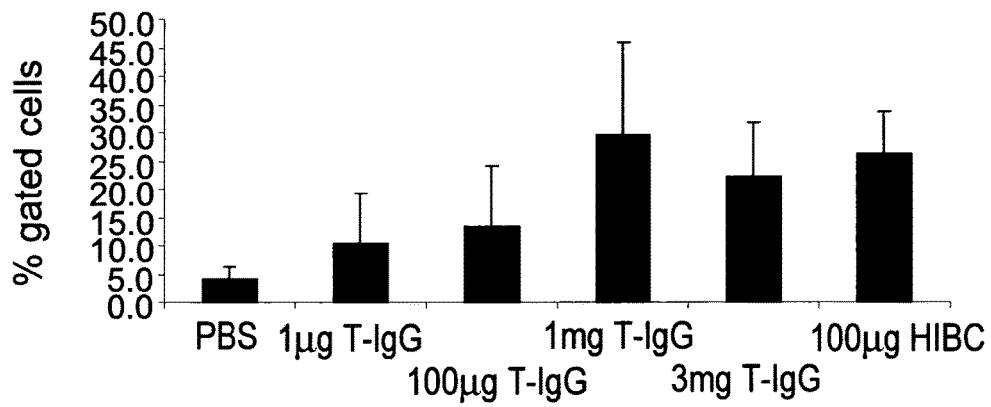
Figure 20A:
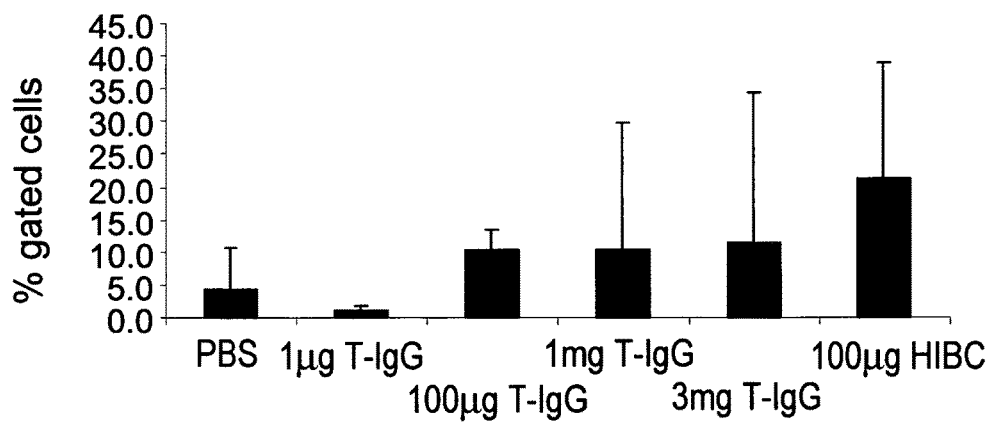

FIG. 20: Oral anti-LPS enriched colostrum-derived immunoglobulin preparation increases CD4+CD25+LAP−/LAP+ cells in the livers of Ob/Ob mice A; average surface expression of markers on lymphocytes. Values are mean±SD. B; A representative dot blot derived from FACS analysis.

Figure 21:
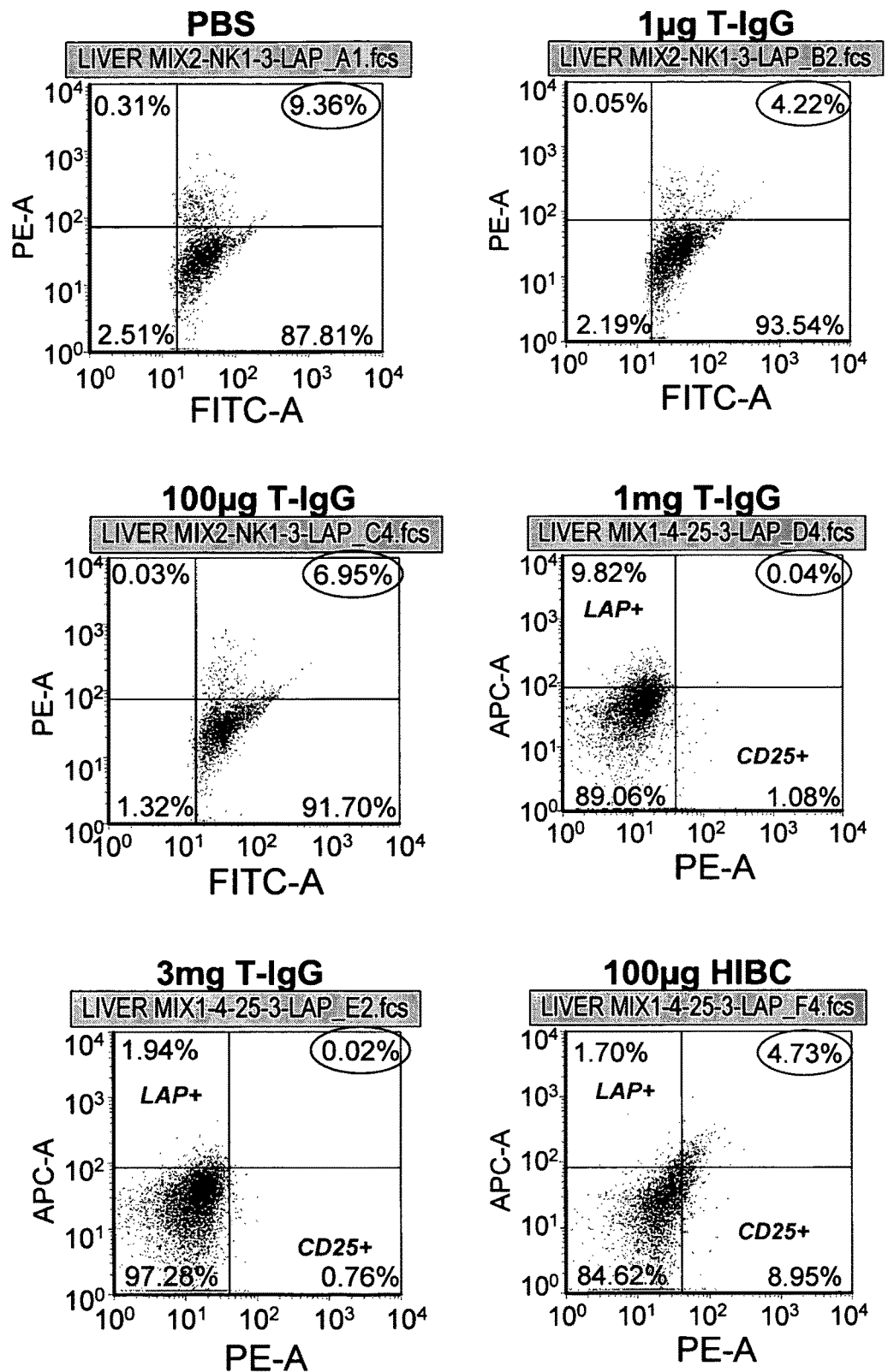

FIG. 21: Oral anti-LPS enriched colostrum-derived immunoglobulin preparation induces changes in CD25+LAP− hepatic lymphocytes.

Oral administration of T-IgG and of HIBC-colostrums, induces changes in CD25+LAP− hepatic lymphocytes. A representative dot blot derived from FACS analysis.

Figure 22A:
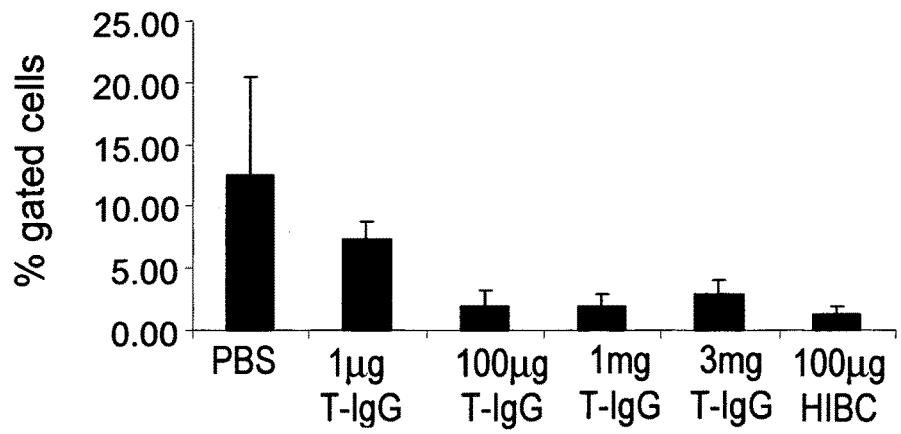

FIG. 22: Oral anti-LPS enriched colostrum-derived immunoglobulin preparation decreases CD25+LAP+ splenic lymphocytes.

A. Oral administration of T-IgG and of HIBC-colostrums, decreases CD25+LAP+ splenic lymphocytes. Average surface expression of markers on lymphocytes. Values are mean±SD. B: A representative dot blot derived from FACS analysis.

Figure 23:
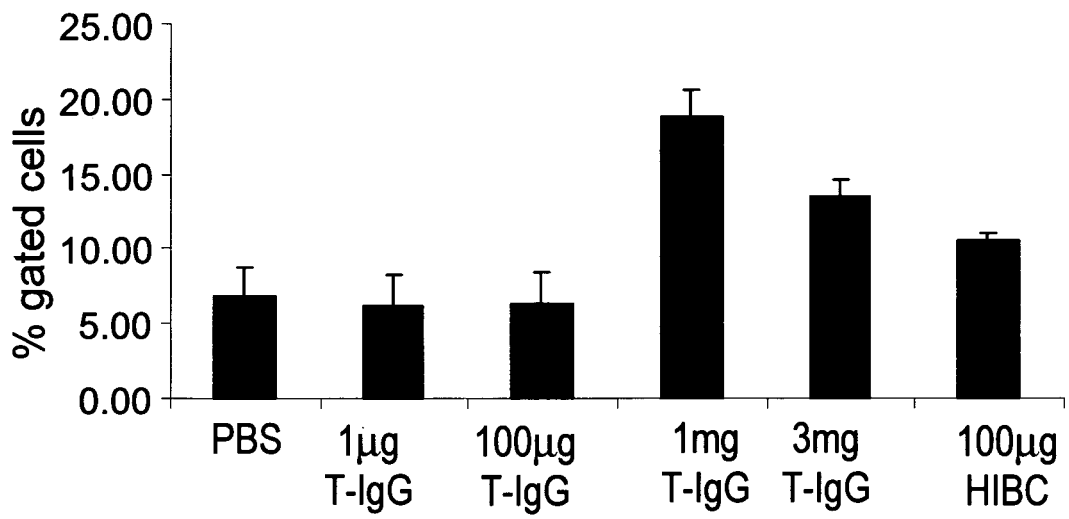

FIG. 23: Oral anti-LPS enriched colostrum-derived immunoglobulin preparation increases CD4+CD25+LAP− splenic lymphocytes A. Oral administration of 1 and 3 mg of T-IgG and of 100 mg of HIBC-colostrums, increases CD4+CD25+LAP− splenic lymphocytes FIG. 24: Oral anti-LPS enriched colostrum-derived immunoglobulin preparation increases CD4+CD25+ in adipose tissue.

A. Oral administration of T-IgG-colostrums, increases CD4+CD25+ in adipose tissue. Average surface expression of markers on lymphocytes. Values are mean±SD.

Figure 25A:
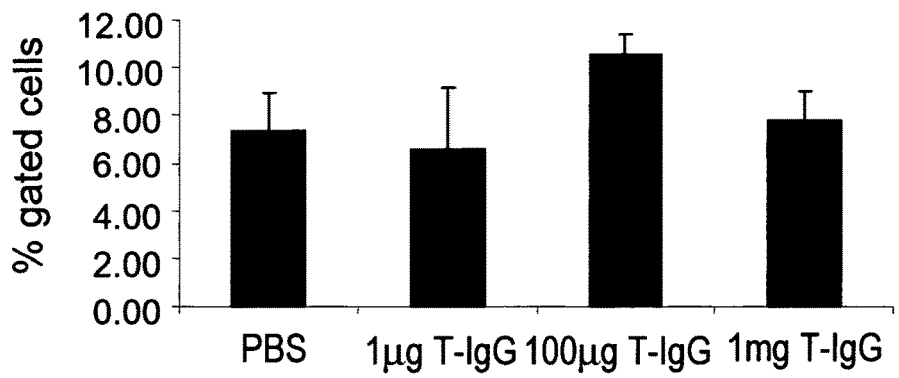
Figure 25B:
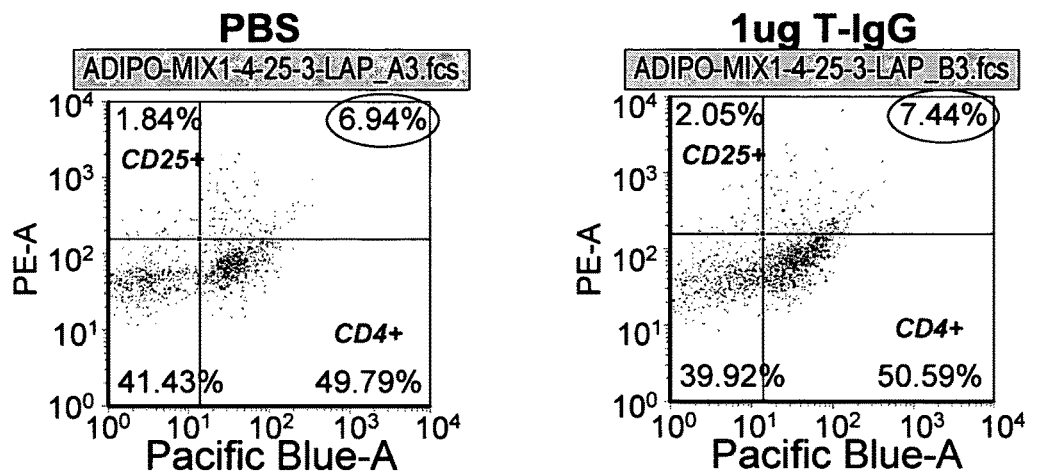
Figure 25B:
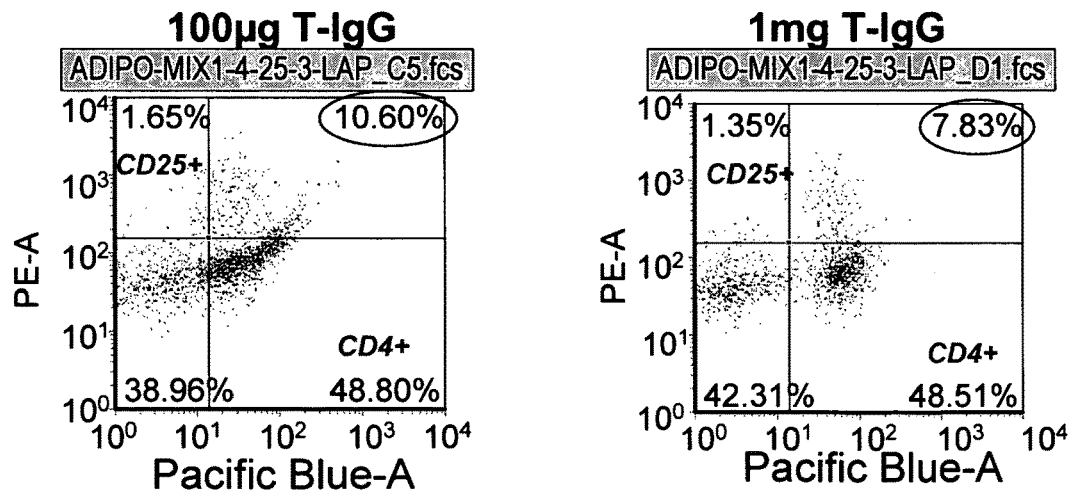

FIG. 25: Oral anti-LPS enriched colostrum-derived immunoglobulin preparation increases CD4+CD25+ in adipocytes.

A. Oral administration of 100 mg of T-IgG-colostrum, increases CD4+CD25+ in adipocytes. Average surface expression of markers on lymphocytes. Values are mean±SD. B. Oral administration of 1 ug, 100 mg and 1 mg of T-IgG-colostrum, increases CD4+CD25+ in adipocytes. A representative dot blot derived from FACS analysis.

Figure 26A:
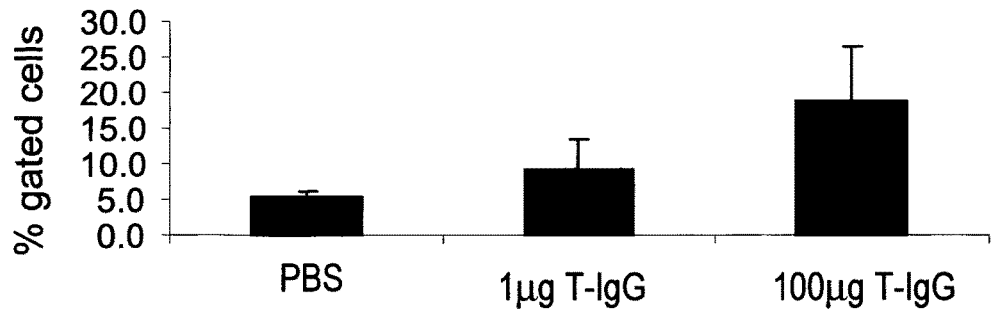
Figure 26B:
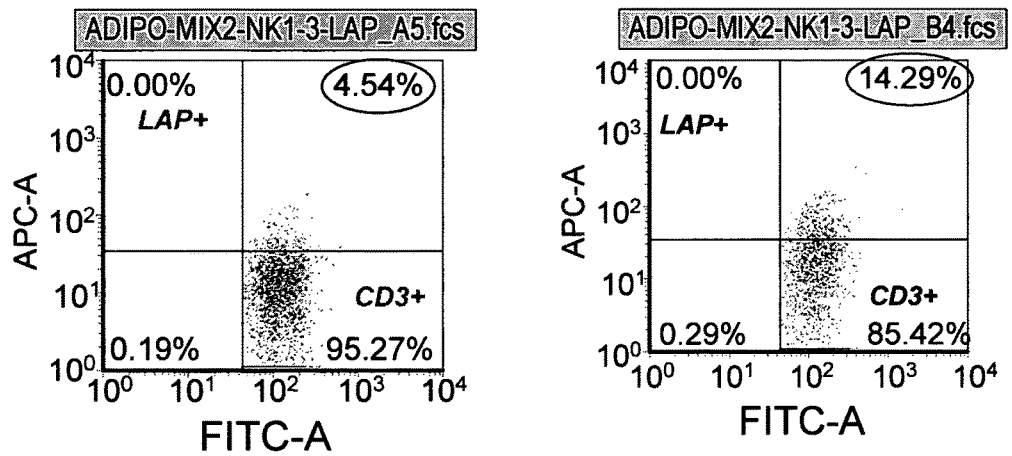
Figure 26B:
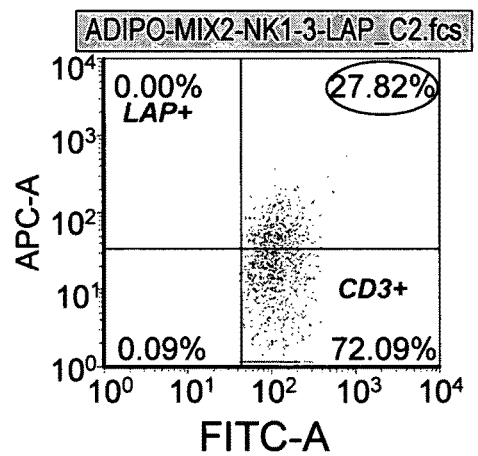

FIG. 26: Oral anti-LPS enriched colostrum-derived immunoglobulin preparation increases CD3+LAP+ in adipocytes A. Oral administration of T-IgG-colostrum, increases CD3+LAP+ in adipocytes. Average surface expression of markers on lymphocytes. Values are mean±SD. B: A representative dot blot derived from FACS analysis.

Figure 27A:
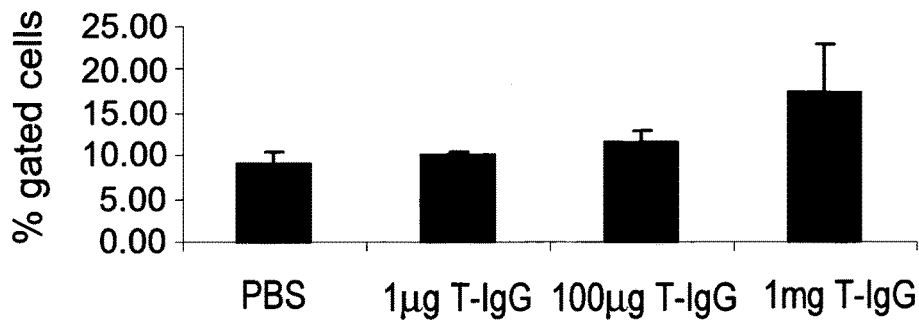
Figure 27B:
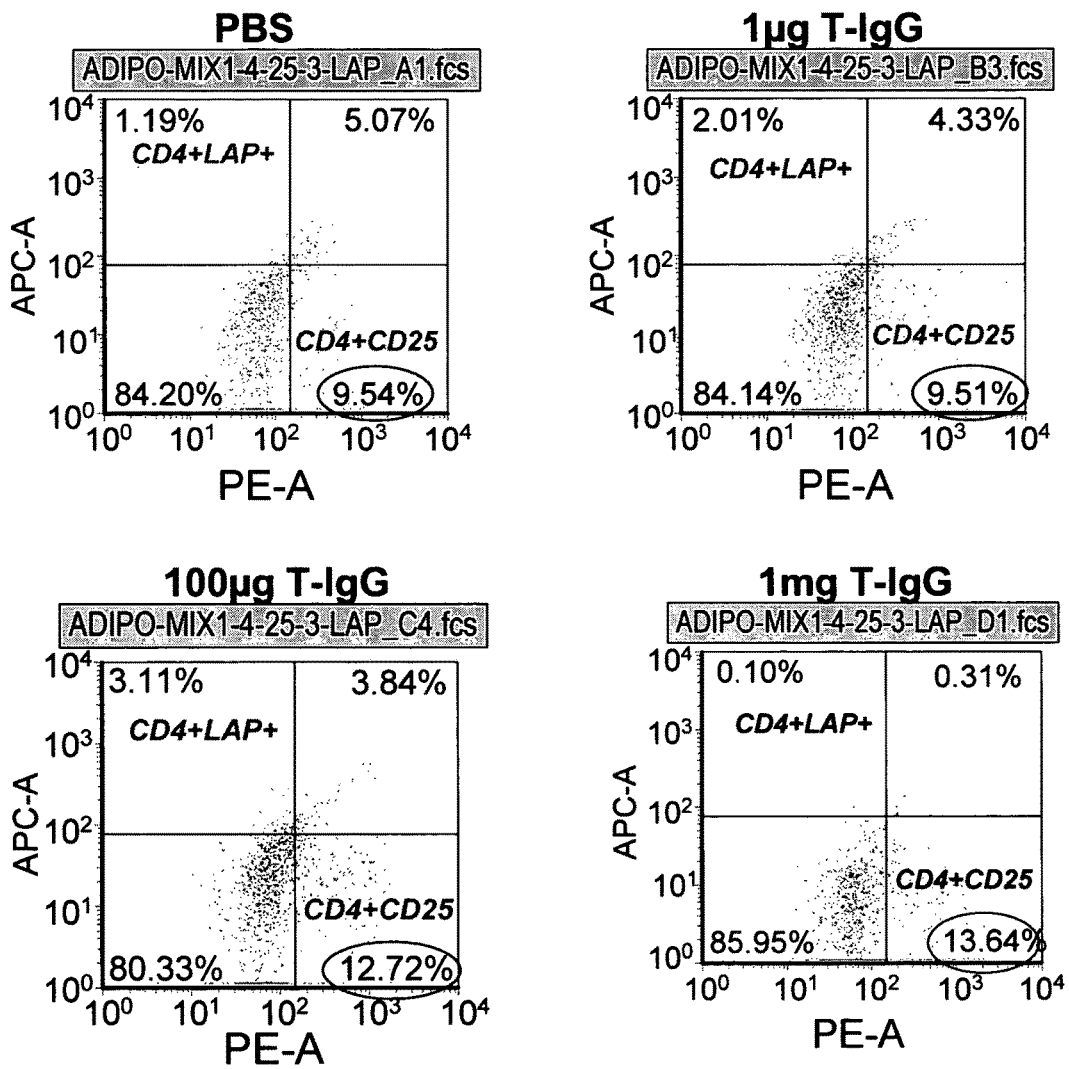

FIGS. 27A-B: Oral anti-LPS enriched colostrum-derived immunoglobulin preparation increases CD4+CD25+LAP− in adipocytes.

DETAILED DESCRIPTION OF THE INVENTION

A productive immune response results from the effective integration of positive and negative signals that have an impact on both innate and adaptive immune cells. When positive signals dominate, cell activation and pro-inflammatory responses ensue, resulting in the elimination of pathogenic microorganisms, viruses as well a transformed cell. In the absence of such productive stimulation, cell activation is blocked and active anti-inflammatory responses can occur. Modulation of this binary system occurs through the action of cytokines, downstream signaling pathways and cell-cell contact. The perturbation of these thresholds can result in aberrant responses that are either insufficient to deal with pathogenic microorganisms or result in the loss of tolerance and the induction of autoimmune responses. The present invention shows an immunomodulatory effect of a colostrum-derived immunoglobulin preparation enriched in anti-lipopolysaccharide (LPS) antibodies that may act in an active manner for the treatment of immune-related disorders.

Regulatory T cells (Tregs) are increasingly recognized as an important immunomodulatory component of the adaptive immune system. Immune dysregulation may lead to chronic inflammation as a trigger for chronic insulin insensitivity. The present invention shows in a particular example, that oral administration of colostrum-derived anti-LPS antibodies promote Tregs in adipose tissue and in adipose tissue associated stromal vasculature. These alterations are associated with alleviation of the Metabolic Syndrome and liver injury in the ob/ob mice model. Therefore, the present invention provides as a novel therapeutic composition for the alleviation and treatment of the Metabolic Syndrome.

The present inventors have shown that orally administered anti-LPS antibodies promoted Tregs in the liver, spleen, adipose tissue and SV (stromal-vascular cells). CD25+ LAP+ T cells, CD4+ CD25+ T cells, 004+ CD25+ LAP− T cells, CD45+ LAP+ T and CD3+ LAP+ T cells are induced in the liver. CD45+ LAP+ T cells, CD8+ LAP+ T cells, CD3+ LAP+ T, CD8+ CD25+ T cells are induced in the spleen. 004+ CD25+ T cells, CD3+ LAP+ T cells, CD4+ CD25+ LAP− T cells are induced in adipose tissue. CD4+ CD25+ T cells and CD4+ CD25+ LAP+ T cells are induced in stromal vascular cells, CD3+NK1.1+ cells in the liver, and CD25+ LAP− T cells are decreased in the liver.

Various constituents of the adipose tissue, such as mature adipocytes and stromal vascular cells, have distinct functions. They express and secrete different kinds of bioactive molecules collectively called adipokines. Altered adipokine secretion patterns characterize obesity and insulin resistance, which are major risk factors for type 2 diabetes mellitus. Regional and genotypic differences are present in stromal-vascular cells from obese and lean Zucker rats [Turkenkopf, I. J. et al. Int. J. Obes. 12:515-24 (1988)]. Gene expression profiling using DNA microarrays showed differences between adipose tissue, adipocytes, and stromal vascular cells [Permana (2008) ibid.]. The present invention further supports this notion, showing that the distribution of Tregs in these tissues is important in the metabolic syndrome and liver diseases.

The invention further shows that the promotion of Tregs in the adipose tissue and SV by administration of anti-LPS antibodies is associated with insulin resistance alleviation. This is demonstrated by glucose tolerance tests. In addition, the inflammatory liver damage is alleviated by the present invention, as manifested by a decrease in liver enzymes.

As described above, the invention shows that oral administration of colostrum-enriched with anti-LPS antibodies can serve as a mean to promote Tregs in the adipose tissue and the adipose tissue associated stromal vasculature.

The invention also presents synergy between colostrum-derived components and anti-LPS antibodies by the effect on the distribution of Tregs. Several proteins were identified in breast milk as involved in host defense [Kahn, S. E. et al. Nature 444:840-6 (2006)], including high concentrations mediators of the innate immune system [Poggi, M. et al. Diabetologia (2009)]. Among these mediators are multiple defensin proteins, sphingolipids, osteopontin, exosomes, TLRs, cathelicidin, ^ eosinophil-derived neurotoxin, and high-mobility group box protein 1, and LL-37 [Poggi (2009) ibid.; Nagatomo, T. et al. Clin. Exp. Immunol. 138:47-53 (2004); Admyre, C. et al. J. Immunol. 179:1969-78 (2007); Oppenheim, J. J. and Yang, D. Curr. Opin. Immunol. 17:359-65 (2005)]. These can activate the innate and adaptive immune systems. Some of these proteins are also termed 'alarmins', in recognition of their role in mobilizing the immune system [Oppenheim (2005) ibid.]. Alarmins have both chemotactic and activating effects on APCs, and can thus amplify innate and Ag-specific immune responses to danger signals [Yang, D. et al. J. Immunol. 173:6134-42 (2004); Oppenheim, J. J. et al. Adv. Exp. Med. Biol. 601:185-94 (2007)]. BC (bovine colostrum) contains high levels of β-glycosphingolipids (BGS) [Martin, M. J. et al. Lipids 36:291-8 (2001); Sala-Vila, A. et al. Nutrition 21:467-73 (2005); Van, Y. H. et al. Diabetes 58:146-55 (2009); Nagatomo, T. et al. Clin. Exp. Immunol. 138:47-53 (2004)], the composition of which can determine the effect of APCs or other components of the gut-immune system [Novak, J. et al. Int. Key. Immunol. 26:49-72 (2007); Nowak, M. and Stein-Streilein, J. Int. Rev. Immunol. 26:95-119 (2007); Nikoopour, E. and Schwartz, J. A. Inflamm. Allergy Drug Targets 7:203-10 (2008); Admyre, C. et al. J. Immunol. 179:1969-78 (2007); Oppenheim, J. J. and Yang, D. Curr. Opin. Immunol. 17:359-65 (2005); Yang, D. et al. J. Immunol. 173:6134-42 (2004); Oppenheim, J. J. et al. Adv. Exp. Med. Biol. 601:185-94 (2007)]. Some of these mediators can serve as mucosal adjuvants, enhancing the cross talk between subsets of APCs and Tregs in the bowel mucosa [Vignali, D. A. et al. Nat. Rev. Immunol. 8:523-32 (2008); Margalit, M. et al. J. Pharmacol. Exp. Ther. 319:105-10 (2006); Godfrey, D. I. and Berzins, S. P. Immunol. 7:505-18 (2007; Margalit, M. and Ilan, Y. Liver Int. 25:501-4 (2005); Novak, J. et al. Int. Rev. Immunol. 26:49-72 (2007); Nowak, M. and Stein-Streilein, J. Int. Rev. Immunol. 26:95-119 (2007); Nikoopour, E. and Schwartz, J. A. Inflamm. Allergy Drug Targets 7:203-10 (2008)]. Induction of Treg cells may result in a long-lasting tolerance to (3 cell antigens, mediated by local immune modulation in the pancreatic draining lymph nodes (PLNs) [Homann, D. et al. J. Immunol. 163:1833-8 (1999); Homann, D. et al. Immunity 11:463-72 (1999)]. This intervention has shown great promise in animal models, but has had little efficacy in human trials. In the Diabetes Prevention Trial, only a sub-fraction of treated patients showed a beneficial effect with immunization with islet autoantigens [Skyler, J. S. et al. Diabetes Care 28:1068-76 (2005)]. Prevention of type 1 diabetes was only seen when patients were immunized during the pre-diabetic phase, and immunization was incapable of reverting recent-onset diabetes [Larche, M. and Wraith, D. C. Nat. Med. II:S69-76 (2005)]. Therefore, antigen-specific interventions may require additional adjuvants in order to be used successfully in humans, especially in recent-onset diabetics [Harlan (2005) ibid.].

The present inventors have shown dose dependent effects on the immune system.

In summary, the invention clearly demonstrates that anti-LPS antibodies together with colostrum adjuvants can promote Treg cell accumulation, and thereby serve as a means for alleviating inflammatory response, improving liver damage and improving Metabolic Syndrome complications. Further, according to the invention, Regulatory T lymphocytes in the adipose tissue and the SV can serve as a new therapeutic target in Metabolic Syndrome patients. Moreover, the immunoglobulins in the colostrum may promote regulatory T cells or any other cell related to the immune system in an antigen specific and non specific way, by targeting bystander antigens, or by being directed against non associated antigens.

Thus, in a first aspect, the present invention provides a composition comprising an anti-LPS enriched immunoglobulin preparation for use in treatment and/or prophylaxis of a pathologic disorder. The anti-LPS enriched immunoglobulin preparation may be derived from colostrum or from avian eggs.

"Treatment" as used herein refers to the reduction or elimination of the severity of a symptom of the disease, the frequency with which such a symptom is exhibited, or both.

"Prophylaxis" as used herein refers to completely or partially preventing or inhibiting a symptom of the disease or the frequency with which such a symptom is exhibited.

In a one aspect, the present invention provides a composition for the treatment and prophylaxis of a pathologic disorder. The composition of the invention comprises as active ingredient a mammalian anti-lipopolysaccharide (anti-LPS) enriched colostrum-derived immunoglobulin preparation and optionally further colostrum, milk or milk product component/s, and any adjuvant/s. The immunoglobulin preparation or any fractions thereof, recognizes and binds LPS and any fragments thereof. Optionally, the composition of the invention may comprise a combination of anti-LPS enriched colostrum-derived-immunoglobulin preparation with at least one immunoglobulin preparation comprising immunoglobulins recognizing at least one antigen specific for said disorder, thereby activating or inhibiting an immune response specifically directed towards said disorder. It should be further noted that the anti-LPS enriched colostrum-derived immunoglobulin preparations of the invention may be combined with any other immune modulatory drug, including but not limited to other colostrums derived antibodies, other antigen, other adjuvant, other cytokines or any type of molecule that can alter any component of the immune system. The combination can be administered as one product, or in two or more separate products. The combination may be administered together or separately from one another.

According to one specific embodiment, the colostrum-derived anti-LPS enriched immunoglobulin preparation may comprise monomeric, dimeric or multimeric immunoglobulin selected from the group consisting of IgG, IgA and IgM and any fragments thereof. As indicated above, in ruminants, the principal compositional difference between colostrum and mature milk is the very high content of colostral immunoglobulin, of which IgG class makes up 80-90%.

Thus, according to a specific embodiment, the colostrum-derived anti-LPS enriched immunoglobulin preparation of the invention mainly comprises IgG, specifically, IgG1 and IgG2.

Immunoglobulin G (IgG) as used herein, is a multimeric immunoglobulin, built of two heavy chains and two light chains. Each complex has two antigen binding sites, This is the most abundant immunoglobulin and is approximately equally distributed in blood and in tissue liquids, constituting 75% of serum immunoglobulins in humans. In general, the number of IgG subclasses varied widely between different species, ranging from one subclass in rabbits to seven subclasses in horses, making it difficult to find orthologues. In humans, for example, IgG1 and IgG3 are the most pro-inflammatory IgG subclasses. In mice, however, IgG2a and IgG2b are the most pro-inflammatory IgG molecules showing a greater activity than mouse IgG1 and IgG3 in many in vivo model systems.

Optionally or additionally, the anti-LPS enriched immunoglobulin preparation may comprise a secretory antibody, specifically, sIgA.

Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine. IgA output exceeds that of all other immunoglobulins, making it the major antibody produced by the body daily and is the major immunoglobulin found in human milk, whey and colostrum. IgM secretion is less abundant but can increase to compensate for deficiencies in IgA secretion. J chain containing IgA is produced and secreted by plasma B immunocytes located in the lamina propria just beneath the basement membrane of exocrine cells. IgA has a typical immunoglobulin four-chain structure ($M_r$ 160,000) made up of two heavy chains ($M_r$ 55,000) and two light chains ($M_r$ 23,000). In humans, there are two subclasses of IgA. These are IgA1 and IgA2 that have one and two heavy chains, respectively. IgA can occur as monomers, dimers, trimers or multimers. In plasma, 10% of the total IgA is polymeric while the remaining 90% is monomeric. The secreted IgA binds to a $M_r$ 100,000 poly-Ig receptor positioned in the basolateral surface of most mucosal cells. The receptor-IgA complex is next translocated to the apical surface where IgA is secreted. The binding of dimeric IgA to the poly-Ig receptor is completely dependent upon the presence of a J chain. Monomeric IgA will not bind to the receptor.

The difference in function of IgG and IgA, follows the position where the molecules operate. IgA is found mainly on mucosal surfaces where there is little in the way of tissue fluid to carry immune cells and chemicals. Therefore, IgA (often as a dimer) would be preferably used for physical neutralisation of pathogens, and may be too effective at other immune functions. IgGs are present in the tissue fluid and blood where there is the full collection of leukocytes, complement system, macrophages etc. may physically neutralize a pathogen effectively and are also more effective in a communication/presentation role than IgA, i.e., they tend to induce better opsonisation by phagocytes (e.g., Killer T cells and macrophages) and switch on the complement system better.

More specifically, the anti-LPS enriched immunoglobulin preparations of the invention may be obtained from any one of colostrum, colostrum serum, hyperimmunised milk or colostrum, colostrum whey (either cheese or casein), cheese or casein whey, directly from skim milk, whole milk, or a reconstituted form of such streams.

It should be appreciated that the anti-LPS enriched immunoglobulin preparation comprised within the composition of the invention may be any fraction of colostrum. Thus, the term colostrum where used herein includes colostral milk, processed colostral-milk such as colostral milk processed to partly or completely removes one or more of fat, cellular debris, lactose and casein.

The colostrum, or milk, containing the anti-LPS antibodies and optionally, the antigen-specific antibodies may be preferably collected by milking the animal colostrum or milk thus collected can either be used directly, may be further processed, for instance to purify anti-LPS and optionally, antigen-specific antibodies. Methods for the (partial) purification of (LPS and optionally, antigen-specific) antibodies from colostrum or milk are present in the art.

It should be further appreciated that any adjuvants may be added to the compositions of the invention. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

Alternatively, the anti-LPS enriched immunoglobulin preparation may be an affinity purified antibody or any fragment thereof. The term "antibody" is meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody. It will be appreciated that Fab and F(ab')$_2$ and other fragments of the antibodies useful in the present invention may be used for immuno-modulation, according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of specifically recognizing" a certain antigen if it is capable of specifically reacting with an antigen which is in this particular example an antigen or a mixture of antigens specific for a certain immune-related disorder, to thereby bind the molecule to the antibody.

An "antigen" is a molecule or a portion of a molecule capable of being bound by an antibody, which is additionally capable of inducing an animal to produce antibody capable of binding to an epitope of that antigen. An antigen may have one or more than one epitope. The term "epitope" is meant to refer to that portion of any molecule capable of being bound by an antibody that can also be recognized by that antibody. Epitopes or "antigenic determinants" usually consist of chemically active surface groupings of molecules such as amino acids or sugar side chains, and have specific three-dimensional structural characteristics as well as specific charge characteristics.

In yet another embodiment, the anti-LPS enriched immunoglobulin preparation used as an active ingredient for the composition of the invention may be obtained from a mammal immunized with LPS or any fragments thereof. Optionally, in addition to LPS, said mammal according to certain embodiments may be further immunized with at least one antigen or a mixture of at least two antigens specific for said disorder, as well as with a mixture of at least two different antibodies directed against at least two different antigens associated with the disease.

According to one embodiment, the LPS or any antigen used for immunizing said mammal, preferably, bovine or avian, may be provided as any one of an isolated and purified peptide, a purified recombinant protein, a fusion protein, cell lysate, membranal preparation, nuclear preparation, or cytosolic preparation of any one of tissue culture cells, primary cells or tissue samples obtained from a subject suffering from said disorder.

According to another embodiment, the composition of the invention may optionally further comprise colostrum component/s such as for example, alarmins, defenensins, colostrinin, and any other colostrum or milk derived carbohydrates, glycolipids or any other molecules or components that may further enhance or inhibit modulation of an immune response, or any preparations, mixtures or combinations thereof. Moreover, the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

In some embodiments of the composition, the composition comprises a constituent of a bird's egg, wherein the bird's egg comprises IgY specific for LPS or a fragment thereof. Crude egg yolk may be used as an antibody source However, avian antibodies are usually purified or concentrated from the yolk prior to use. The constituent of the bird's egg may be concentrated or purified as necessary, as is understood by those skilled in the art In some embodiments of the composition, the composition comprises the yolk of the egg, or any IgY antibody-containing fraction thereof. The yolk is preferable to the white of the egg, as the yolk typically contains much higher concentrations of IgY than does the white. However, the white may contain concentrations of IgY sufficient for some applications.

In some embodiments of the antibody composition, the IgY is concentrated, isolated, or purified from the constituent of the bird egg This can be accomplished by a variety of methods In some embodiments the antibodies may be purified by the water dilution method. The precipitate may then be removed by any conventional method, including centrifugation. The supernatant can then be stored frozen, for example at −20° C. IgY can then be isolated by precipitation with ammonium sulfate and subsequent dialysis. If desired, the titer of IgY antibodies can be determined by immunoassay, for example ELISA. The water dilution method is more completely described in the well-known literature, for example by Akita and Nakai (1993), which is incorporated by reference to teach this method. Other useful methods are described for example is U.S. Pat. No. 4,550,019, U.S. Pat. No. 4,748,018, and U S Patent Publication 2004/0161427 which are hereby incorporated by reference for such teachings Commercial kits are available for example from the Promega Corporation (Madison, Wis.).

Some embodiments of the antibody composition are substantially isolated In such embodiments a significant fraction of a non-antibody yolk component has been removed. The non-antibody yolk component may be for example the lipid component of the yolk, the carbohydrate component of the yolk, the yolk granules, the hydrophobic component of the yolk, the steroid component of the yolk, and the non-immunoglobulin protein component of the yolk. The fraction of the component removed is at least 50%. In some embodiments the removed fraction is at least 60%, 75%, 80%, 90%, 95%, 99%, or 99 9%. Greater removed fractions have the advantage of producing a more pure antibody composition. Smaller removed fractions have the advantage of requiring less processing.

Some embodiments of the antibody composition are substantially concentrated. In such embodiments the concentration of IgY will be greater in the composition than in the egg yolk. Substantially concentrated antibody compositions comprise IgY that is at least twice as concentrated as in the yolk. Some embodiments of the substantially concentrated antibody composition are concentrated by at least a factor of 3, 4, 5, 6, 7, 8, 9, 10, 100, 1000, or 10,000. More concentrated antibody compositions have the advantage of providing the same mass of antibodies in lower volume. Less concentrated antibody compositions have the advantage of requiring less processing.

The antibody compositions of the present disclosure may be processed so as to largely remove all isotypes except IgG and IgY. In some embodiments the immunoglobulin may be derived from numerous donors. Any number of donors may be used In some embodiments, the antibodies are derived from one donor. In further embodiments, the antibodies are derived from 1-10 donors. In further embodiments, the antibodies are derived from 10-100 donors. In further embodiments, the antibodies are derived from 100-1000 donors. In still further embodiments, the antibodies are derived from over 1000 donors.

In some embodiments of the antibody composition, the composition is made by the method comprising obtaining an egg laid by a fowl previously immunized against influenza and separating the antibody fraction from a yolk of the egg. In some embodiments of the composition the fowl has been actively immunized, for example by vaccination. The fowl is preferably a domesticated fowl The domesticated fowl may be chicken, duck, swan, goose, turkey, peacock, guinea hen, ostrich, pigeon, quail, pheasant, dove, or other domesticated fowl The domesticated fowl is preferably a chicken The domesticated fowl is more preferably a domesticated chicken raised primarily for egg or meat production. The fowl may be immunized against any strain of influenza, any subtype of influenza, any type of influenza, or combinations thereof.

Use of eggs from chickens raised for egg or meat production, and which are vaccinated pursuant to this purpose, has the great advantage of using as the feedstock for the process eggs that are widely available commercially in great volumes and at very low price. Previously, animals used for the production of antibodies have been raised solely or mainly for that purpose, and maintained in small numbers at very high expense.

In some embodiments of the antibody composition, the antibody composition is made by a method comprising actively immunizing a hen with antigen, collecting eggs from the hen after an immunization period, and separating the antibody fraction from a yolk of the egg. Optionally, collecting eggs from the hen can occur continuously after the immunization period. The immunization of the bird may occur by any means known in the art. For example, a vaccine may be administered to the bird that is known to effectively elicit an immune response in birds, or that is known to effectively elicit an immune response in mammals. Many such influenza vaccines are commercially available, and can be routinely developed by those of ordinary skill m the art without undue experimentation further methods of producing IgY with a specific target are known to those skilled in the art.

Such methods can be found for example in U.S. Pat. No. 4,550,019, U.S. Pat. No. 4,748,018, and U S Patent Publication 2004/0161427, and U.S. Pat. No. 6,537,500, which are incorporated by reference.

In one embodiment, the present invention provides a composition comprising an anti-LPS enriched immunoglobulin preparation for use in treatment and/or prophylaxis of a pathologic disorder wherein the anti-LPS enriched immunoglobulin preparation is derived from avian eggs and further comprising non-hyperimmune colostrum.

In one embodiment, the pathologic disorder is acute or chronic liver disease, cirrhosis or any disease or complication associated therewith. In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness. In another embodiment, the pathologic disorder is liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder.

Alternatively, the pathologic disorder may be selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In one embodiment, the immuno-modulating composition of the invention is capable of reducing, eliminating or inhibiting mucosal microbial translocation, thereby modulating immune activation. It should be noted that chronic activation of the immune system is a hallmark of progressive viral infection and predicts disease outcome. It has been previously shown that circulating microbial products, likely derived from the gastrointestinal tract, in a process also known as "mucosal microbial translocation", are a primary cause of virus-related systemic immune activation. Thus, according to certain embodiments, the compositions of the invention may modulate immune function, or alternatively, reduce or change the number of bacteria or of bacteria related products not related to alteration of the immune system.

According to one embodiment, the invention provides a composition comprising as an active ingredient a mammalian anti-lipopolysaccharide (LPS) enriched colostrum-derived immunoglobulin preparation. Such composition wherein said composition is particularly applicable for the treatment, prevention and prophylaxis of acute or chronic liver disease, cirrhosis and any disease or complication associated therewith, optionally said composition further comprises an additional therapeutic agent or any carrier and adjuvant.

More specifically, according to the invention, acute or chronic liver disease, cirrhosis and any disease or complication associated therewith may be for example, at least one of hepatic encephalopathy, spontaneous bacterial peritonitis (SBP), ascitess, variceal bleeding, cirrhosis associated hyperdynamic circulation, hepatorenal syndrome, hepatopulmonary syndrome, portopulmonary hypertension, variceal bleeding, adrenal insufficiency and altered level of consciousness.

In a further embodiment, the composition of the invention may be used for the treatment of pathologic disorders such as any type of viral disease including HCV, HBV, CMV, and EBV.

It should be noted that such colostrum-derived preparations may be therefore combined with any drug used for liver disease, as an additional therapeutic agent.

The term "cirrhosis" as used herein refers to the final common histological outcome of a wide verity of chronic liver diseases, characterized by the replacement of liver tissue by fibrous scar tissue and regeneration of nodules, leading to progressive loss of liver function. Cirrhosis is usually caused by Hepatitis B and C viruses, alcoholism and fatty liver disease.

The term "ascites", as used herein describes the condition of pathologic fluid accumulation within the abdominal cavity, most commonly due to cirrhosis and sever liver disease.

It should be noted that such colostrum-derived preparations may be therefore combined with any immunomodulatory therapeutic agent/s or any combination or mixture thereof, creating a combined immunomodulatory composition for the treatment and/or prevention of immune-related disorders, a non alcoholic steatohepatitis, fatty liver, atherosclerosis, metabolic syndrome and any disorder associated therewith, infectious disease, malignant or infectious disorders.

It should be noted that the colostrum-derived composition of the invention may further comprises any added adjuvant.

It should be noted that since microbial translocation is also associated with alteration of the liver inflammation in many liver disorders, including viral-mediated, drug-mediated, non alcoholic steatohepatitis and any other hepatic disorder, as well as with insulin resistance, diabetes type 2, obesity and overweight, prevention of this translocation by the composition of the invention may be applicable in the treatment of these disorders. Therefore, the invention further provides the use of the anti LPS compositions of the invention, optionally, combined with colostrum preparations enriched for antibodies directed against antigens associated with a disease, for example, anti-insulin antibodies, in the treatment of any acute or chronic liver disease, diabetes, and any complication of diabetes, fatty liver, non alcoholic steatohepatitis, and obesity.

In another embodiment, the composition further comprises an immunoglobulin preparation comprising immunoglobulins that recognize and bind at least one antigen specific for said pathologic disorder. The further immunoglobulin preparation may be derived from colostrum or from avian eggs.

According to one optional embodiment, the invention provides combined compositions comprising a combination of anti-LPS enriched immunoglobulin preparation with at least one colostrum-derived immunoglobulin preparation comprising immunoglobulins that recognize and bind at least one antigen specific for said pathologic disorder and thereby modulate immune-regulatory cells, specifically, regulatory T cells. It should be noted that such modulation may results for example, in modulation of the Th1/Th2, Tr1/Th3 cell balance toward an anti-inflammatory Th2, Tr1/Th3 immune response thereby inhibiting an immune response specifically directed toward said disorder.

Immunoglobulins that recognize and bind at least one antigen specific for said pathologic disorder and thereby modulate immune-regulatory cells, specifically, regulatory T cells include the following:

Anti influenza antibodies for the treatment and/or prophylaxis of influenza; Anti HCV antibodies for the antibodies for the treatment and/or prophylaxis of any type of liver cancer or acute and chronic liver disorders associated with HCV infection; Anti HBV antibodies for the treatment and/or prophylaxis of any type of liver cancer or acute and chronic liver disorders associated with HBV infection; Anti CMV antibodies for the treatment and/or prophylaxis of acute and chronic disorders associated with CMV infection; anti amyloid antibodies for the treatment and/or prophylaxis of Alzheimer's disease, hepatic encephalopathy, any type of memory loss, attention deficit disorders (ADHA), any type of learning disability, effect of alcohol or drugs on the brain, antibodies against any viral, bacterial, spirochetal, preon, parasitic, spore or fungal antigen for the treatment and/or prophylaxis of acute and chronic disorders associated with the relevant infection; anti-insulin antibodies for the treatment and/or prophylaxis of any disorder associated with insulin resistance; antibodies against any type of cancer associated antigen for the treatment and/or prophylaxis of any malignant disorder including metastatic and non metastatic, solid and non solid that is associated to the target antigen; antibodies against disease specific and disease associated antigens for the treatment and/or prophylaxis of any type of immune mediated or autoimmune disease; anti-HSV, JC virus, Adenovirus, Parainfluenza virus and RSV antibodies for the treatment and/or prophylaxis of viral disease; anti Mycoplasma/Legionella antibodies for the treatment and/or prophylaxis of pneumonia; anti PTHrp, aldosteron, steroids, GH and prolactin antibodies for the treatment and/or prophylaxis of secreting tumors; anti IL-12, omp C antibodies for the treatment and/or prophylaxis of IBD; Anti Intrinsic Factor antibodies for the treatment and/or prophylaxis of Megaloblastic anemia; anti *H. pylori* antibodies or the treatment and/or prophylaxis of *H. pylori* infection; anti EBV antibodies for the treatment and/or prophylaxis of Burkitt's lymphoma; and antibodies specific for antigens associated with Autoimmune pancreatitis, Chronic lung diseases such as CF, Asthma etc, Liver Cirrhosis, liver fibrosis (CCL4), and Hyperclacemia.

According to another alternative embodiment, the anti-LPS enriched immunoglobulin preparation of the invention may further comprise immunoglobulins directed to antigens that are not specific to the treated disorder. Such antigens may be any target immune-related components having a modulatory effect on the immune-response. Thereby, recognition of such disease non-specific antigens by the immunoglobulin preparation of the invention may results in alteration of the immune-response. Such modulation may results for example, in modulation of the Th1/Th2, Trl/Th3 cell balance toward an anti-inflammatory Th2, Trl/Th3 immune response thereby inhibiting an immune response specifically directed toward said disorder. According to another embodiment, the combined composition of the invention may optionally further comprises an additional therapeutic agent or any carrier and adjuvant.

Alternatively or additionally, the combined colostrums-derived immunoglobulin preparation of the invention as well as the immuno-modulatory composition derived therefrom, may act in an indirect manner by activation or promotion of specific subsets of regulatory cells, or antigen presenting cells, or by any type of cell-cell contact. Such anti-LPS enriched combined composition may be directed towards different components of the immune-system. For example, activation of specific regulatory T cells, B cells or antigen presenting cells, or any other cells that associated with an effect on the immune system, or induces the secretion of cytokines or chemokines or affects the immune system in any other way. Alteration or promotion of immune cells may further involve induction of any type of regulatory cells, preferably, regulatory T cells, for example, Th3 cells, Trl, T17 cells or any other type of regulatory, effector or suppressor cells. It should be noted that Th17 cells are a recently-identified subset of CD4 T helper cells. They are found at the interfaces between the external environment and the internal environment, e.g., skin and lining of the GI tract. More specifically, it should be noted that the colostrum-derived anti-LPS enriched immunoglobulin preparations of the invention may promote regulatory T cells or any other cell related to the immune system in an antigen specific and non specific manner, by targeting bystander antigens, or by being directed towards non associated antigens.

Thus, according to another embodiment, the invention provides a combination of an anti-LPS enriched immunoglobulin preparation of the invention with at least one additional immunoglobulin preparation comprising immunoglobulins directed against at least one antigen associated with said disorder, creating a combined composition for treating immune-related disorders. Such composition therefore may be antigen or disease specific or alternatively, may augment or induce specific cells or parts of the immune system in a non-antigen specific way, including an immune bystander effect.

In one embodiment, the composition modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the composition modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment, the composition is for the treatment and/or prophylaxis of metabolic syndrome or non alcoholic steatohepatitis or both. In another embodiment, the composition is for the treatment, and/or prophylaxis of diabetes, the treatment of impaired glucose tolerance, such as decreasing glucose tolerance. decreasing serum insulin levels, decreasing hepatic triglyceride levels, or decreasing cholesterol levels.

In one embodiment, the composition modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders.

The composition may further comprise a therapeutic agent, carrier or adjuvant and/or non-hyperimmune colostrum.

It should be further appreciated that the anti-LPS enriched immunoglobulin preparation of the invention may be used either for an active or a passive treatment.

In a further embodiment of the immuno-modulating composition of the invention, said immune-related disorder is any one of autoimmune disease, infectious disease, and proliferative disorder.

It should be noted that the composition of the invention may be applicable for treating acute complications, or prevention the development or the recurrence of these complications.

According to one embodiment, the combined composition of the invention leads to modulation of the Th1/Th2, Trl/Th3 cell balance toward an anti-inflammatory Th2, Trl/Th3 immune response thereby inhibiting an immune response specifically directed toward said disorder. Such regulation may involve regulatory T cells, antigen presenting cells, any type of T cell or B cell, the function of any cell associated directly or indirectly with the immune system, or any type of cytokine or chemokine, or adjuvant. According to this specific embodiment, such composition may be applicable in the treatment of an autoimmune disease. Examples of autoimmune disorders include, but are not limited to, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The combined compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In yet another embodiment, the combined compositions of the invention may be used for treating any one of non alcoholic steatohepatitis, fatty liver, atherosclerosis, metabolic syndrome and any disorder associated therewith for example, diabetes type 2, insulin resistance, obesity and overweight.

Alternatively, the combined composition of the invention may lead to modulation of the Th1/Th2, Trl/Th3 cell balance toward a pro-inflammatory Th1/Th2 immune response thereby enhancing an immune response specifically directed toward said disorder. Such regulation may involve regulatory T cells, antigen presenting cells, any type of T cell or B cell, the function of any cell associated directly or indirectly with the immune system, or any type of cytokine or chemokine, or adjuvant. According to this specific embodiment, such composition may be applicable in the treatment of infectious diseases, and proliferative disorders.

According to one specific embodiment, a malignant proliferative disorder that may be a solid or non-solid tumor, for example, carcinoma, sarcoma, melanoma, leukemia, myeloma or lymphoma.

According to another specific embodiment, the composition of the invention is intended for preventing and/or treating carcinoma such as hepaotcellular carcinoma, prostate cancer, breast carcinoma, colon carcinoma. In yet another embodiment, the composition of the invention may be used for preventing and/or treating leukemia, more specifically, acute or chronic leukemia.

As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

Malignancy, as contemplated in the present invention may be selected from the group consisting of carcinomas, melanomas, lymphomas and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be hepaotcellular carcinoma, colon cancer, melanoma, myeloma and acute or chronic leukemia.

According to another embodiment, the immuno-modulating composition of the invention may be specifically applicable for treating infectious diseases, for example, conditions caused by viral pathogens such as HCV, HBV, CMV, and EBV.

According to one particular embodiment, the combined immunomodulatory composition of the invention may lead to a Th2, Trl/Th3 anti-inflammatory response. More specifically, such anti-inflammatory response may be accompanied by a decrease or reduction in the amount or expression of pro-inflammatory cytokines such as IL-2, IL-17, IL-23, IFN-γ, IL-6. Such decrease or reduction according to the invention may be a reduction of about 5% to 99%, specifically, a reduction of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. In yet another specific embodiment, the composition of the invention may elevate and increase the amount or expression of anti-inflammatory cytokines such as TGF-β, IL-10, IL-4, IL-5, IL-9 and IL-13. More specifically, the increase, induction or elevation of the anti-inflammatory cytokines may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

It should be appreciated that the anti-inflammatory effect of the combined immuno-modulatory composition of the invention may be achieved by activation or promotion of specific subsets of regulatory cells, antigen presenting cells or any type of cell-cell contact, or via direct or indirect activation of cytokines and/or chemokines. It should be further noted that any type of regulatory or effector cell, specifically regulatory T cells, including Th3 and Trl. cells may be involved. Thus, the colostrum-derived anti-LPS enriched immunoglobulin preparations of the invention may promote regulatory T cells or any other cell related to the immune system in an antigen specific and non specific way, by targeting bystander antigens, or by being directed against non associated antigens.

More specifically, an immune-related cell activated or promoted by the composition of the invention may be an APC (such as DC), Treg cell or any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties. More particularly, the compositions of the invention demonstrate anti-inflammatory effect on immune-related cells such as specific T regulatory cells for example, adipocytes and Antigen Presenting Cells (APC), such as DC. Therefore, according to one embodiment, the composition of the invention may be used for inducing at least one of T regulatory (Treg) cells, or any cell having regulatory properties, either suppressive or inductive, adipocyte and Antigen Presenting Cells (APC) in a subject suffering from hepatic disorder.

As indicated above, the compositions or the optional combined compositions of the invention are intended for preventing and/or treating a pathologic disorder, specifically, hepatic disorders, or an immune-related disorder. As Used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein. It should be further noted that an "immune-related disorder or disease" or "hepatic disorder" may be any disorder associated with, caused by, linked to, a non normal immune response. Such disorders may usually occur together with a disturbed immune response, or believed to have an impact on or by a non normal immune response.

The composition may be formulated for administration orally, by inhalation as an aerosol, or by parenteral, intravaginal, intranasal, mucosal, sublingual, topical, or rectal administration, or any combination thereof.

In one embodiment, the immunoglobulin preparation or any fractions thereof recognizes and binds LPS or any fragments thereof.

In another embodiment, the composition inhibits microbial translocation. In another embodiment, the composition inhibits microbial translocation and thereby modulates immune activation.

In another aspect, the present invention provides a composition comprising a mammalian anti-LPS enriched colostrum-derived immunoglobulin preparation for modulating immune tolerance in a subject, or in another aspect, for modulating oral tolerance in a subject According to one preferred embodiment, any of the compositions of the invention may be administered orally or by inhalation as an aerosol or by intravenous, intramuscular, subcutaneous, intraperitoneal, parenteral, transdermal, intravaginal, intranasal, mucosal, sublingual, topical, rectal or subcutaneous administration, or any combination thereof. Orally administrated antibodies would be expected to be degraded in the gastrointestinal tract, given the low gastric pH and the presence of gastric and intestinal proteases. However, bovine colostral IgG (BCIg) has been cited as particularly resistant to GI destruction, relative to other immunoglobulins. Early studies of BCIg cited remarkable "resistance to proteolytic digestion in the intestine of a heterologous host". There is also evidence that bovine IgG1 is somewhat more resistant to proteolysis by trypsin, chymotrypsin and pepsin than other Igs. These results drove much of the early development of oral antibody therapy. More specifically, the composition of the invention may be suitable for mucosal administration, for example, pulmonary, buccal, nasal, intranasal, sublingual, rectal, vaginal administration and any combination thereof.

As indicated above, although oral and nasal administration are preferred, it should be appreciated that any other route of administration may be applicable, for example, intravenous, intravenous, intramuscular, subcutaneous, intraperitoneal, parenteral, intravaginal, intranasal, mucosal, sublingual, topical, rectal or subcutaneous administration, or any combination thereof.

Moreover, the anti-LPS enriched immunoglobulin preparation used by the compositions and combined compositions of the invention may be prepared in preparations such as food additives, aqueous solutions, oily preparations, emulsions, gels, etc., and these preparations may be administered orally, topically, rectally, nasally, bucally, or vaginally. The preparations may be administered in dosage formulations containing conventional non-toxic acceptable carriers and may also include one or more acceptable additives, including acceptable salts, polymers, solvents, buffers, excipients, bulking agents, diluents, excipients, suspending agents, lubricating agents, adjuvants, vehicles, delivery systems, emulsifiers, dis-integrants, absorbents, preservatives, surfactants, colorants, flavorants or sweeteners. An optional dosage form of the present invention may be a powder for incorporation into beverages, pills, syrup, capsules, tablets, granules, beads, chewable lozenges or food additives, using techniques known in the art. Thus, immuno-modulating composition of the invention may be administered in a form selected from the group consisting of orally-active powders, pills, capsules, teas, extracts, dried extracts, subliguals, sprays, dispersions, solutions, suspensions, emulsions, foams, syrups, lotions, ointments, gels, pastes, dermal pathces, injectables, vaginal creams and suppositories.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal or by inhalation) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice.

The composition of the invention may comprise the active substance in free form and be administered directly to the subject to be treated, Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

Formulations include those suitable for oral, nasal, or par enteral (including subcutaneous (s.c.), intramuscular (i.m.), intraperitoneal (i.p.), intravenous (i.v.) and intradermal or by inhalation to the lung mucosa) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components (anti-LPS enriched immunoglobulin preparation or a combination with other immunoglobulin preparation) can be combined with a non-toxic pharmaceutically acceptable inert carrier such as lactose, starch, sucrose; glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

In another aspect, the present invention provides the use of a mammalian anti-LPS enriched colostrum-derived immunoglobulin preparation and optionally of a colostrum-derived immunoglobulin preparation recognizing at least one antigen specific for a pathologic disorder in the manufacture of an immuno-modulating composition for the treatment and prophylaxis of a pathologic disorder. It should be noted that the anti-LPS enriched immunoglobulin preparation or any fractions thereof recognizes and binds LPS and any fragments thereof. Optionally, the composition prepared by the use of the invention may comprise a combination of the anti-LPS enriched immunoglobulin preparation of the invention and at least one immunoglobulin preparation comprising immunoglobulins recognizing at least one antigen specific for said disorder. Such recognition leads to alteration of regulatory T cells, and as a result, causes modulation of the Th1/Th2, Trl/Th3 cell balance either toward an anti-inflammatory Th2, Trl/Th3 immune response or toward a pro-inflammatory Th1 immune response. Thereby creating a combined immuno-modulating composition inhibiting or activating an immune response specifically directed toward said disorder.

It should be noted that any type of regulatory or effector cells, specifically regulatory T cells, including Th3 and Trl [$T_H3$, T cells are preferentially induced at mucosal surfaces and secrete transforming growth factor (TGF)-β] cells may be involved. Moreover, it should be noted that the colostrum-derived anti-LPS enriched immunoglobulin preparations of the invention may promote regulatory T cells or any other cell related to the immune system in an antigen specific and non specific way, by targeting bystander antigens, or by being directed against non associated antigens.

According to one embodiment, the anti-LPS enriched colostrum-derived immunoglobulin preparation used for the invention comprises monomeric, dimeric or multimeric immunoglobulin selected from the group consisting of IgG, IgA and IgM and any fragments, mixtures or combinations thereof.

In yet another embodiment, the use according to the invention of colostrum-derived, milk or milk products-derived anti-LPS enriched immunoglobulin preparation is for manufacturing a composition or combined composition that optionally may further comprises colostrum, milk or milk products component/s and any adjuvant/s, preferably, alarmins, defenensins, colostrinin and any preparation, mixture or combination thereof. It should be further appreciated that the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner. It should be noted that according to certain embodiments the present invention further provides the use of colostrum or any colostrum-derived preparations in the combined compositions of the invention for enhancing an immunomodulatory effect of an immunomodulatory therapeutic agent.

The term alarmin, denotes an array of structurally diverse multifunctional host proteins that are rapidly released during infection or tissue damage, and that have mobilizing and activating effects on receptor-expressing cells engaged in host defence and tissue repair. Innate-immune mediators that have alarmin function include defensins, eosinophil-derived neurotoxin, cathelicidins and HMGB1.

Defensins are small (15-20 residue) cysteine-rich cationic proteins found in both vertebrates and invertebrates. They are active against bacteria, fungi and enveloped viruses. They consist of 15-20 amino acids including six to eight conserved cysteine residues. Cells of the immune system contain these peptides to assist in killing phagocytized bacteria, for example in neutrophil granulocytes and almost all epithelial cells. Most defensins function by penetrating the microbial's cell membrane by way of electrical attraction, and once embedded, forming a pore in the membrane which allows efflux.

The term "Colostrinin", as use herein refers to a polypeptide which, in its natural form, is obtained from mammalian colostrum. Colostrinin is sometimes known as "colostrinine", and has a molecular weight in the range 16,000 to 26,000 Daltons. Colostrinin may form a dimer or trimer of sub-units (each having a molecular weight in the range 5,000 to 10,000 Daltons, preferably 6,000 Daltons), and contains mostly praline (the amount of proline is greater than the amount of any other single amino acid).

Colostrinin is characterized in that it stimulates the production of cytokines, especially gamma interferon (IFN-γ), tumor necrosis factor TNF-α), interleukins (e.g. IL-6 and IL-10) and various growth factors.

As indicated above, it should be noted that the anti-LPS enriched immunoglobulin preparation and any other optional immunoglobulin preparations used by the invention may be obtained from a mammal, immunized with LPS or any fragments thereof and optionally, in addition, with at least one antigen or a mixture of at least two antigens specific for the disorder to be treated. Means and methods of the invention are suited to obtain high and prolonged antigen-specific antibody production in the colostrum, milk or milk products of any lactating mammal. Preferably, said animal is a farm-animal. Farm animals are animals that are used on a commercial basis by man, be it for the production of milk, meat or even antibodies. Farm-animals already used for the commercial scale production of milk are preferred for the present invention since for these animals special lines and/or breeds exist that are optimized for milk production. Preferably, said farm-animal is a cow or a goat. More preferably said farm-animal is a cow.

In one embodiment of said use of the invention, the composition reduces or inhibits mucosal microbial translocation. In one embodiment of said use of the invention, the composition reduces or inhibits mucosal microbial translocation and thereby modulates immune activation.

According to one embodiment, the invention relates to the use of a mammalian anti-LPS enriched colostrum-derived immunoglobulin preparation for manufacturing a composition for the treatment, prevention and prophylaxis of acute or chronic liver disease, cirrhosis and any disease or complication associated therewith, optionally said composition further comprises an additional therapeutic agent or any carrier and adjuvant.

According to one embodiment of the use of the invention, this particular composition reduces or inhibits mucosal microbial translocation and thereby alters the direct effect of bacteria or any other infectious agent on the pathogenesis of complications of acute or chronic liver diseases-associated complications whether due to portal hypertension or any other cause.

More specifically, as used herein, acute or chronic liver disease, cirrhosis and any disease or complication associated therewith is at least one of hepatic encephalopathy, spontaneous bacterial peritonitis (SBP), ascites, cirrhosis associated hyperdynamic circulation, hepatorenal syndrome, hepatopulmonary syndrome, portopulmonary hypertension, variceal bleeding, adrenal insufficiency and altered level of consciousness.

It should be noted that these complications may results from chronic HCV infection, alcoholic hepatitis, chronic HBV, non alcoholic steatoheaptitis, drug induced liver injury, or any other cause of acute or chronic liver disease.

According to an optional embodiment, the invention provides the use of a combination of anti-LPS enriched immunoglobulin preparation with at least one colostrum-derived immunoglobulin preparation comprising immuno-globulins that recognize and bind at least one antigen specific for said pathologic disorder. According to this particular embodiment, the use of such combination is for preparing an immuno-modulatory composition that modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder. Optionally such combined composition further comprises an additional therapeutic agent or any carrier and adjuvant. Such composition modulates regulatory T cells leading to modulation of the Th1/Th2, Trl/Th3 cell balance toward an anti-inflammatory Th2, Trl/Th3 immune response or a pro-inflammatory Th1 immune response, thereby inhibiting or activating an immune response specifically directed toward said disorder.

In a further embodiment, the immune-related disorder may be any one of autoimmune disease, non alcoholic steatohepatitis, fatty liver, metabolic syndrome and any disorder associated therewith, infectious disease, and proliferative disorder.

According to one embodiment of the use of the invention, the composition of the invention may be used for treating acute complication, or for preventing the development or recurrence of these complications.

According to another embodiment, the combined composition of the invention leads to modulation of the Th1/Th2, Trl/Th3 cell balance toward an anti-inflammatory Th2, Trl/Th3 immune response thereby inhibiting an immune response specifically directed toward said disorder. According to this specific embodiment, such composition may be applicable in the treatment of an autoimmune disease.

Alternatively, the combined composition of the invention may lead to modulation of the Th1/Th2, Trl/Th3 cell balance toward a pro-inflammatory Th1/Th2 immune response thereby enhancing an immune response specifically directed toward said disorder. According to this specific embodiment, such composition may be applicable in the treatment of infectious diseases, and proliferative disorders.

In an even further embodiment of said use of the present invention, the composition of the invention may be administerable orally or by inhalation as an aerosol, or via intravenous, intramuscular, subcutaneous, intraperitoneal, perenteral, transdermal, intravaginal, intranasal, mucosal, sublingual, topical, rectal or subcutaneous, or any combination thereof.

Tolerance has been defined as a lack of response to self, or any mechanism by which a potentially injurious immune response is prevented, suppressed, or shifted to a non-injurious class of immune response. Thus, tolerance is related to productive self-recognition, rather than blindness of the immune system to its own components. The present inventors have demonstrated that exposure to disease-associated antigens, whether self-antigens or not, can activate some parts of the immune system while suppressing unwanted immunity in an antigen-specific manner. Without wishing to be bound by theory, oral antigen administration, on one hand activates specific subsets of cells, suppressing specific cells and alleviating unwanted autoimmunity, and on the other hand promotes anti-viral or anti-tumor-associated antigen immune responses. For many immune-mediated diseases or disorders in which the immune system plays a role, the balance between different types of signals/cells that are promoted in the systemic immune system will determine the final immunological effect.

Oral tolerance is a natural immunologic process driven by the presence of an exogenous antigen that is thought to have evolved to treat external agents that gain access to the body via a natural route and then become part of the self. With the understanding that oral exposure to antigens in the gastrointestinal tract such as the bowel results in an active immune response, antigen-specific therapy seems an attractive approach for immunotherapy toward antigens present in the gut mucosa, where they can be dealt with in a noninjurious or noninflammatory immunologic environment. Accordingly, specific immune cells may be activated and, antigen-specific therapy can serve as an immunotherapeutic chronic hepatitis, infectious agents, metabolic syndrome and other pathologic disorders discussed herein.

The mechanisms responsible for gastrointestinal homeostasis involve a complex interplay between different types of T cells, including regulatory T cells, dendritic cells (DCs), natural killer T (NKT) cells, and the gut microenvironment.

The follicle-associated epithelium (FAE) plays key roles in antigen uptake and subsequent induction of mucosal immunity. FAE M cells, by targeting antigen (Ag) delivery, facilitate oral tolerance via the reduction in Ag-specific CD4+ T cells and increased levels of transforming growth factor (TGF)-$\beta$ and interleukin (IL)-10-producing CD25+ CD4+ T- regulatory cells (Tregs) in both systemic and mucosal lymphoid tissues.

Intestinal DCs are key regulators of pathogenic immunity, oral tolerance, and intestinal inflammation. The relevant DCs may be in the PP, MLNs, or LP of the villus mucosa. All of these tissues contain a number of distinctive DC subsets, including some that can preferentially induce the differentiation of Tregs.

NKT cells are a unique lineage of T cells that share properties with both NK cells and memory T cells. This subset of lymphocytes may be either CD4+ or double negative and is CD1d reactive. These cells are unique in their invariant V$\alpha$14-J$\alpha$18 TCR $\alpha$-chain, and their T-cell receptor (TCR) $\beta$-chain is biased toward V$\beta$8.2, V$\beta$2, and V$\beta$7. NKT cells are unique in their glycolipid antigen reactivity and marked cytokine production. The ability of NKT cells to generate both Th1 and Th2 responses indicates their importance as immunoregulatory cells. The use of NKT ligands induces a profound immunomodulatory effect by altering the plasticity of these cells.

The present inventors have demonstrated a role for NKT cells in oral tolerance induction, and recent evidence have provided evidence for cross talk between Tregs and NKT cells. Without wishing to be bound by theory, it is thought that NKT cells produce cytokines immediately after exposure to activating signals and can determine the differentiation of Tregs.

The liver is considered to be important for oral tolerance. The liver is a site at which apoptotic CD8+ T cells accumulate during the clearance phase of peripheral immune responses. The normal mouse liver contains an unusual mixture of lymphocytes, in which natural killer (NK) and natural killer T (NKT) cells are abundant and apoptotic T cells are also present. These cells are relevant for intrahepatic T-cell trapping and killing. Continuous exposure of diverse liver cell types to LPS derived from intestinal bacteria is thought to promote expression of cytokines, antigen-presenting molecules, and costimulatory signals that impose T-cell inactivation. Other possible explanations for the tolerogenic environment in the liver involve clonal deletion, specific antigen presentation by endothelial cells or Kupffer cells, and the ability to induce regulatory T cells.

Different stimuli in the liver microenvironment are associated with T-cell priming and the generation of an effective immune response, whereas others result in tolerance. Antigen presentation in the liver by dendritic cells and their migration into the liver represent part of the interplay in the gut-liver axis. Liver-derived DCs are inherently tolerogenic when compared with skin DCs, produce IL-10, and express low levels of costimulatory molecules. Local secretion of IL-10 and TGF-$\beta$ by Kupffer cells and hepatocytes can skew DC function toward the generation of regulatory as opposed to effector pathways. Liver sinusoidal endothelial cells (LSECs) are capable of trafficking antigens to an early endosomal compartment committed to presentation on MHC class I, explaining their ability to cross-present to CD8+ T cells. The outcome of antigen presentation by LSECs is usually tolerance, with apoptosis of CD8+ T cells and secretion of IL-4 and IL-10 by CD4+ T cells. Activated T cells are also trapped by intercellular adhesion molecule 1 (ICAM-1)-dependent mechanisms within the sinusoids as a mechanism for regulating apoptotic pathways during control of systemic CD8 responses. Hepatocytes themselves can function as APCs to activate naive T cells. In most cases, activation by hepatocytes leads to antigen-specific tolerance, but this process may also involve activation of Tregs. Peripheral Tregs are generated by activation of naive T cells by immature DCs or in the presence of IL-10 and TGF-$\beta$, both of which are present in the liver environment.

Tregs are important in the gut-liver immune axis. CD4+ CD25+ Tregs suppress the activation of CD4+ T cells by LSECs, Kupffer cells, or hepatocytes. Because this process can be overcome by TLR4 activation, the interaction among Tregs, pathogens, and other liver cells determines the outcome of immune activation in the liver. Tregs can curb unwanted immune responses and regulate responses to the microflora and can play a role in a number of chronic inflammatory diseases of the gut. Tregs can prevent detrimental inflammatory responses against commensal organisms in the lower gut, thus guarding against inflammatory bowel diseases. Various subsets of T lymphocytes have been suggested to exhibit regulatory functions, including natural Tregs, induced Tregs, Tr1, and Th3 cells. These cells may be activated by cytokines, and their inductive phase may be antigen driven. Most CD4+ regulatory T cells (Tr1, Th3, and CD4+CD25+) are thought to interact with dendritic cells. Other subsets of Tregs, such as CD8+ TrE cells, may recognize antigens that are presented by intestinal epithelial cells.

CD4+CD25+ Tregs are considered to be instrumental in regulating immune responses in the mucosa. TGF-$\beta$ has emerged as one of the most important cytokines produced in the gut, and its interaction with CD4+CD25+ Tregs is key in maintaining a balance between T-cell immunity and tolerance. Expression of a stable, form of $\beta$-catenin in CD4+ CD25+ Tregs results in a marked enhancement of the survival of these cells. The number of Tregs necessary for protection against inflammatory bowel disease could be substantially reduced when stable $\beta$-catenin-expressing CD4+CD25+ Tregs are used. IL-35 is an inhibitory cytokine produced by Treg cells and is required for maximal suppressive activity. As discussed below, the present inventors have demonstrated modulation of CD4+ CD25+ Treg cells with compositions according to the present invention, Foxp3+ Tregs are important for the establishment and maintenance of mucosal tolerance. Cytokine deprivation-induced apoptosis is a prominent mechanism by which Tregs inhibit effector TCR. As such, CD4+CD25+Foxp3+ Tregs induce apoptosis in effector CD4+ T cells.

TGF-β secretion by Th3 or other Treg cells is considered to be a key factor in oral tolerance. TGF-β-producing cells are crucial for oral tolerance and may be master regulators of most of the mechanisms triggered by antigen feeding. Latency-associated peptide (LAP) is the amino-terminal domain of the TGF-β precursor peptide, and remains non-covalently associated with the TGF-β peptide after cleavage and forms the latent complex. The presence of membrane-bound TGF-β or LAP on the surface of Tregs has linked TGF-β with the suppressive function of Tregs. TGF-β-secreting Th3 cells and CD8+ regulatory cells have been associated with oral tolerance and are dependent on TGF-β. As discussed below, the present inventors have demonstrated modulation of LAP+ and LAP− Treg cells with compositions according to the present invention, A membrane-bound form of TGF-β containing LAP has been described. LAP+CD4+ cells mediate suppression in the gut via a TGF-β-dependent mechanism. The present inventors have shown that TGF-β-dependent Tregs that express surface LAP are induced/promoted by oral administration of anti-LPS antibodies. TGF-β may induce the differentiation of IL-10-producing cells, indicating that cross-talk between different cytokine-producing Tregs may exist in oral tolerance induction, for example inducing CD4+CD25-LAP+ Tregs, which suppress autoimmunity.

Subsets of CD8+ lymphocytes are also involved in tolerance induction. Intestinal epithelial cells (IECs) can promote CD8+ Tregs to process and present antigen to T cells. T cells activated by IECs are suppressive in function, whereas IECs can induce the proliferation of a small fraction of CD8+ peripheral T cells. The CD8+CD28− subset of IEC-activated CD8+ T cells expresses CD101 and CD103, interacts with IECs through gp180, and possesses a regulatory function. CD8+ T cells with regulatory activity are present in the LP of normal, healthy individuals, but not in patients with inflammatory bowel disease (IBD), indicating that these cells play an active role in mucosal tolerance. "Antigen-cross-presentation," or the possibility that molecules presented by professional APCs can leak into the major histo-compatibility complex class I (MHC-I) pathway and are presented to CD8+ T cells, is a possible mechanism. Alternatively, "cross-priming" of CD8+ by APCs associated with CD4+ T-cell activation may be a mechanism responsible for suppression. CD8+ T cells play a regulatory role via secretion of TGF-β. Antigen-primed CD8+ T-cell populations produce IL-4 or IL-10, and may be associated with tolerance induction.

Accordingly, in another aspect, the present invention provides a composition comprising a mammalian anti-LPS enriched colostrum-derived immunoglobulin preparation for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+NK1.1+ cells in the liver, decreasing CD25+ LAP− T cells in the liver, increasing CD25+ LAP+ T cells in the liver, inducing CD4+ CD25+ LAP− T cells in the spleen, inducing CD4+ CD25+ LAP− T cells in adipose tissue.

Adipocytes are the cells that primarily compose adipose tissue, specialized in storing energy as fat. There are two types of adipose tissue, white adipose tissue (NAT) and brown adipose tissue (BAT), which are also known as white fat and brown fat, respectively, and comprise the two types of fat cells. White fat cells or monovacuolar cells contain a large lipid droplet surrounded by a layer of cytoplasm. The nucleus is flattened and located on the periphery. A typical fat cell is 0.1 mm in diameter with some being twice that size and others half that size. The fat stored is in a semi-liquid state, and is composed primarily of triglycerides and cholesteryl ester. White fat cells secrete resistin, adiponectin, and leptin. Brown fat cells or pluri vacuolar cells are polygonal in shape. Unlike white fat cells, these cells have considerable cytoplasm, with lipid droplets scattered throughout. The nucleus is round, and, although eccentrically located, it is not in the periphery of the cell. The brown color comes from the large quantity of mitochondria.

As shown, by the Examples, the compositions of the invention, significantly decreased the serum levels of triglycerides, ALT, AST and glucose. Therefore, according to one embodiment, the pharmaceutical composition of the invention leads to at least one of a decrease in the serum levels of cholesterol, triglycerides, ALT, AST and glucose and a decrease in insulin resistance in a subject suffering of a liver disorder or an immune-related disorder, for example, Metabolic syndrome. Wherein indicated decease, reduction, inhibition, it is meant that the composition of the invention leads to a reduction of about 5% to 99% of the serum level of any one of triglycerides, ALT, AST and Glucose, in a subject suffering of an-immune-related disorder. More specifically, such reduction may be a reduction of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control. Wherein indicated increase, elevation, enhancement, induction, it is meant that the composition of the invention leads to induction, or increase of about 5% to 99%. More specifically, such increase may be an. increase of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control.

According to one specific embodiment the composition of the invention may be used for preventing and/or treating autoimmune disease for example, Metabolic Syndrome or any of the conditions comprising the same, any condition associated with, caused by, linked to or believed to have an impact on metabolic syndrome, for example, at least one of dyslipoproteinemia (hypertriglyceridemia, hypercholesterolemia, low HDL-cholesterol), obesity, NIDDM (non-insulin dependent diabetes mellitus), IGT (impaired glucose tolerance), blood coagulability, blood fibrinolysis defects and hypertension.

The Metabolic Syndrome is characterized by a group of metabolic risk factors in one person including:
 Abdominal obesity (excessive fat tissue in and around the abdomen);
 Atherogenic dyslipidemia (blood fat disorders—high triglycerides, low HDL cholesterol and high LDL cholesterol—that foster plaque buildups in artery walls); *Elevated blood pressure; *Insulin resistance or glucose intolerance; *Pro thrombotic state (e.g., high fibrinogen or plasminogen activator inhibitor—1 in the blood); and *Proinflammatory state (e.g., elevated C-reactive protein in the blood). People with the metabolic syndrome are at increased risk of coronary heart disease and other diseases related to plaque buildups in artery walls (e.g., stroke and peripheral vascular disease) and type 2 diabetes.

More particularly, the composition of the invention is intended for the treatment of dyslipoproteinemia, which may include hypertriglyceridemia, hypercholesterolemia and low HDL-cholesterol, obesity, NIDDM (non-insulin dependent diabetes mellitus type 2), IGT (impaired glucose tolerance), blood coagulability, blood fibronolysis defects and hypertension.

According to one specific embodiment, the immunomodulatory composition of the invention may be used for treating diabetes, particularly, Type 2 diabetes. Diabetes mellitus, often simply diabetes, is a syndrome characterized by disordered metabolism and inappropriately high, blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision. These symptoms are likely absent if the blood sugar is only mildly elevated.

The World Health Organization recognizes three main forms of diabetes mellitus: Type 1, Type 2, and gestational diabetes (occurring during pregnancy), which have different causes and population distributions. While, ultimately, all forms are due to the beta cells of the pancreas being unable to produce sufficient insulin to prevent hyperglycemia, the causes are different. Type 1 diabetes is usually due to autoimmune destruction of the pancreatic beta cells. Type 2 diabetes is characterized by insulin resistance ih target tissues, this causes a need for abnormally high amounts of insulin and diabetes develops when the beta cells cannot meet this demand. Gestational diabetes is similar to type 2 diabetes in that it involves insulin resistance, hormones in pregnancy may cause insulin resistance in women genetically predisposed to developing this condition.

Acute complication of diabetes (hypoglycemia, ketoacidosis or nonketotic hyperosmolar coma) may occur if the disease is not adequately controlled. Serious long-term complications include cardiovascular disease (doubled risk), chronic renal failure, retinal damage (which can lead to blindness), nerve damage (of several kinds), and microvascular damage, which may cause impotence and poor healing. Poor healing of wounds, particularly of the feet, can lead to gangrene, which may require amputation.

According to another embodiment, the immunomodulatory composition of the invention may be used for the treatment of Type 1 diabetes. Type 1 diabetes mellitus is characterized by loss of the insulin-producing beta cells of the islets of Langerhans in the pancreas, leading to a deficiency of insulin. The main cause of this beta cell loss is. a T-cell mediated autoimmune attack.

In yet another embodiment, the pharmaceutical composition of the invention may be used for the treatment of an autoimmune disorder. Examples of autoimmune disorders include, but are not limited to, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The oral compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

According to a specifically preferred embodiment, an autoimmune disease treated by the composition of the invention may be any one of rheumatoid arthritis, type 1 diabetes, type 2 diabetes, artherosclerosis, asthma, acute and chronic graft versus host disease, systemic lupus erythmatosus, scleroderma, multiple sclerosis, inflammatory bowel disease, psoriasis, uvietis, thyroiditis and immune mediated hepatitis.

According to another embodiment, the composition of the invention may be used for the treatment of MS. Multiple Sclerosis (MS) is typically characterized clinically by recurrent or chronically progressive necrologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Thus, the invention includes compositions and methods of treating, delaying or preventing the onset of MS, by orally or mucosally administering the colostrum-derived immunoglobulin preparation of the invention. Included are methods wherein a subject who has or is at risk of having MS is orally administered with the composition of the invention.

According to another preferred embodiment, the composition of the invention may be used for the treatment of RA. Rheumatoid arthritis (RA) is the most common chronic inflammatory arthritis and affects about 1% of adults, it is two to three times more prevalent in women than in men. RA may begin as early as infancy, but onset typically occurs in the fifth or sixth decade.

Diagnosis may be made according to the American Rheumatism Association Criteria for the so Classification of Rheumatoid Arthritis. A therapeutically effective amount will cause an improvement in one or more of the following: the number of inflamed joints, the extent of swelling, and the range of joint motion. Laboratory measurements (e.g., ESR and hematocrit value) and assessments of subjective features (e.g., pain and morning stiffness) can also be made. The invention also includes methods of treating autoimmune arthritis, e.g., RA, in a subject by administering to the subject a therapeutically effective amount of composition of the invention comprising colostrum-derived immunoglobulin preparations.

The compositions of the invention described herein can also be used to treat or prevent graft rejection in a transplant recipient. For example, the compositions can be used in a wide variety of tissue and organ transplant procedures, e.g., the compositions can be used to induce central tolerance in a recipient of a graft of cells, e.g., stem cells such as bone marrow and/or of a tissue or organ such as pancreatic islets, liver, kidney, heart, lung, skin, muscle, neuronal tissue, stomach, and intestines. Thus, the new methods can be applied in treatments of diseases or conditions that entail cell, tissue or organ transplantation (e.g., liver transplantation to treat hypercholesterolemia, transplantation of muscle cells to treat muscular dystrophy, or transplantation of neuronal tissue to treat Huntington's disease or Parkinson's disease).

According to another embodiment, the composition of the invention may modulate the Th1/Th2, Th3 balance towards an anti-Th2, Trl/Th3 response in a subject suffering from IBD. Therefore, according to this embodiment, the composition of the invention is intended for treating IBD. Inflammatory bowel diseases (IBD) are common gastrointestinal disorders that can be perceived as being the result of a dysbalance between Th1-pro-inflammatory, and Th2-anti-inflammatory subtypes of immune responses.

Patients with IBD have antibodies against components of colon cells and several different bacterial antigens. These antigens gain access to the immune system as a consequence of epithelial damage. Abnormalities of T cell-mediated immunity, including coetaneous anergy and diminished responsiveness to T cell stimuli, have also been described in these patients. In addition, changes in mucosal cell mediated immunity were identified, including increased concentrations of mucosal IgG cells and changes in T cells subsets, suggesting antigen stimulation.

In yet another preferred embodiment, the composition of the invention may be used for the treatment of atherosclerosis. Atherosclerosis is a slowly progressive disease characterized by the accumulation of cholesterol within the arterial wall. The atherosclerotic process begins when LDL-C becomes trapped within the vascular wall. Oxidation of the LDL-C results in the bonding of monocytes to the endothelial cells lining the vessel wall. These monocytes are activated and migrate into the endothelial space where they are transformed into macrophages, leading to further oxidation of LDL-C. The oxidized LDL-C is taken up through the scavenger receptor on the macrophage leading the formation of foam cells. A fibrous cap is generated through the proliferation and migration of arterial smooth muscle cells, thus creating an atherosclerotic plaque. Lipids depositing in atherosclerotic legions are derived primarily from plasma apo B containing lipoproteins. These include chylomicrons, LDL-C, IDL, and VLDL. This accumulation forms bulky plaques that inhibit the flow of blood until a clot eventually forms, obstructing an artery and causing a heart attack or stroke.

Alternatively, the immunoglobulin preparation used by the composition of the invention may recognize and bind at least one antigen specific for the treated disorder and may modulates immune-regulatory cells, specifically, regulatory T cells. Such modulation may results for example, in modulation of the Th1/Th2 cell balance toward a pro-inflammatory Th1 immune response thereby activating an immune response specifically directed toward said disorder.

It should be appreciated that the pro-inflammatory effect of the immunomodulatory composition of the invention may be achieved by activation or promotion of specific subsets of regulatory cells, antigen presenting cells or any type of cell-cell contact via direct or indirect activation, of cytokines, and/or chemokines.

According to this specific embodiment, modulation of the Th1/Th2, Th3 balance towards a pro-inflammatory Th1 response may be particularly applicable in immune related disorders having an undesired unbalanced anti-inflammatory Th2, Trl/Th3 response, for example, a malignant and non-malignant proliferative disorder, infectious disease, genetic disease and neurodegenerative disorders.

In another aspect, the present invention provides a use of an anti-LPS enriched immunoglobulin preparation in the manufacture of a medicament for the treatment and/or prophylaxis of a pathologic disorder. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the medicament is for the treatment and/or prophylaxis of liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

The medicament may further comprise an immunoglobulin preparation comprising immunoglobulins that recognize and bind at least one antigen specific for said pathologic disorder. The further immunoglobulin preparation may be derived from colostrum or from avian eggs.

In one embodiment, the medicament modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the medicament modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment, the medicament is for the treatment and/or prophylaxis of metabolic syndrome or non alcoholic steatohepatitis or both, the treatment and/or prophylaxis of diabetes, the treatment impaired glucose tolerance, such as decreasing glucose tolerance, decreasing serum insulin levels, decreasing hepatic triglyceride levels, or decreasing cholesterol levels.

In one embodiment, the medicament modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders, The medicament may further comprise a therapeutic agent, carrier or adjuvant and/or non-hyperimmune colostrum.

In one embodiment, the medicament is formulated for administration orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment the composition reduces or inhibits mucosal microbial translocation. In another embodiment the composition reduces or inhibits mucosal microbial translocation and thereby modulates immune activation.

In another aspect, the present invention provided a use of a mammalian anti-LPS enriched colostrum-derived immunoglobulin preparation in the manufacture of a medicament for modulating immune tolerance in a subject, or in another embodiment, a medicament for modulating oral tolerance in a subject.

In another aspect, the present invention provides the use of a mammalian anti-LPS enriched colostrum-derived immunoglobulin preparation in the manufacture of a medicament for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+CD25+ LAP+ T cells in stromal vascular cells, decreasing CD3+NK1.1+ cells in the liver, decreasing CD25+ LAP− T cells in the liver, increasing CD25+ LAP+ T cells in the liver, inducing CD4+ CD25+ LAP-T cells in the spleen, or inducing CD4+ CD25+ LAP− T cells in adipose tissue.

The anti-LPS enriched immunoglobulin preparation may be derived from colostrum or from avian eggs.

In one aspect, the present invention provides a method for the treatment and/or prophylaxis of a pathologic disorder comprising the step of administering to a subject in need thereof a therapeutically effective amount of a composition comprising an anti-LPS enriched immunoglobulin preparation. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the pathologic disorder is liver damage.

In another embodiment, the pathologic disorder is an immune-related disorder selected from the group consisting of autoimmune disease, non alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum or from avian eggs.

In another embodiment, the composition modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

In another embodiment, the composition modulates the Th1/Th2, Trl/Th3 cell balance toward an anti-inflammatory Th2, Trl/Th3 immune response thereby inhibiting an immune response specifically directed toward said disorder, and wherein said composition is for the treatment of any one of an autoimmune disease, non alcoholic steatohepatitis, fatty liver, atherosclerosis, metabolic syndrome and any disorder associated therewith selected from diabetes type 2, insulin resistance, obesity and overweight.

In another embodiment the pathologic disorder is metabolic syndrome or non alcoholic steatohepatitis or both.

In another embodiment, the pathologic disorder is diabetes. In another embodiment, the pathologic disorder is impaired glucose tolerance.

In another embodiment, the method decreases glucose tolerance, decreases serum insulin levels, decreases hepatic triglyceride levels, or decreases cholesterol levels.

In another embodiment, the method modulates the Th1/Th2, Trl/Th3 cell balance toward a pro-inflammatory Th1/Th2 immune response thereby enhancing an immune response specifically directed toward said disorder, and wherein said composition is for the treatment of infectious diseases, and proliferative disorders, In another embodiment, the composition further comprises non-hyperimmune colostrum and/or a therapeutic agent, carrier or adjuvant.

The composition may be administered orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment, the method reduces or inhibits mucosal microbial translocation. In another embodiment, the method reduces or inhibits mucosal microbial translocation and thereby modulates immune activation.

In another aspect, the present invention provides a method for modulating immune tolerance in a subject comprising the step of administering to a subject in need thereof a therapeutically effective amount of a composition comprising a mammalian anti-LPS enriched colostrum-derived immunoglobulin preparation. Alternatively, the method may be for modulating oral tolerance.

A method for inducing CD4+ CD25+ T cells in the liver of a subject comprising the step of administering to a subject in need thereof a therapeutically effective amount of a composition comprising a mammalian anti-LPS enriched colostrum-derived immunoglobulin preparation. In another embodiment, the method may be for inducing CD4+ CD25+ LAP– T cells in the liver, CD45+ LAP+ T cells in the liver, inducing CD3+LAP+ T cells in the liver, inducing CD45+ LAP+ T cells in the spleen, inducing CD8+LAP+ T cells in the spleen, inducing CD3+ LAP+ T cells in the spleen, inducing CD8+CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+NK1.1+ cells in the liver, decreasing CD25+ LAP– T cells in the liver, decreasing CD25+LAP+ T cells in the liver, inducing CD4+ CD25+ LAP– T cells in the spleen, or inducing CD4+ CD25+ LAP– T cells in adipose tissue.

In a further aspect, the present invention provides a method for the treatment and/or prophylaxis of a pathologic disorder. The method of the invention comprises the step of administering to a subject in need thereof a therapeutically effective amount of a mammalian colostrum-derived anti-LPS enriched immunoglobulin preparation or of a composition comprising the same. It should be noted that the immunoglobulin preparation or any fractions thereof recognizes and binds LPS and any fragments thereof. According to an optional embodiment, the method of the invention comprises the step of administering a combined composition of anti-LIDS enriched immunoglobulin preparation of the invention with at least one immunoglobulin preparation comprising immunoglobulins recognizing at least one antigen specific for said disorder, thereby activating or inhibiting an immune response specifically directed toward said disorder.

According to one embodiment, the colostrum-derived, milk or milk product/s-derived anti-LPS enriched immunoglobulin preparation or any fragment or mixture, combination, or any composition thereof, used by the method of the invention comprises a monomeric, dimeric and multimeric immunoglobulin selected from the group consisting of IgG, IgA and IgM and any fragments thereof, preparations, mixtures and compositions thereof. More specifically, the immunoglobulin preparation used by the method of the invention may specifically comprise IgG, particularly, IgG1 and/or IgG2 and any fragments thereof. Alternatively or additionally, the immunoglobulin preparation used by the method of the invention may specifically comprise secretory dimeric IgA.

According to another embodiment, the method of the invention may use a composition or combined composition comprising colostrum-derived anti-LPS enriched immunoglobulin preparation. Such composition optionally further comprises colostrum component/s, preferably, alarmins, defenensins, colostrinin, or any glycolipids, carbohydrates or any preparations, mixtures and combinations thereof, or any other adjuvant/s. It should be noted that the present invention further provides the use of colostrum or any colostrum-derived preparations for enhancing an immunomodulatory effect of an immunomodulatory therapeutic agent. In one specific embodiment, the composition or combined composition used by the method of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

In yet another embodiment, the anti-LPS enriched immunoglobulin preparation or any other immunoglobulin preparation used by the invention may be obtained from a mammal, preferably a cow, immunized with LPS and optionally, in addition, with at least one antigen or a mixture of at least two antigens specific for a disorder to be treated.

According to one embodiment, the method of the invention comprises the step of administering to said subject a therapeutically effective amount of a mammalian anti-lipopolysaccharide (LPS) enriched colostrum-derived immunoglobulin preparation or any composition comprising the same. It should be noted that such method may be particularly applicable for the treatment, prevention and prophylaxis of acute or chronic liver disease, cirrhosis and any disease or complication associated therewith.

More specifically, acute or chronic liver disease, cirrhosis and any disease or complication associated therewith is at least one of hepatic encephalopathy, spontaneous bacterial peritonitis (SBP), ascitess, cirrhosis associated hyperdynamic circulation, hepatorenal syndrome, hepatopulmonary syndrome, portopulmonary hypertension, variceal bleeding, adrenal insufficiency and altered level of consciousness.

It should be noted that these complications may results from chronic HCV infection, alcoholic hepatitis, chronic HBV, non alcoholic steatoheaptitis, drug induced liver injury, or any other cause of acute or chronic liver disease.

According to one optional embodiment, the invention provides a method for treating immune-related disorders. According to this specific embodiment, the method of the invention comprises the step of administering to said subject a therapeutically effective amount of a combination of anti-LPS enriched immunoglobulin preparation with at least one colostrum-derived immunoglobulin preparation comprising immunoglobulins that recognize and bind at least one antigen specific for said pathologic disorder, or of a combined composition comprising the same and optionally an additional therapeutic agent or any carrier and adjuvant.

According to this embodiment, the combination used by the invention modulates regulatory T cells leading to modulation of the Th1/Th2, Trl/Th3 cell balance toward an anti-inflammatory Th2, Trl/Th3 immune response or a pro-inflammatory Th1 immune response thereby inhibiting or activating an immune response specifically directed toward said disorder.

According to another embodiment, the method of the invention may be particularly applicable or treating an immune-related disorder, for example, autoimmune disease, non alcoholic steatohepatitis, fatty liver, metabolic syndrome and any disorder associated therewith, infectious disease, and proliferative disorder.

In another embodiment, the present invention provides a method of treating impaired glucose tolerance.

In another embodiment, the present invention provides a method of decreasing glucose tolerance.

In another embodiment, the present invention provides a method of decreasing serum insulin levels In another embodiment, the present invention provides a method of decreasing hepatic triglyceride levels.

In another embodiment, the present invention provides a method of decreasing cholesterol levels.

It should be noted that the method of the invention is for treatment of acute complications, for preventing the development and/or the recurrence of these complications.

According to one embodiment, the combined composition used by the method of the invention leads to modulation of the Th1/Th2, Trl/Th3 cell balance toward an anti-inflammatory Th2, Trl/Th3 immune response thereby inhibiting an immune response specifically directed toward said disorder. According to this specific embodiment, such composition may be applicable in the treatment of any one of an autoimmune disease, non alcoholic steatohepatitis, fatty liver, atherosclerosis, metabolic syndrome and any disorder associated therewith for example, diabetes type 2, insulin resistance, obesity and overweight.

Alternatively, the combined composition used by the method of the invention may lead to modulation of the Th1/Th2, Trl/Th3 cell balance toward a pro-inflammatory Th1/Th2 immune response thereby enhancing an immune response specifically directed toward said disorder. According to this specific embodiment, such composition may be applicable in the treatment of infectious disease, and proliferative disorder.

According to one embodiment, the method of the invention may be specifically applicable for treating viral disease including HCV, HBV, CMV, and EBV.

In an even further embodiment of said method of the invention, the anti-LPS-enriched immunoglobulin preparation, or any composition comprising the same, is to be administered orally or by inhalation as an aerosol, or by intravenous, intramuscular, subcutaneous, intraperitoneal, perenteral, transdermal, intravaginal, intranasal, mucosal, sublingual, topical, rectal or subcutaneous administration, or any combination thereof.

According to a specifically preferred embodiment, the method of the invention is specifically suitable for the treatment of a mammalian subject. "Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

"Treatment" refers to therapeutic treatment. Those in need of treatment are mammalian subjects suffering from an immune-related disease. By "patient" or "subject in need" is meant any mammal for which administration of the immuno modulatory composition of the invention is desired, in order to prevent, overcome or slow down such infliction.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

As indicated above, generally, the dosage of needed to achieve a therapeutic effect will depend not only on such factors as the age, weight and sex of the patient and mode of administration, but also on the degree of disease progression and the potency of the particular derivative being utilized for the particular disorder of disease concerned.

It should be appreciated that the prevention or reduction of the risk of developing an immune-related disease is also encompassed within the scope of the invention. Such method may comprise the administration of a prophylactically effective amount of the composition of the invention or of the active ingredients comprised within such composition, to a person at risk of developing a disease.

The term "prophylactically effective amount" is intended to mean that amount of a pharmaceutical combined composition that will prevent or reduce the risk of occurrence of the biological or medical event that is sought to be prevented in a tissue, a system, animal or human by a researcher, veterinarian, medical doctor or other clinician.

It should be noted that for the method of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1: Preparation of Colostrum-Derived Anti-LPS Enriched Preparations

The product 'BioGARD' is a proprietary colostrum preparation supplied by Anadis Limited. Each Anadis BioGARD tablet is an uncoated 1.2 g oral tablet, which contains 600 mg of freeze-dried Bovine Colostrum Powder (BCP), in combination with excipients. The active substance in BioGARD tablets is freeze-dried bovine colostrum powder (BCP) milked from commercial dairy cowherds. The cows in these herds, as well as being vaccinated for routine cattle pathogens, have been vaccinated with a proprietary Anadis vaccine against the outer cell wall antigens of multiple strains of *E. coli* bacteria, a major organism in human gut microflora. Anadis BCP is a high-protein (>80%), lactose- and fat-reduced natural product derived from the first milking of commercial dairy cows collected after calving. It is presented before tableting as a concentrated, freeze dried powder.

Anadis BCP contains approximately 40% antibodies (immunoglobulins) in the dry powder. The immunoglobulins in BioGARD's BCP have high binding activity against the Lipopolysaccharide (LPS) of Gram-negative bacteria. Binding of LPS is assayed by Anadis using a standardized ELISA and immuno-blotting detection systems.

Three dairy cows are immunized with a mixture of LPS antigens. The antigen vaccine was administered during the last eight weeks of gestation. Colostral milk was collected during the first two days of lactation. The milk fat was removed and skim milk was pasteurized at 56° C. for 30 minutes and then coagulated by renetting as in Hilpert, Human Milk Banking 1984. After removal of milk curd containing casein, the whey was centrifuged and the fine precipitate was discarded. An equal volume of saturated ammonium sulfate solution was slowly added to the supernatant with continuous mixing as in Brandon et al. [Brandon et al., Aust. J. Exp. Biol. Med. Sci. 49:613 (1971)]. After centrifugation the resulting precipitate was saved and the supernatant containing lactose and salts was discarded.

The precipitate was dissolved in 0.01M TRIS-HCl buffer pH 8 containing 0.32M NaCl (30% of original volume). This solution was extensively dialyzed against five volumes of the same buffer using an Amicon spiral membrane SIY30 cartridge. The antibody solution was then concentrated to 10%, snap frozen and freeze dried. ∎

Production of Antibody Fragments from Colostrum.

Antibody fragments are prepared according to modified method based on the methods described by Jones R. G. A. and Landon J. [Jones R. G. A. and Landon J. J. Immunol. Methods 263: 57-74 (2002)]. Briefly, an equal volume of 0.2M Sodium Acetate buffer pH 4.0, is added to a colostrum pool obtained from immunized animals as described above. The pH of the diluted colostrum pool has been adjusted to 4.6 and incubated at 37° C. for two hours to precipitate caseins. Subsequently, colostrum is centrifuged and filtered (0.45 µm) to remove casein. The pH of the resultant colostral whey has been adjusted to pH 4.0, followed by addition of Pepsin (Enzyme Solutions with 1:15,000 activity) at 5.0% w/w and incubation for twenty hours at 45° C. Pepsin digestion has been stopped by addition of 0.5 vol. of IM Tris pH8 and cooling the reaction mix to 4° C. The pH of the reaction is adjusted to pH to 7.0 and the F(ab')2 mix is concentrated using 30 kD ultra-filtration membrane and dia-filtrate vs. >50 volumes of 20 mM sodium phosphate/ 150 mM NaCl pH 6.0 buffer. Small peptides are then removed and the resulting solution containing F(ab')2, Pepsin and Large Peptides was then subjected to Q Sepharose Anion Exchange column that Binds Pepsin and acidic aggregates. To obtain purified F(ab')2, the remaining Fc and undigested Ig are removed from the F(ab')2 (mixed with remaining large Peptides and undigested Ig), by Protein G or by Prometic Mabsorbent AlP chromatography.

Preparation of Fab' by 2-mercaptoethylamine (MEA). To prepare Fab[1], 50 ul (1/9 vol.) of 0.1M 2-mercaptoethylamine (MEA) in 0.1M sodium phosphate buffer pH 6.0, containing freshly prepared 5 mM EDTA-disodium, are added to 0.1-3.0 mg of F(ab')2 in 0.45 ml of 0.1 M sodium phosphate buffer, pH 6.0. The mixture is then incubated at 37° C. for 90 mins. Subsequently, the reaction mixture is applied on a PD-10 column, or a suitable G25 column, to remove the excess MEA. 0.1M sodium phosphate (pH 6.0, with 5 mM EDTA-disodium) is used as the running buffer. The first protein peak which contains Fab', is collected and used for treating the corresponding different indications as indicated herein below.

For preparation of the anti-LPS enriched immunoglobulin preparation, colostrum was collected from approximately 200 commercial diary cowherds, The cows in these herds, as well as being vaccinated for routine cattle pathogens, have been vaccinated with a proprietary Anadis vaccine against the outer cell wall antigens of multiple strains of *E. coli* bacteria, a major organism in human gut microflora. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

Example 2: Use of Colostrum-Derived Anti-LPS Enriched Immunoglobulin Preparations in the Treatment of Hepatitis For immune mediated hepatitis model, eleven to twelve weeks old male C57/bl mice are tail vein injected with a dose of 500 µglinouse (approximately 15 mg/kg) of Con A (MP Biomedicals, USA) which is dissolved in 50 mM Trig pH 7, 150 mM NaCl, 4 mM $CaCl_2$, known to induce hepatitis. Animals of all tested groups are orally administered using different concentrations and preparations of specific antibodies, or the BioGARD preparation described in experimental procedures, as compared to untreated controls. Animals of all tested groups are followed for the following parameters: serum aspartate aminotransferase (AST) and alanine aminotransferase (ALT) levels, histological examination of liver specimens, FACS analysis of intrahepatic and intrasplenic lymphocytes for NKT markers, measurement of serum cytokine levels and Western blot analysis for the expression of the transcription factors STAT 1, 4 and 6 and NFκB and are compared to control groups.

Example 3: Oral Administration of Colostrum Enriched with Anti LPS Antibodies

For preparation of the anti-LPS enriched immunoglobulin preparations, colostrum was collected from approximately 200 commercial diary cowherds, The cows in these herds, as well as being vaccinated for routine cattle pathogens, have been vaccinated with a proprietary Anadis vaccine against the outer cell wall antigens of multiple strains of *E. coli* bacteria, a major organism in human gut microflora. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

Two compositions comprising anti-LPS enriched colostrum-derived immunoglobulin preparations were prepared by vaccinating pregnant cows with bacterial cell wall antigens (e.g. LPS) prepared from a number of *E. coli* strains to produce highly concentrated antibodies (including IgG) to LPS in colostrum. In the following examples, this composition is denoted by 'HIBC'.

A second preparation was prepared by vaccinating pregnant cows with a vaccine comprising a number of *E. coli* strains, and also enriched for LPS and other surface antigens, to produce highly concentrated antibodies (including IgG) to LPS in colostrum. IgG was then purified from this colostrum preparation. In the following examples, this composition is denoted by 'T-IgG'

TABLE 1

Experimental design

| Group | DDW | Colostrum preparation (3 mg) | Administration |
|---|---|---|---|
| A N = 10 | 30 ml | — | PO |
| B N = 10 | — | 30 ml | PO |

Experimental Groups.

Two groups of mice (Table 1) were studied. Mice (10 per group) were fed (perorally) daily for 7 days with 30 μl of water (control, group A) or 30 ul (approximately 3 mg) of anti-LPS enriched colostrum-derived immunoglobulin preparation (group B) which was dissolved in water. After 7 days mice were sacrificed. On sacrifice day, cardiac blood was collected by standard techniques then serum was obtained for future purposes.

Animals.

Naïve C57Bl/6 mice (age 11-12 weeks) were used. Mice were obtained from Harlan Laboratories (Jerusalem, Israel) and were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Liver:

After harvesting the livers are transferred to ice cold PBS cut, minced and homogenized using a dounce homogenizer with 9 ml of sterile cold lysis buffer 1, divided into eppendorff tubes (1.5 ml in each tube), and kept on ice for 30 minutes, followed by sonication (five cycles of 25 seconds) and centrifugation (at 4° C., 14,000 RPM for 15 minutes). The supernatants are collected into one tube, sampled for protein quantification using the Bradford technique and stored at −20° C.

Spleen.

Following excision the spleens are minced on cells dissociation grids (60 mesh) in RPMI 1640 medium, centrifuged (at 4° C., 1,400 RPM for 10 minutes) and the supernatant discarded; Red blood cells are lysed by adding 1 ml of cold RBC lysis buffer (155 mM ammonium chloride), followed by rinsing three times with cold PBS and centrifugation.

Preparation of Cytosolic Fraction of Spleen.

Cold buffer 1 was added to the pellet of spleen cells (in a 6:1 ratio of buffer to pellet) and the cells are divided into 2 ml vials, kept on ice for 30 minutes, sonicated five times (25 seconds each time), and centrifuged (at 4° C., 14,000 RPM for 15 minutes); Supernatants are then collected from all vials, sampled for protein quantification, and kept at −20° C.

Preparation of Membranal Fraction of Spleen.

The remaining pellet from the above mentioned centrifugation step of the cytosolic fractionation is added with 100-250 ml of buffer 2, agitated for 30 minutes at 4° C., and centrifuged (at 4° C., 14,000 RPM for 15 minutes). The supernatants are then collected from all vials, sampled for protein quantification and kept at −20° C.

Isolation of Splenic and Hepatic Lymphocytes for Determination of T Cell Subpopulations.

Mice of different experimental models are sacrificed on the days indicated. Splenic lymphocytes and NKT cells are isolated and red blood cells removed. Intrahepatic lymphocytes are isolated as follows: After cutting the inferior vena cava above the diaphragm, the liver is flushed with cold PBS until it become pale, followed by removal of connective tissue and gall bladder. Livers and spleens Were kept in RPMI-1640+FCS. Then spleens were crushed through a 70 μm nylon cell strainer (Falcon) and centrifuged (1250 rpm for 7 min) for the removal of cell debris. Red blood cells were lysed with 1 ml of cold 155 mM ammonium chloride lysis buffer and immediately centrifuged (1250 rpm for 3 min). Splenocytes were then washed and resuspended with 1 ml RPMI+FCS. Remains of connective tissue were removed. The viability by trypan blue staining was above 90%. For intrahepatic lymphocytes, livers were first crushed through a stainless mesh (size 60, Sigma) and the cell suspension was placed in a 50-ml tube for 5 min to enable cell debris to descend. 10 ml of Lymphoprep (Ficoll, Axis-Shield PoC AS, Oslo, Norway) was slowly placed under the same volume of cell suspension in 50-ml tubes. The tubes were then centrifuged at 1800 rpm for 18 min. Cells in the interface were collected and moved to new tubes which were centrifuged again at 1800 rpm for 10 min, to obtain a pellet of cells depleted of hepatocytes to a final volume of 250 μl. Approximately $1 \times 10^6$ cells/mouse liver, were recovered. Cells viability was detected by trypan blue staining.

Isolation of Adipocytes.

Adipose tissue (visceral fat pads) was minced and incubated in Krebs-Ringer bicarbonate buffer (3 mL/g adipose tissue) containing 10 mM glucose and 2.5% bovine serum albumin, incubated with 840 U/g collagenase type I (Sigma, Rehovot, Israel) at 37° C. with gentle agitation for 1 hour. Then filtered twice through chiffon mesh (100 μm) and centrifuged 50×g for 5 minutes. Floating adipocytes were then separated from the pellet of stromal vasculature (SV) fraction. The lower fraction was removed and centrifuged at 200×g for 5 min to pellet the SV cells. Cell number was then counted.

Flow Cytometry Analysis (FACS) for Determination of Different Subsets of Lymphocytes.

Following lymphocyte isolation from blood, spleen or any organ, triplicates of $2-5 \times 10^5$ cells/500 μL PBS are placed in Falcon 2052 tubes, incubated with 4 mL of 1% BSA for 10 minutes, and centrifuged at 1400 rpm for 5 minutes. Cells are re-suspended in 10 μL FCS with 1:20 labeled (FITC, APC or PE-labeled) primary antibodies directed to the following lymphocyte markers: CD3, CD4, CD8, NKl.1, CD25, FOX p3, LAP cells, IL-17, Annexiin and surface markers for T cell activation. Cells-antibody mixtures are mixed every 10 minutes for 30 minutes. Cells are isolated using anti-CD3 and anti-CD4, anti-CD8, and anti-NKl.1, respectively. Cells are washed twice in 1% BSA and kept at 4° C. until reading. For the control group, only 5 μL of 1% BSA are added. Surface staining was performed by incubating cells with antibodies and anti-CD 16/32 (blocks Fc, eBioscience) at 4° C. in FACS buffer containing PBS and 0.5% BSA, for 30 min. Cells were further washed twice with FACS buffer, resuspended in FACS buffer, and analyzed by flow cytometry. Analytical cell sorting is performed on $1\times10^4$ cells from each group with a fluorescence-activated cell sorter (FACStar Plus, Becton Dickinson). Appropriate isotype controls were used in all experiments. Analysis was performed using a FACSCalibur instrument (Becton Dickinson, San Jose, Calif.). Only live cells were counted, and background fluorescence from non-antibody-treated lymphocytes was subtracted. Gates were set on forward- and side-scatters to exclude dead cells and red blood cells. Data was analyzed by the Consort 30 two-color contour plot (Becton Dickinson, Oxnard, Calif., USA) or Cell Quest programs.

FACS Analysis for Determination of NKT Lymphocyte Percentage.

Immediately after lymphocyte isolation, triplicates of $2-5\times10^4$ cells/500 µl PBS are placed into Falcon 2052 tubes, incubated with 4 ml of 1% BSA for 10 minutes, and centrifuged at 350 g for 5 minutes. For determination of the percentage of NKT lymphocytes, anti-CD3 and anti DX5 antibodies are used (Pharmingen, USA). Analytical cell sorting is performed on $1\times10^4$ cells from each group with a fluorescence-activated cell sorter (FACSTAE plus, Becton Dickinson). Only live cells are counted, and background fluorescence from non-antibody-treated lymphocytes is subtracted. Gates are set on forward- and side-scatters to exclude dead cells and red blood cells. Data is analyzed with the Consort 30 two-color contour plot program (Becton Dickinson, Oxnard, Calif.), or the CELLQuest 25 program.

Isolation of NKT Lymphocytes.

Cell separation is performed using Magnetic Cell Sorting (MACS, Miltenyi Biotec, Germany) according to the manufacturer's instructions. Anti-CD 3 and anti-DX5 magnetic beads are used for separation of NKT lymphocytes. Beads are removed between the two steps according to the manufacturer's instructions. Above 95% accuracy is achieved by FACS analysis of cells.

Hepaotcellular Damage.

Liver injury was evaluated by serum aspartic transaminase (AST) and alanine aminotransferase (ALT) activities, which were determined with an automatic analyzer.

Measurements.

The following parameters were measured: blood glucose, total cholesterol and triglyceride. Blood glucose values were measured with a standard glucometer. Plasma triglyceride and total cholesterol values were measured by a clinical chemistry analyzer Reflovet Plus machine (Roche Diagnostics, GmbH, Mannheim, Germany).

Glucose Tolerance Test.

Mice were subjected to a glucose tolerance test (GTT) on day 30 after overnight fasting. Glucose was administered orally (1.25 g per kg). Serum glucose measurements were performed on tail-vein blood every 15 minutes for 3 hours. Glucose levels were measured by a standard glucometer.

Glucose Morning Levels.

Study groups were also evaluated by resting (non-fasting) morning glucose levels.

Cytokine Determination.

IFN-γ and TGF-β levels were determined on serum by "sandwich" ELISA, using commercial kits (Quantikine, R&D Systems, Minneapolis, Minn., USA). Serum insulin was also determined by "sandwich" ELISA, using the commercial kit of Mercodia AB (Uppsala, Sweden) according to the manufacturer's instructions.

Statistics.

Statistical significance was determined by unpaired, two-tailed Student's t test and only values of p<0.05 are shown.

Triglyceride Measurement.

On the day indicated, serum triglyceride levels are measured using a spectrophotometer (Cobas DP-25P).

Liver Steatohepatitis Score.

A liver segment from each mouse was fixed in 10% formaldehyde and embedded in paraffin for histological analysis. Five sections (5 µm) are stained with hematoxylin/eosin and reviewed by two pathologists in a blinded fashion. Histological examination and the steatohepatitis grade scoring (NASH score) are performed using the steatohepatitis scoring system.

Histological Examination.

Hematoxylin/eosin staining of paraffin-embedded liver sections is performed. Sections are examined by two experienced pathologists (VD, YS) that are blinded to the experiment conditions.

Figure 1:
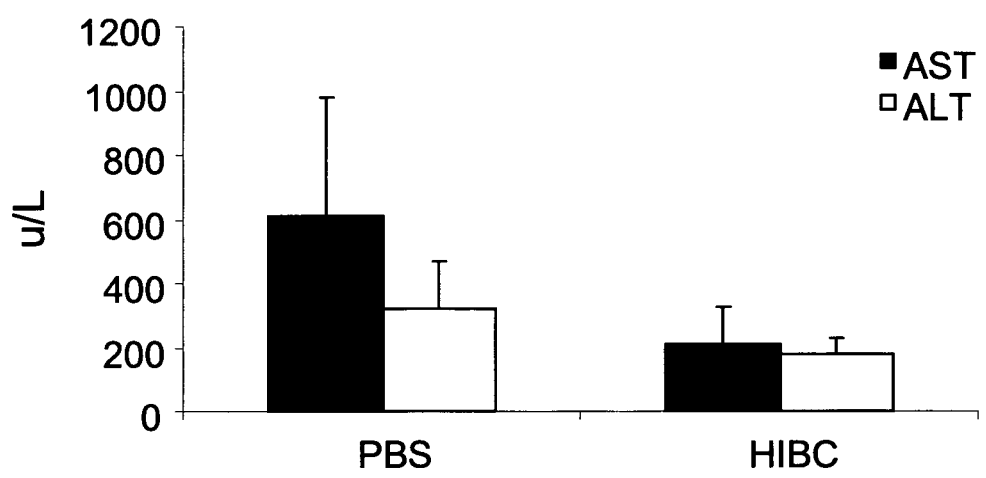
FIG. 1. Oral administration of anti-LPS enriched colostrum-derived immunoglobulin preparation decreases liver enzymes.

Example 4: Oral Administration of Anti-LPS Enriched Colostrum-Derived Immunoglobulin Preparation Decreases Liver Enzymes The inventors evaluated whether the liver enzyme levels, which indicate liver injury, of animals orally administered with ånti-LPS enriched colostrum-derived immunoglobulin preparation are improved due to the treatment. Levels of aspartyl transaminase (AST) and alanine aminotransferase (ALT) activities were determined by a clinical chemistry analyzer, Reflovet Plus (Roche Diagnostics, GmbH, Mannheim, Germany). FIG. 1 demonstrates the decrease was significant for AST group A versus B (* p<0.001). This demonstrates amelioration of liver injury, as manifested by a clear and significant decrease in ALT and AST serum levels vs. the control group.

Example 5: Oral Anti-LPS Enriched Colostrum-Derived Immunoglobulin Preparation Increases the Expression of CD4+CD25+ Regulatory T Cells in the Liver Isolation of Intrahepatic Lymphocytes.

Intrahepatic lymphocytes were isolated after mice were sacrificed, as follows: After the removal of livers, they were kept in medium (RPMI-1640+FCS). Then, livers were crushed through a stainless mesh (size 60, Sigma) and the cell suspension was placed in a 50-ml tube for 5 min. Lymphoprep (10 ml, Ficoll, Axis-Shield PoC AS, Oslo, Norway) was placed under similar volume of cell suspension in 50-ml tubes. Tubes were centrifuged at 1800 rpm for 18 min. Cells in the interface were collected and centrifuged at 1800 rpm for 10 min, to obtain a pellet of cells depleted of hepatocytes to a final volume of 250□l. Approximately $1\times10^6$ cells/mouse liver, were recovered and analyzed by flow cytometry.

Flow Cytometry.

Surface two to three color staining of cells were done with the following surface antibodies: anti-CD4-FITC and anti-CD25-PE. (Antibodies were purchased from eBioscience, San Diego, Calif.). Surface staining was performed by incubating freshly isolated cells with antibodies and anti-CD16/32 (blocks Fc, eBioscience) at 4° C. in FACS buffer containing PBS and 0.5% BSA, for 30 min. Cells were washed twice with FACS buffer, resuspended in FACS buffer, and analyzed by flow cytometry. Appropriate isotype controls were used in all experiments. Analysis was performed using a FACSCalibur instrument (Becton Dickinson, San Jose, Calif.) with FCS express V.3 software (DeNovo software, Los Angeles, Calif.).

Statistical Analysis.

Statistical analysis was performed using the student t test. $P \leq 0.05$ was considered significant.

Figure 2A:
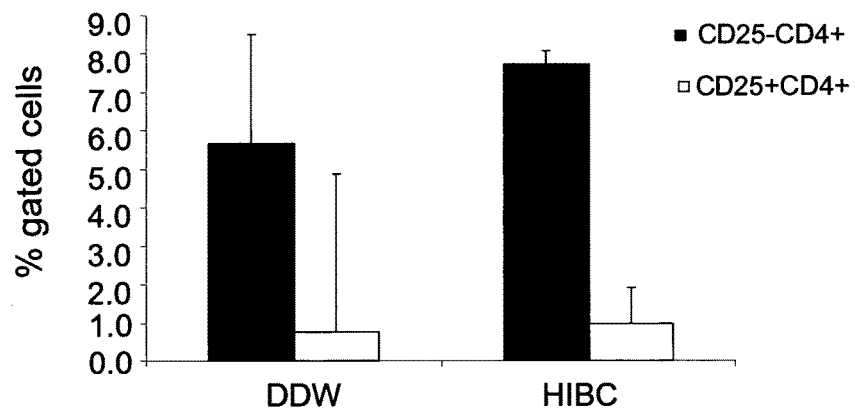

To determine the specificity of the increase in regulatory T cells in the liver, the average surface expression of markers (CD4+CD25) on hepatic lymphocytes was measured using flow cytometry on day 7 (sacrifice day) in all mice treated with 3.0 mg anti-LPS enriched colostrum-derived immunoglobulin preparation. FIG. 2A demonstrates oral anti-LPS enriched colostrum-derived immunoglobulin preparation increases the expression of CD4+CD25+ regulatory T cells in the liver. Gating was on CD4 and values are mean±SD.

Figure 2B:
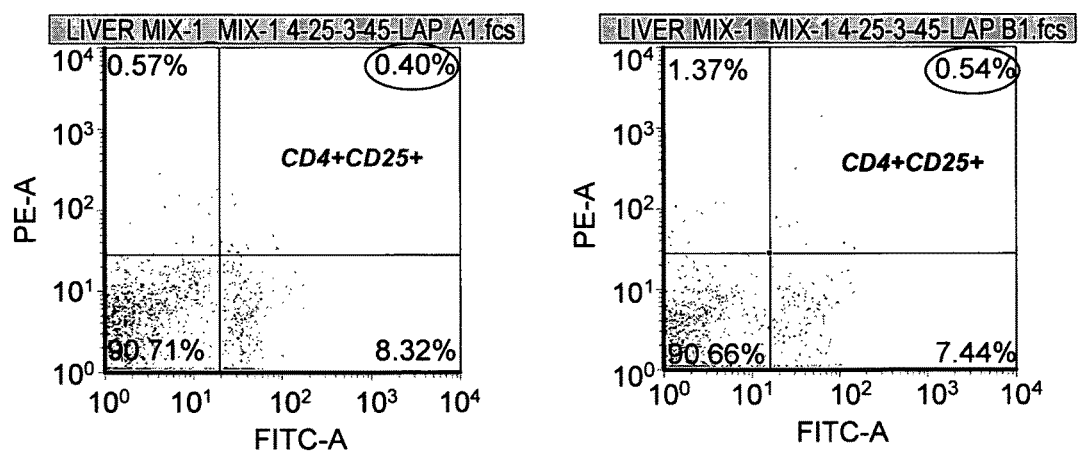

A representative dot blot derived from FACS performed on lymphocytes isolated from the livers of mice treated with anti-LPS enriched colostrum-derived immunoglobulin preparation (group B) or from untreated controls (group A) is shown in FIG. 2B which shows oral anti-LPS enriched colostrum-derived immunoglobulin preparation increases the expression of CD4+CD25+ regulatory T cells in the liver.

Example 6: Oral Anti-LPS Enriched Colostrum-Derived Immunoglobulin Preparation Increases the Expression of CD25+CD4+LAP−, CD45+LAP+ and CD3+LAP+ Regulatory T Cells in the Liver Isolation of intrahepatic lymphocytes and FACS analysis was performed as described above.

Flow Cytometry.

For LAP staining the following antibodies were used: anti-CD3-Alexa-fluor 405, anti-CD45-PerCP-Cy5.5 and anti-LAP-APC. Affinity-purified biotinylated goat anti-LAP specific polyclonal antibody was purchased from R&D Systems (Minneapolis, Minn., USA), and strepavidin-APC was used as secondary reagent for detecting the biotinylated primary antibody (R&D). For LAP staining cells were preincubated with LAP/control antibody for 20 min, and stained with CD3-Alexa-fluor 405 or CD45-PerCP-Cy5.5, followed by strepavidin-APC staining.

In order to determine whether oral anti-LPS enriched colostrum-derived immunoglobulin preparation promotes Tregs, the inventors examined the effect of oral administration on the tissue derived subsets of regulatory T cells. FIG. 3 shows the average surface expression of markers (CD25+ CD4+LAP−, CD45+LAP+ and CD3+LAP+) on hepatic lymphocytes measured using flow cytometry on day 7 (sacrifice day) in all mice treated with 3.0 mg. Values are means. FIGS. 3A and B demonstrate oral administration of anti-LPS enriched colostrum-derived immunoglobulin preparation increased a subset of CD25+CD4+LAP−, CD45+LAP+ and CD3+LAP+ regulatory T cells in the liver.

Example 7: Oral Anti-LPS Enriched Colostrum-Derived Immunoglobulin Preparation Increases the Expression of CD45+LAP+ and CD8+ LAP+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. FIG. 4 shows the average surface expression of markers (CD45+LAP+ and CD8+LAP+) on splenic lymphocytes measured using flow cytometry on day 7 (sacrifice day) in all mice treated with 3.0 mg. Values are mean±SD. FIGS. 4A and B demonstrate oral administration of anti-LPS enriched colostrum-derived immunoglobulin preparation increases a subset of CD45+LAP+ and CD8+LAP+ regulatory T cells in the spleen.

Example 8: Oral Administration of Colostrum Enriched with Anti LPS Antibodies to Ob/Ob Mice

TABLE 2

| Experimental design | | | |
|---|---|---|---|
| Group | PBS | T-IgG | HIBC |
| A<br>N = 4 | 30 ul | — | — |
| B<br>N = 4 | — | 100 ug/ml | — |
| C<br>N = 4 | — | — | 100 ug/ml |

Experimental Groups.

Three groups of mice (Table 2) were studied. Ob/Ob mice (4 per group) were fed (PO) daily for 25 days (5 days a week) with 30 ul of PBS (control, group A) or 30 ul (=100 ug) of T-IgG colostrum (group B) which was dissolved in water, or with or 30 ul (=100 ug) of anti-LPS enriched colostrum-derived immunoglobulin preparation (group C). After 4 weeks mice were sacrificed. On sacrifice day, cardiac blood was collected by standard techniques then serum was obtained.

Animals.

For the Ob/Ob model, we used young (age 6-7 weeks) male C57BL/6 Ob/Ob mice which were purchased from Harlan Laboratories (USA). All mice were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Example 9: Oral T-IgG Decreases Serum Insulin in Ob/Ob Mice

To further assess the effect of oral anti-LPS enriched colostrum-derived immunoglobulin preparation, levels of fasting serum insulin were determined in mice of groups A-C following four weeks of T-IgG or HIBC administered orally. Serum insulin was determined by "sandwich" ELISA, using the commercial kit of Mercodia AB (Uppsala, Sweden) according to the manufacturer's instructions. Sera were collected from Ob/Ob mice on day 30 after sacrificing the mice. FIG. 5 demonstrates mice administered T-IgG exhibited a decrease in serum insulin levels, indicating the beneficial impact of the anti LPS antibodies on insulin resistance. Moreover, the decrease observed in provides data in support of an important role for the colostrum derived adjuvants in the metabolic effect.

Example 10: Oral Anti-LPS Enriched Colostrum-Derived Immunoglobulin Preparation Decreases Glucose Tolerance in Ob/Ob Mice In order to examine whether oral anti-LPS enriched colostrum-derived immunoglobulin preparation can decrease in serum glucose levels, Ob/Ob mice underwent a glucose tolerance test (GTT) on day 30 after overnight fasting. Glucose was administered orally (1.25 g per kg). Serum glucose measurements were performed on tail-vein blood every 15 min for 3 h. Glucose levels were measured by a standard glucometer.

As shown in FIG. 6, mice administered HIBC improved glucose tolerance demonstrated by lower glucose values at glucose tolerance test with a decrease in the area under the curve as compared to the control group. Taken together, the data obtained in Examples 9 and 10 supports the importance of HIBC according to the present invention in the improvement of the metabolic syndrome.

Example 11: Oral Administration of Anti-LPS Enriched Colostrum-Derived Immunoglobulin Preparation Decreases Liver Injury in Ob/Ob Mice Having shown that oral administration of anti-LPS enriched colostrum-derived immunoglobulin preparation improves various metabolic syndrome markers, such as decreasing glucose tolerance and decreasing serum insulin, the inventors next evaluated whether the liver enzyme levels, which indicate liver injury, of animals fed with the preparation have also improved due to the treatment. Levels of AST and ALT activities were determined by a clinical chemistry analyzer, Reflovet Plus (Roche Diagnostics, GmbH, Mannheim, Germany). FIG. 7 demonstrates a decrease of AST and ALT levels in T-IgG-colostrum-treated mice.

Example 12: Oral Administration of Anti-LPS Enriched Colostrum-Derived Immunoglobulin Preparation Decreases Hepatic TGs in Ob/Ob Mice Having shown that oral administration of anti-LPS enriched colostrum-derived immunoglobulin preparation improves various metabolic syndrome markers, the effect of oral administration of anti-LPS enriched colostrum-derived immunoglobulin preparation and T-IgG colostrums on hepatic triglycerides accumulation was determined at the end of the study, after sacrificing the mice. Accumulation of intracellular triglycerides (TGs) within the liver was quantified using a modification of the Folch method. TGs were extracted from aliquots of snap-frozen livers and then assayed spectrophotometrically using the GPO-Trinder kit (Sigma, Rehovot, Israel) and were normalized to the protein content in the homogenate. Heaptic triglyceride content was calculated on all treated and control groups.

FIG. 8 demonstrates that oral administration anti-LPS enriched colostrum-derived immunoglobulin preparation decreased hepatic triglyceride content compared to mice in the control group. The decrease was significant for HIBC relative to controls (* P<0.04).

Example 13: Oral Administration of Anti-LPS Enriched Colostrum-Derived Immunoglobulin Preparation Increases the Expression of CD3+LAP+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. FIG. 9 shows the average surface expression of markers (CD3+LAP+) on splenic lymphocytes measured using flow cytometry on day 25 (sacrifice day) in all Ob/Ob mice. Values are mean±SD. FIGS. 9A and B demonstrate oral administration of T-IgG increases a subset of CD3+ LAP+ regulatory T cells in the spleen.

Example 14: Oral Administration of Anti-LPS Enriched Colostrum-Derived Immunoglobulin Preparation Increases the Expression of CD8+CD25+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. Isolation of splenic lymphocytes, flow cytometry procedures and analysis and staining antibodies, are the same as described above. FIGS. 10 and 11 show the average surface expression of markers (CD8+CD25+) on splenic lymphocytes measured using flow cytometry on day 25 (sacrifice day) in all Ob/Ob mice. Values are mean±SD.

FIGS. 10 and 11 demonstrate oral administration of T-IgG increases a subset of CD8+CD25+ regulatory T cells in the spleen.

Figure 12A:
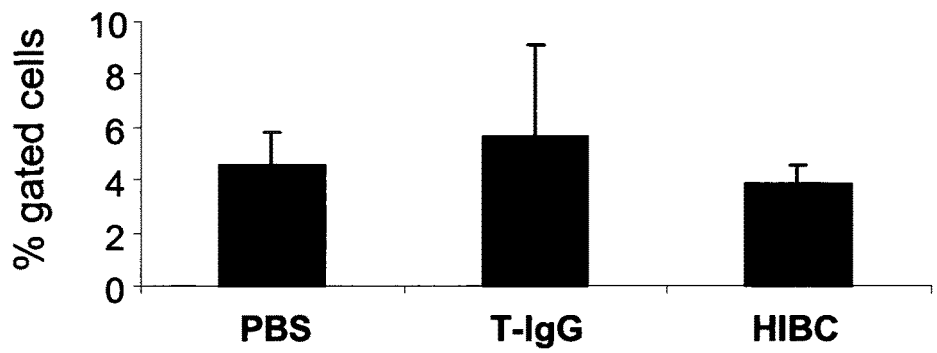
Figure 12B:
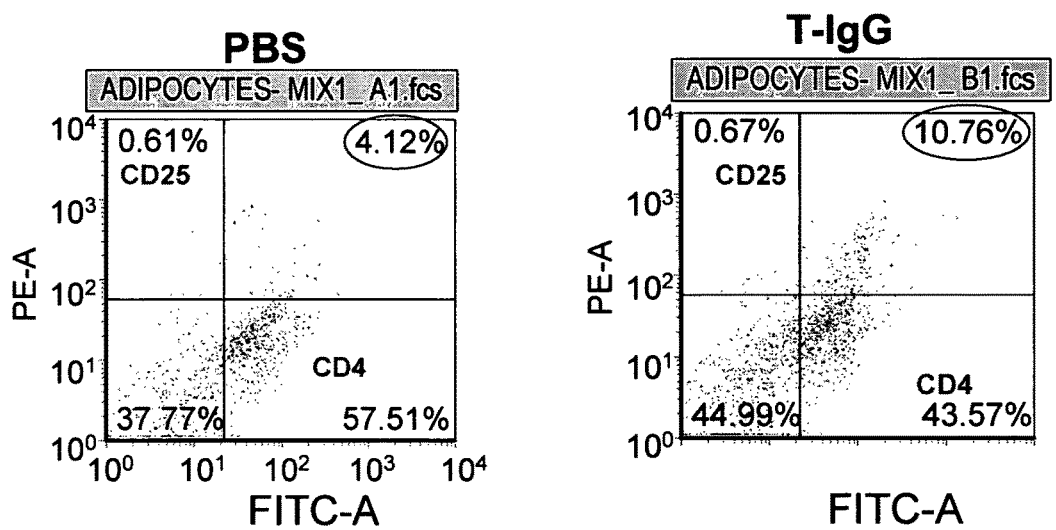

Example 15: Oral Anti-LPS Enriched Colostrum-Derived Immunoglobulin Preparation Increases the Expression of CD4+CD25+ Regulatory T Cells in Adipose Tissue In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from adipose tissue. Adipose tissue was isolated from Ob/Ob mice immediately after sacrifice. Tissues (visceral fat pads) were minced into fine pieces. Minced samples were placed in Krebs-Ringer bicarbonate buffer (3 mL/g adipose tissue) containing 10 mM glucose and 2.5% bovine serum albumin, incubated with 840 U/g collagenase type I (Sigma, Rehovot, Israel) at 37° C. for 1 hour. Cells were filtered twice through chiffon mesh (100 um) and centrifuged 50 g for 5 min. Floating adipocytes were separated from pelleted adipose tissue-associated stromal-vascular (S/V) cells. fraction: The infranatant fraction was removed and centrifuged at 200 g for 5 min to pellet the S/V cells. FIGS. 12A and 12B show the average surface expression of markers (CD4+CD25+) on adipose tissue lymphocytes measured using flow cytometry on day 25 (sacrifice day) in all Ob/Ob mice.

FIG. 12 demonstrates oral administration of T-IgG increases a subset of CD4+CD25+ regulatory T cells in adipose tissue.

Example 16: Oral Anti-LPS Enriched Colostrum-Derived Immunoglobulin Preparation Increases the Expression of CD3+LAP+ Regulatory T Cells in Adipose Tissue In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from adipose tissue isolated according to the method discussed above. FIGS. 13A and 13B show the average surface expression of markers (CD3+LAP+) on adipose tissue lymphocytes measured using flow cytometry on day 25 (sacrifice day) in all Ob/Ob mice.

FIG. 13 demonstrates oral administration of T-IgG increases a subset of CD3+LAP+ regulatory T cells in adipose tissue.

Example 17: Oral Anti-LPS Enriched Colostrum-Derived Immunoglobulin Preparation Increases the Expression of CD4+CD25+ Regulatory T Cells in Stromal Vascular Cells (Containing Preadipocytes)

In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from Stromal Vascular Cells containing preadipocytes isolated according to the method discussed above.

FIGS. 14A and 14B show the average surface expression of markers (CD4+CD25+) on adipose tissue lymphocytes measured using flow cytometry on day 25 (sacrifice day) in all Ob/Ob mice.

FIG. 14 demonstrates oral administration of T-IgG increases a subset of CD4+CD25+ regulatory T cells in the Stromel Vascular Cells containing preadipocytes.

To further investigate this population of cells, FACS analysis was performed on lymphocytes isolated from Stromal Vascular Cells to examine the expression of markers (CD4+CD25+LAP+) (on day 25 (sacrifice day) in all ob/ob mice.)

Figure 15A:
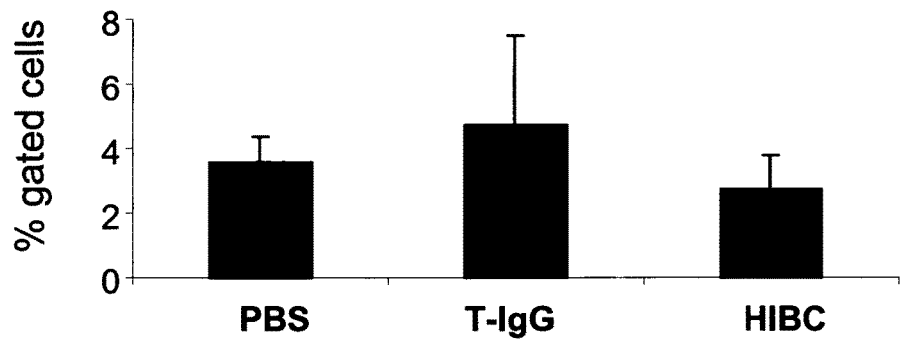
Figure 15B:
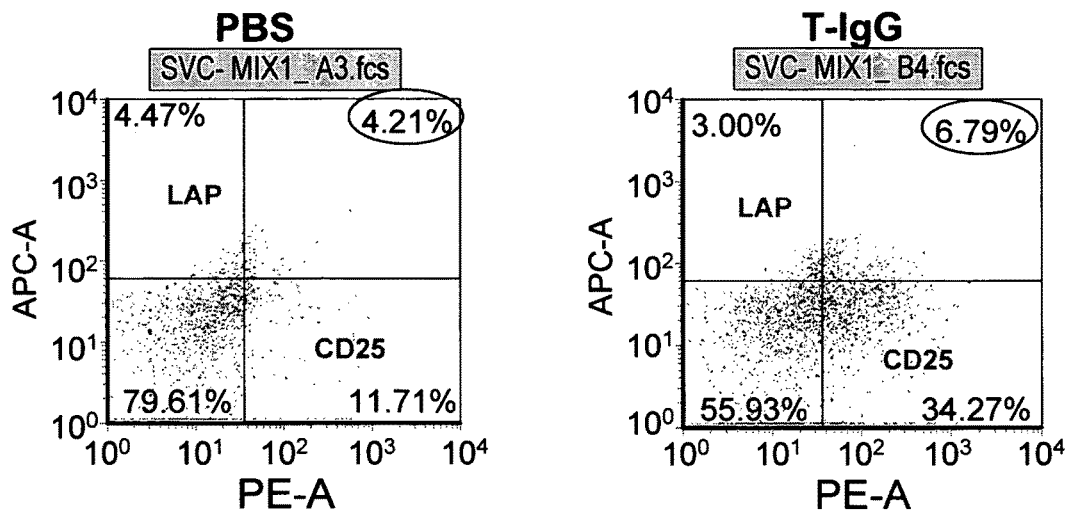

FIGS. 15A and 15B show the average surface expression of markers (CD4+CD25+LAP+) on adipose tissue lymphocytes measured using flow cytometry on day 25 (sacrifice day) in all Ob/Ob mice.

FIG. 15 demonstrates oral administration of T-IgG increases a subset of CD4+CD25+ regulatory T cells in the Stromal Vascular Cells containing preadipocytes.

Example 18: Dosage Studies of Anti-LPS Enriched Colostrum-Derived Immunoglobulin Preparation in Ob/Ob Mice

TABLE 3

Experimental design

| Group | PBS | T-IgG | T-IgG | T-IgG | T-IgG | HIBC |
|---|---|---|---|---|---|---|
| A N = 5 | 30 µl | — | — | — | — | — |
| B N = 5 | — | 1 ug | — | — | — | — |
| C N = 5 | — | — | 100 ug | — | — | — |
| D N = 5 | — | — | — | 1 mg | — | — |
| E N = 5 | — | — | — | — | 3 mg | — |
| F N = 5 | — | — | — | — | — | 100 ug |

Experimental Groups.

Six groups of mice (Table 3) were studied. Ob/Ob mice (5 per group) were fed (PO) daily for 25 days (5 days a week) with 30 ul of PBS (control, group A) or 30 ul (=1 ug) of T-IgG colostrum (group B), or 30 ul (=100 ug) of T-IgG colostrum (group C) or 30 ul (=1 mg) of T-IgG colostrum (group D) or 30 ul (=3 mg) of T-IgG colostrum (group E) or 30 ul (=100 ug) of HIBC colostrum (group F). Both colostrum preparations were dissolved in water.

After 4 weeks mice were sacrificed. On sacrifice day, cardiac blood was collected by standard techniques then serum was obtained for future purposes.

Animals.

For the Ob/Ob model, we used young (age 6-7 weeks) male C57BL/6 Ob/Ob mice which were purchased from Harlan Laboratories (USA). All mice were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Example 19: Oral Administration of Anti-LPS Enriched Colostrum-Derived Immunoglobulin Decreases Liver Enzymes in Ob/Ob Mice Levels of AST and ALT activities were determined by a clinical chemistry analyzer, as described above. FIG. 6 demonstrates 1 mg of T-IgG was the most effective dose in decreasing liver enzymes.

Example 20: Oral Administration of Anti-LPS Enriched Colostrum-Derived Immunoglobulin Decreases Total Cholesterol in Ob/Ob Mice Plasma triglycerides and total cholesterol were determined by a clinical chemistry analyzer, Reflovet Plus (Roche Diagnostics, GmbH, Mannheim, Germany) as described above. FIG. 17 demonstrates 100 ug of T-IgG was the most effective dose in decreasing total cholesterol.

Example 21: Oral Administration of Anti-LPS Enriched Colostrum-Derived Immunoglobulin Decreases Hepatic TGs in Ob/Ob Mice Accumulation of intracellular triglycerides (TGs) within the liver was quantified using a modification of the Folch method. TGs were extracted from aliquots of snap-frozen livers and then assayed spectrophotometrically using the GPO-Trinder kit (Sigma, Rehovot, Israel) and were normalized to the protein content in the homogenate.

FIG. 18 demonstrates 100 ug of 1 mg, 3 mg and 100 ug of T-IgG were the most effective doses in decreasing hepatic triglycerides. The decrease was statistically significant for group A versus D, E, F (* $p<0.05$).

Example 22: Oral Administration of 1 ug, 1 mg, 3 mg of T-IgG, Along with 100 ug HIBC, Decreased CD3+NK1.1+ Cells in the Livers of Ob/Ob Mice FACS analysis was performed on lymphocytes isolated from livers of Ob/Ob mice. Average of expression of markers (CD3+NK1.1+) on hepatic lymphocytes was measured using flow cytometry on day 25 (sacrifice day) in all ob/ob mice. For flow cytometry, the following antibodies were used: anti-CD3-FITC and anti NK1.1-PE. Surface staining and FACS analysis was performed as described above.

FIG. 19A demonstrates oral administration of 1 ug, 1 mg, 3 mg of T-IgG, along with 100 ug HIBC, decreased CD3+ NK1.1+ cells in the livers of Ob/Ob mice. Furthermore, FIG.

19B demonstrates oral administration of 1 ug and 100 ug of T-IgG, decreased CD3+NK1.1+ cells in the livers of Ob/Ob mice Example 23: Oral Administration of T-IgG and HIBC Colostrums, Increases CD4+CD25+LAP−/LAP+ Cells in the Livers of Ob/Ob Mice In order to determine dosages of oral anti-LPS enriched colostrum-derived immunoglobulin preparation that promotes Tregs in livers, the inventors examined the effect of oral administration on the tissue derived subsets of regulatory T cells. FACS analysis was performed on lymphocytes isolated from livers according to the method discussed above. FACS analysis was performed on lymphocytes isolated from livers of Ob/Ob mice. FIG. 20 shows the average of expression of markers (on hepatic lymphocytes was measured using flow cytometry on day 25 (sacrifice day) in all ob/ob mice.

Figure 20B:
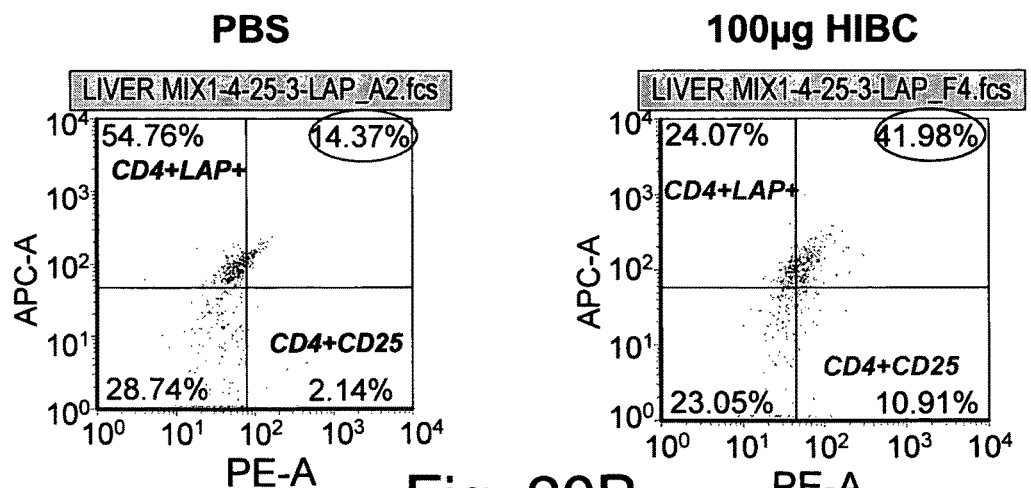

FIG. 20A demonstrates oral administration of T-IgG and HIBC colostrums, increases CD4+CD25+LAP−/LAP+ cells in the livers of Ob/Ob mice. FIG. 20B demonstrates oral administration of 100 ug of HIBC colostrum, increases CD4+CD25+LAP+ cells in the livers of Ob/Ob mice.

Example 24: Oral Administration of T-IgG and of HIBC-Colostrums, Induces Changes in CD25+LAP− Hepatic Lymphocytes FIG. 21 demonstrates oral administration of 1 ug, 1 mg, 3 mg of T-IgG, along with 100 ug HIBC, induces changes in CD25+LAP− lymphocytes in the livers of Ob/Ob mice.

Figure 22B:
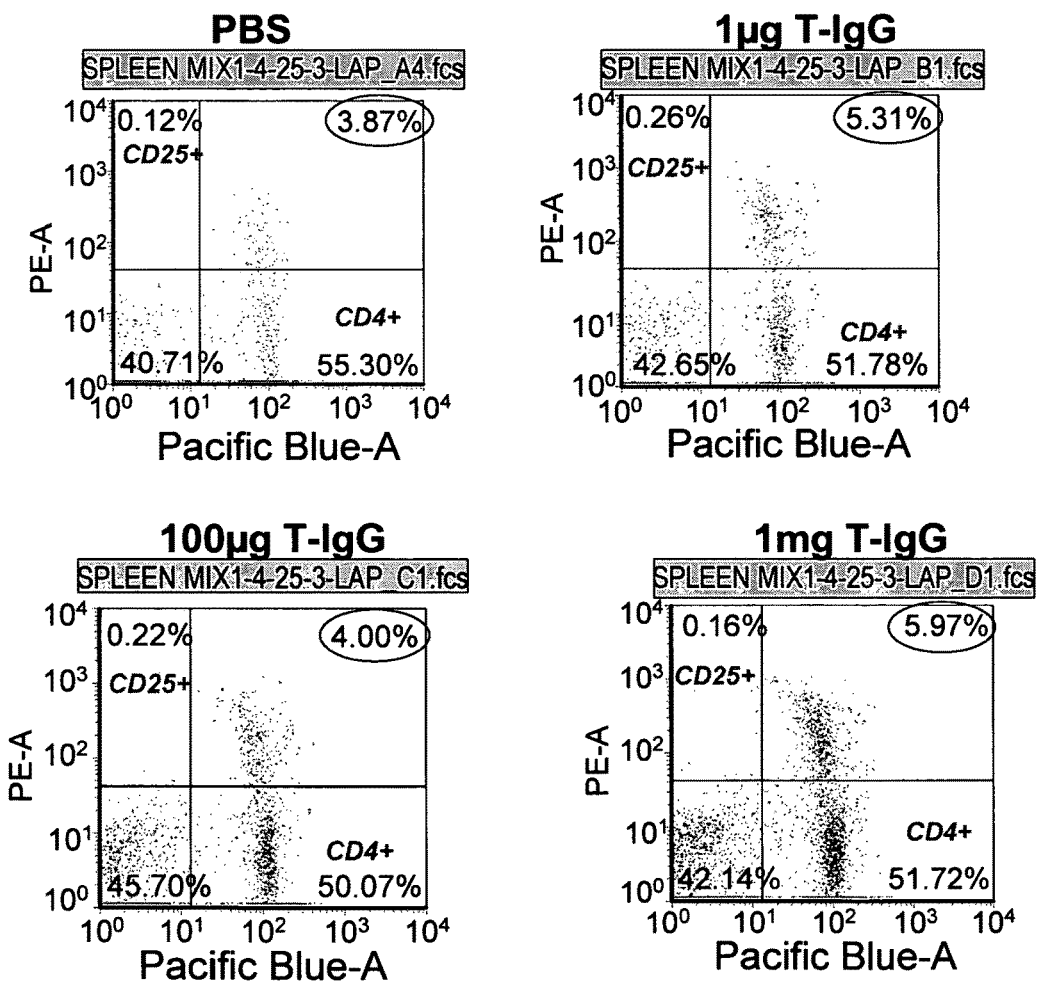

Example 25: Oral Administration of T-IgG and of HIBC-Colostrums Induces Changes in CD25+LAP+ Splenic Lymphocytes FIG. 22A demonstrates administration of T-IgG and of HIBC-colostrums, decreases CD25+LAP+ splenic lymphocytes. FIG. 22B demonstrates oral administration of T-IgG-colostrums increases CD25+LAP+ splenic lymphocytes.

Figure 24:
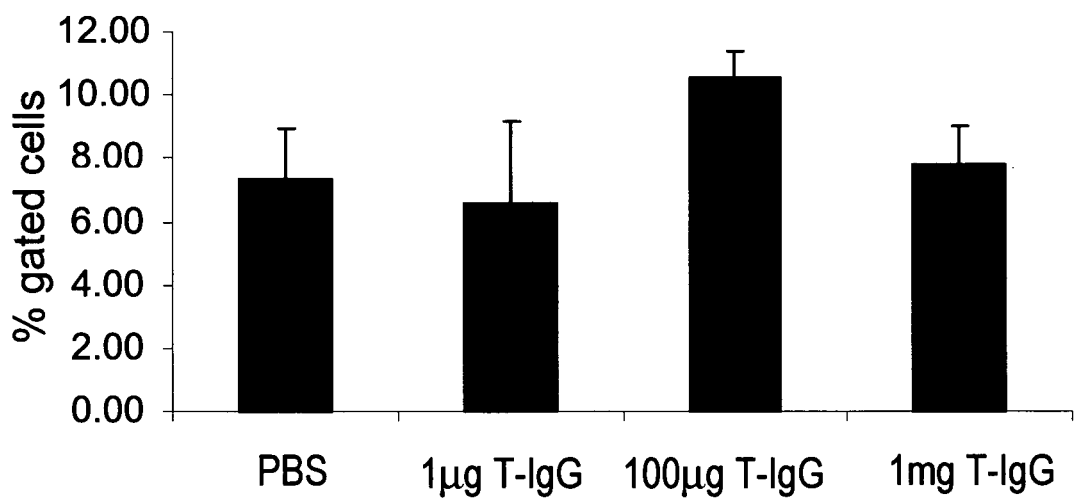

Example 26: Oral Administration of 1 and 3 mg of T-IgG and of 100 μg of HIBC-Colostrums, Increases CD4+CD25+LAP− Splenic Lymphocytes FACS analysis was performed on lymphocytes isolated from livers of Ob/Ob mice. FIG. 23 shows the average of expression of markers (CD4+CD25+LAP−) on splenic lymphocytes was measured using flow cytometry on day 25 (sacrifice day) in all ob/ob mice. FIG. 23 demonstrates oral administration of 1 and 3 mg of T-IgG and of 1000 g of HIBC-colostrums, increases CD4+CD25+LAP− splenic lymphocytes Example 27: Oral Administration of T-IgG-Colostrums, Increases CD4+CD25+ in Adipose Tissue FACS analysis was performed on lymphocytes isolated from adipose tissues of Ob/Ob mice, as described above. FIG. 24 shows Average of expression of markers (CD4+ CD25+) on adipose tissue cells was measured using flow cytometry on day 25 (sacrifice day) in all ob/ob mice. FIG. 24 demonstrates oral administration of T-IgG-colostrums, increases CD4+CD25+ lymphocytes in adipose tissue.

Example 28: Oral Administration of 100 μg of T-IgG-Colostrum, Increases CD4+CD25+ in Adipocytes FACS analysis was performed on adipocytes isolated from adipose tissues of Ob/Ob mice, as described above. FIG. 25A demonstrates the average of expression of markers (CD4+CD25+) on adipocytes was measured using flow cytometry on day 25 (sacrifice day) in all ob/ob mice.

FIG. 25A demonstrates administration of 100 ug of T-IgG-colostrum, increases CD4+CD25+ in adipocytes. FIG. 25B demonstrates oral administration of 1000 g of T-IgG-colostrum, increases CD4+CD25+ in adipocytes.

Example 29: Oral Administration of T-IgG-Colostrum, Increases CD3+LAP+ in Adipocytes FACS analysis was performed on adipocytes isolated from adipose tissues of Ob/Ob mice, as described above. FIG. 26 shows the average of expression of markers (CD3+ LAP+) on adipocytes was measured using flow cytometry on day 25 (sacrifice day) in all ob/ob mice.

FIG. 26A demonstrates oral administration of T-IgG-colostrum, increases CD3+LAP+ in adipocytes. FIG. 26B demonstrates oral administration of T-IgG-colostrum, increases CD3+LAP+ in adipocytes.

Example 30: Oral Administration of T-IgG-Colostrum, Increases CD4+CD25+LAP− in Adipocytes FIG. 27A demonstrates administration of T-IgG-colostrum, increases CD4+CD25+LAP− in adipocytes.

Example 31: Oral Administration of Anti LPS Enriched Colostrum Decreases Bacterial Translocation in a Model of Hepatitis To examine bacterial translocation and hepatitis, groups of mice were treated as follows:
Group A: Treated with BCP: antibody free colostrum
Group B: anti LPS containing colostrum
Mice were fed with colostrum for 4 days prior to induction of Con A hepatitis.
Administration of Con A and Measurement of Serum Transaminase Activities.
Con A was purchased from MP Biomedicals (Ohio, USA). Con A (0.5 mg, 20 mg/kg) was dissolved in 200 μL of 50 mM Tris (pH 7), 150 mM NaCl, 4 mM $CaCl_2$, and injected intravenously into mice. Sera from individual mice were obtained 8 or 20 h after Con A injection. Serum activities of alanine aminotransferase (ALT) and aspartate aminotransferase (AST) were measured using an automatic analyzer.
To assess of bacterial translocation lipopolysaccharide (LPS) levels were measured using the using the limulus amebocyte lysate (LAL) chromogenic assay; LAL is a measure for degree of bacterial translocation.
Table 4 demonstrates oral administration of anti LPS colostrum decreased bacterial translocation, as shown by a decrease in average LAL levels.

TABLE 4

|  |  | average | std. dev. | P value |
|---|---|---|---|---|
| Group A | ConA + BCP | 1.52 | 0.75 | 0.37 |
| Group B | ConA + LPS Colostrum | 1.18 | 0.30 |  | importantly, the reduced bacterial translocation was associated with improved in liver enzyme ALT which is a marker of liver damage, as shown in table 5

TABLE 5

|  |  | ALT | average | STD. DEV. |
|---|---|---|---|---|
| Group A | A1 | 28170 |  |  |
| ConA + BCP | A2 | 857.6 |  |  |
|  | A3 | 1356.8 |  |  |
|  | A4 | 340.8 |  |  |
|  | A5 | 26340 |  |  |
|  |  |  | 11413.04 | 14480.59 |
| Group B | B1 | 10992 |  |  |
| ConA + T- | B2 | 796.8 |  |  |
| IgG | B3 | 187.2 |  |  |
|  | B4 | 2816 |  |  |
|  | B5 | 12672 |  |  |
|  |  |  | 5492.8 | 5898.076 |

Example 32: Preparation of Compositions Containing Colostrum-Derived Anti-LPS Enriched Preparations and Anti-Insulin Antibodies For preparation of the anti-LPS enriched immunoglobulin preparation, colostrum was collected from approximately 200 commercial diary cowherds. The cows in these herds, as well as being vaccinated for routine cattle pathogens, have been vaccinated with a proprietary Anadis vaccine against the outer cell wall antigens of multiple strains of *E. coli* bacteria, a major organism in human gut microflora. For preparation of the anti-insulin enriched immunoglobulin preparation, three dairy cows are immunized with insulin conjugated to KLH as an antigen. The antigen vaccines are administered during the last eight weeks of gestation. Colostral milk is collected during the first two days of lactation. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

The anti-LPS enriched immunoglobulin preparation and the anti-insulin enriched immunoglobulin preparation are mixed to form a composition for use as described below.

For immune mediated hepatitis model, eleven to twelve weeks old male C57/bl mice are tail vein injected with a dose of 500 µglinouse (approximately 15 mg/kg) of Con A (MP Biomedicals, USA) which is dissolved in 50 mM Trig pH 7, 150 mM NaCl, 4 mM $CaCl_2$, known to induce hepatitis. Animals of all tested groups are orally administered (e.g. by gavage) using different concentrations of the composition containing the anti-LPS and anti-insulin enriched immunoglobulin preparations and compared to untreated controls. Animals of all tested groups are followed for the following parameters: serum aspartate aminotransferase (AST) and alanine aminotransferase (ALT) levels, histological examination of liver specimens, FACS analysis of intrahepatic and intrasplenic lymphocytes for NKT markers, measurement of TGs, total cholesterol, glucose tolerance, serum insulin, serum glucose, cytokine levels and Western blot analysis for the expression of the transcription factors STAT 1, 4 and 6 and NFκB and are compared to control groups.

The claims defining the invention are as follows:

1. A method of improving liver function in a subject with non alcoholic hepatic steatohepatitis (NASH), the method comprising:
    selecting a subject who has NASH; and
    orally administering to the selected subject a therapeutically effective dose of an anti-LPS enriched immunoglobulin preparation derived from colostrum, thereby improving liver function in the subject with NASH.

2. The method of claim 1, comprising determining a level of aspartate aminotransferase (AST) or alanine aminotransferase (ALT) in the subject, and selecting a subject who has impaired liver function based on the level of aspartate aminotransferase (AST) or alanine aminotransferase (ALT) in the subject.

3. The method of claim 1, further comprising determining a level of aspartate aminotransferase (AST) or alanine aminotransferase (ALT) in the subject, wherein a decrease in levels of AST or ALT indicates an improvement in liver function.

4. The method of claim 1, wherein the colostrum is bovine colostrum.

5. The method of claim 1, wherein the colostrum is freeze-dried colostrum.

6. The method of claim 5, wherein the freeze-dried colostrum is in a tablet.

* * * * *